United States Patent
Crandall et al.

(10) Patent No.: US 8,632,914 B2
(45) Date of Patent: Jan. 21, 2014

(54) TRIAZOLIUM AND IMIDAZOLIUM SALTS AND USES THEREOF

(75) Inventors: Ian E. Crandall, North York (CA); Walter A. Szarek, Kingston (CA); Jason Z. Vlahakis, Kingston (CA)

(73) Assignee: University Health Network, Toronto, Ontario (CA)

( * ) Notice: Subject to any disclaimer, the term of this patent is extended or adjusted under 35 U.S.C. 154(b) by 0 days.

(21) Appl. No.: 13/062,359

(22) PCT Filed: Sep. 4, 2009

(86) PCT No.: PCT/CA2009/001224
§ 371 (c)(1),
(2), (4) Date: Mar. 4, 2011

(87) PCT Pub. No.: WO2010/025558
PCT Pub. Date: Mar. 11, 2010

(65) Prior Publication Data
US 2011/0257235 A1    Oct. 20, 2011

Related U.S. Application Data

(60) Provisional application No. 61/094,536, filed on Sep. 5, 2008.

(51) Int. Cl.
C07F 15/00 (2006.01)
C07F 11/00 (2006.01)
C07D 235/04 (2006.01)
C07D 487/14 (2006.01)

(52) U.S. Cl.
USPC ...... 429/199; 514/359; 548/262.2; 548/300.1

(58) Field of Classification Search
USPC ............. 429/199; 548/262.2, 300.1; 514/359
See application file for complete search history.

(56) References Cited

U.S. PATENT DOCUMENTS 5,620,595 A * 4/1997 Austin et al. ............. 210/167.11
5,631,274 A * 5/1997 Austin et al. .................. 514/397
2009/0092854 A1   4/2009 Waltrs et al.

FOREIGN PATENT DOCUMENTS

| CA | 2146256 | 4/1994 | | |
|---|---|---|---|---|
| DE | 1076136 | 8/1958 | | |
| EP | 1834803 | 9/2007 | | |
| WO | WO 94/08972 | * 4/1994 | ............ | C07D 233/58 |
| WO | WO 9408972 | * 4/1994 | ............ | C07D 233/58 |

OTHER PUBLICATIONS

Zeng, et al., Chem. Mater., 2008, 20, 2719-2726.*
Patani, et al., Chem. Rev., 1996, vol. 96, No. 8, p. 3148, Table 3.*
Zeng, et al., Chem. Mater., 2008, 20, 2719-2726. (previously provided see office action mail date Jul. 18, 2012).*
Becker, H. G. O.; Hoffmann, G.; Gwan, K. M.; Knüpfer, L. Journal fuer Praktische Chemie 1988, 330, 325-337.
Breman, J. G.; Egan, A.; Keusch, G. T. Am J Trop Med Hyg 2001, 64(1-2 Suppl), iv).
Brenna, S.; Posset, T.; Furrer, J.; Bluemel, J. Chemistry—A European Journal 2006, 12, 2880-2888.
Campling, B. G.; Pym, J.;Galbraith, P. R.; Cole, S. P. Leuk Res 1988, 12(10), 823.
Chu, Y.; Deng, H.; Cheng, J-P. J. Org. Chem. 2007, 72, 7790-7793.
Crandall, I.E.; Szarek, W.A.; Vlahakis, J.Z.; Xu, Y.; Vohra, R.; Sui, J.; Kisilevsky, R. Sulfated cyclodextrins inhibit the entry of Plasmodium into red blood cells: Implications for malarial therapy. Biochemical Pharmacology 2007, 73, 632-642.
Cui, X., J.Z. Vlahakis, I.E. Crandall, and W.A. Szarek. 2008. Anti-Plasmodium activity of tetrazolium salts. Bioorg Med Chem 16:1927-1947.
Gottlieb, H. E.; Kotlyar, V.;Nudelman, A. J. Org. Chem. 1997, 62, 7512.
Hamzé, A. et al. J. Med. Chem. 2005, 48, 3639-3643.
Hunfeld, K-P; et al. J. Clin. Microbiol. 2002, 40(7), 2431).
Kisilevsky, R.; Crandall, I.; Szarek, W. A.; Bhat, S.; Tan, C.; Boudreau, L.; Kain, K. C. Antimicrob Agents Chemother 2002, 46(8), 2619.
Lee, L. A.; Evans, R.; Wheeler, J. W. J. Org. Chem. 1972, 37, 343-347.
Lobo, C. A.; de Frazao, K.; Rodriguez, M.; Reid, M. ;Zalis, M.; Lustigman, S. Infect Immun 2004, 72(10), 5886.
Makler, M. T.; Ries, J. M.; Williams, J. A.; Bancroft, J. E.; Piper, R. C.; Gibbins, B. L.; Hinrichs, D. J. Am J Trop Med Hyg 1993, 48(6), 739).
Oh, S. S.; Chishti, A. H. Curr Top Microbiol Immunol 2005, 295, 203.
Owen, C. P.; Patel, C. H.; Dhanani, S.; Ahmed, S. Letters in Drug Design & Discovery 2006, 3, 761-765.
Owen, C. P.; Dhanani, S.; Patel, C. H.; Shahid, I.; Ahmed, S. Biorg. Med. Chem. Lett. 2006, 16, 4011-4015.
Pasvol, G.;Wainscoat, J. S.;Weatherall, D. J. Nature 1982, 297(5861), 64).

(Continued)

*Primary Examiner* — Susannah Chung
(74) *Attorney, Agent, or Firm* — Bereskin & Parr LLP/S.E.N.C.R.L., s.r.l.; Michael Fenwick

(57) ABSTRACT

The present disclosure relates to certain new and known triazolium and/or imidazolium salts and to their therapeutic use, for example in methods of treating or preventing an infection by a *Plasmodium* or *Babesia* parasite in a subject in need thereof. The triazolium and imidazolium salts are compounds of the Formula (I) or (II): wherein $R^1$-$R^4$, $R^{1'}$-$R^{3'}$, $R^8$-$R^{11}$, X, X', X'', Y, Y' and Y'' are as defined in the disclosure.

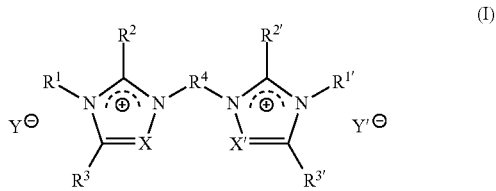

9 Claims, 2 Drawing Sheets

(56) References Cited

OTHER PUBLICATIONS

Pasvol, G. Trends Parasitol 2003, 19(10), 430).
Prudhomme, J. G.; Sherman, I. W. J Immunol Methods 1999, 229(1-2), 169).
Smilkstein, M. et al. Antimicrob. Agents. Chemother. 2004, 48(5), 1803.
Starikova, O. V.; Dolgushin, G. V.; Larina, L. I.; Ushakov, P. E.; Komarova, T. N.; Lopyrev, V. A. Russ. J. Org. Chem. 2003, 39, 1467-1470.
Trager, W.; Jensen, J. Science 1976, 193, 673.
Vlahakis, J. Z.; Kinobe, R.T.; Nakatsu, K.; Szarek, W.A.; Crandall, I.E. Anti-Plasmodium activity of imidazole—dioxolane compounds. Bioorganic & Medicinal Chemistry Letters 2006, 16, 2396-2406.
Wkly Epidemiol Rec 1997, 72(37), 277.
J White, F Nosten, S Looareesuwan, W M Watkins, K Marsh, R W Snow, G Kokwaro, J Ouma, T T Hien, M E Molyneux, T E Taylor, C I Newbold, T K Ruebush II, M Danis, B M Greenwood, R M Anderson, P Olliaro. The Lancet 1999, 353(9168), 1965 Wheeler, J.W. J. Org. Chem. 1972, 37:343-347.
Yokoyama, N.; Okamura, M. Igarashi, I., Veterinary Parasitology, 2006, 138, 22.

* cited by examiner

TRIAZOLIUM AND IMIDAZOLIUM SALTS AND USES THEREOF

This application is a national phase entry of PCT/CA2009/001224, filed Sep. 4, 2009, which claims priority from U.S. Provisional patent application Ser. No. 61/094,536 filed Sep. 5, 2008, each of these applications being incorporated herein in their entirety by reference.

The present disclosure relates to new and known triazolium and imidazolium salts and their medical use, in particular for the treatment and prevention of a parasite infection in a subject, wherein the parasite is a *Plasmodium* or other similar parasite, such as a *Babesia* parasite.

BACKGROUND OF THE DISCLOSURE

The number of people who are at risk of acquiring malaria is not precisely known, however some estimates run as high as 3.2 billion people with up to 500 million clinical cases per year (Breman, J. G.; Egan, A.; Keusch, G. T. *Am J Trop Med Hyg* 2001, 64(1-2 Suppl), iv). Further, malaria contributes to the deaths of 1-3 million people per year (*Wkly Epidemiol Rec* 1997, 72(37), 277), most of them young children. The continued spread of resistance to antimalarials such as chloroquine (White, N. J.; Nosten, F.; Looareesuwan, S.; Watkins, W. M.; Marsh, K.; Snow, R. W.; Kokwaro, G.; Ouma, J.; Hien, T. T.; Molyneux, M. E.; Taylor, T. E.; Newbold, C. I.; Ruebush, T. K., 2nd; Danis, M.; Greenwood, B. M.; Anderson, R. M.; Olliaro, P. *Lancet* 1999, 353(9168), 1965) has produced a desperate need for safe and inexpensive anti-malarial agents with novel mechanisms of action. Previous work demonstrated that small sulfonated compounds inhibited the entry of merozoites of *P. falciparum* into human erythrocytes, and were also able to suppress the replication of *P. berghei* in mice (Kisilevsky, R.; Crandall, I.; Szarek, W. A.; Bhat, S.; Tan, C.; Boudreau, L.; Kain, K. C. *Antimicrob Agents Chemother* 2002, 46(8), 2619). The interactions between a merozoite and an erythrocyte that are responsible for the invasion process are complex (Pasvol, G. *Trends Parasitol* 2003, 19(10), 430); however individual *Plasmodium* species are frequently limited to a particular host, or even a particular stage of development of an erythrocyte, by the specificity of the ligand/receptor interactions involved in erythrocyte invasion (Pasvol, G.; Wainscoat, J. S.; Weatherall, D. J. *Nature* 1982, 297(5861), 64). The invasion process is rapid—typically 15-30 seconds (Barnwell, J. W.; Galinski, M. R. Invasion of Vertebrate Cells: Erythrocytes. In: Sherman I W, ed. Malaria: Parasite Biology, Pathogenesis, and Protection. Washington, D.C.: ASM Press, 1998: 93-123), and is divided frequently into three stages: 1) the initial attachment of the merozoite to the erythrocyte followed by reorientation of the merozoite such that its apical end is proximal to the erythrocyte; 2) the secretion and anchoring of proteins required to form a "tight junction" with the erythrocyte membrane; and 3) physical insertion (Oh, S. S.; Chishti, A. H. *Curr Top Microbiol Immunol* 2005, 295, 203). While the receptors required for tight junction formation are reasonably well characterized (Lobo, C. A.; de Frazao, K.; Rodriguez, M.; Reid, M.; Zalis, M.; Lustigman, S. *Infect Immun* 2004, 72(10), 5886) the identities of the molecules responsible for the initial contact events are less clear.

*Babesia*, which belong to the hematozoan class is similar to *Plasmodium* and are a particularly important class of animal and human parasites. *Babesia* usually cause animal disease, mainly infecting cattle and dogs. *Babesia* parasites are also known to infect humans (Hunfeld, K-P; et al. *J. Clin. Microbiol.* 2002, 40(7), 2431). The invasion of an erythrocyte by *Babesia* parasites is similar to that by *Plasmodium* species (Yokoyama, N.; Okamura, M. Igarashi, I., *Veterinary Parasitology,* 2006, 138, 22). Accordingly, agents that block the invasion of *Plasmodium* parasites are expected to also block the invasion of *Babesia* parasites.

A series of tetrazolium salts have been shown to have antimalarial activity (Cui, X., J. Z. Vlahakis, I. E. Crandall, and W. A. Szarek. 2008. Anti-*Plasmodium* activity of tetrazolium salts. Bioorg Med Chem 16:1927-1947).

A series of thiazolium salts have been shown to have antimalarial activity (Hamzé, A. et al. *J. Med. Chem.* 2005, 48, 3643).

SUMMARY OF THE DISCLOSURE

The anti-*Plasmodium* activity of known and novel triazolium and imidazolium salts was evaluated and it was observed that these compounds inhibited *P. falciparum* cultures. The present series of compounds do not possess the problem of reduction associated with the previously reported tetrazolium compounds (reduction of the tetrazolium ring forms an inactive acyclic formazan). Further, the new triazolium and imidazolium ring structures have provided drug candidates possessing surprisingly greater selectivity than the tetrazolium compounds. The triazolium and imidazolium compounds are ideally suited to development as antimalarial agents for any market as they can, in most cases, be easily synthesized using 1 or 2 step reaction pathways, have no stereogenic centres, are inherently stable, and can be synthesized using low-cost reagents. The solubility of these compounds is also advantageous as many members are water or alcohol soluble and cross membranes easily. Therefore, the triazolium and imidazolium compounds of the present disclosure form the basis for a novel class of antimalarial therapeutics.

Accordingly, the present disclosure includes a method of treating or preventing an infection by a *Plasmodium* or *Babesia* parasite comprising administering to a subject in need thereof, an effective amount of one or more compounds selected from a compound of Formula I, and pharmaceutically acceptable salts, solvates, and prodrugs thereof:

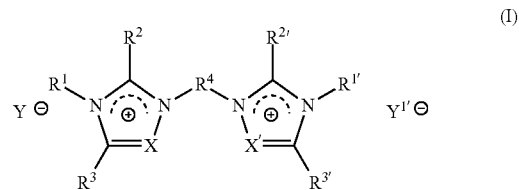

(I)

wherein, $R^1$ and $R^{1'}$ are independently selected from $C_{1-20}$alkyl, $C_{3-20}$cycloalkyl, $C_{6-14}$aryl and $C_{1-20}$alkylene-$C_{6-14}$aryl, where each $C_{1-20}$alkyl, $C_{3-20}$cycloalkyl and $C_{1-20}$alkylene is, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, =O, =S, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, $SC_{1-6}$ alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$;

$R^2$ and $R^{2'}$ are independently selected from H, $C_{1-6}$alkyl, $C_{3-10}$cycloalkyl and $C_{6-14}$aryl, where each $C_{1-6}$alkyl, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$ and $C(O)R^5$;

$R^3$ and $R^{3'}$ are independently selected from H, $C_{1-6}$alkyl, $OC_{1-6}$alkyl, $SC_{1-6}$alkyl, $NHC_{1-6}$alkyl, $N(C_{1-6}$alkyl$)(C_{1-6}$alkyl$)$, $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$, or $R^1$ and $R^3$ and/or $R^{1'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$;

$R^4$ is selected from $C_{10-20}$alkylene, $(C_{6-10}$arylene$)_p$, $C_{1-10}$alkylene-$(C_{6-10}$arylene$)_p$, $(C_{6-10}$arylene$)_p$-$C_{1-10}$alkylene, $C_{1-10}$alkylene-$(C_{6-10}$arylene$)_p$-$C_{1-10}$alkylene and $(C_{6-10}$arylene$)$-$C_{1-10}$alkylene-$(C_{6-10}$arylene$)$, wherein each $C_{10-20}$alkylene and $C_{1-10}$alkylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, =O, =S and $C(O)R^5$, and/or one or more carbon atoms are optionally replaced with a heteroatom independently selected from O, S and $NR^6$, and each $C_{6-10}$arylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$ and $C(O)R^5$;

$R^5$ is selected from H, OH, SH, $C_{1-6}$alkyl, $C_{3-10}$cycloalkyl, $C_{6-14}$aryl, $SC_{1-6}$alkyl, $OC_{3-10}$cycloalkyl, $SC_{3-10}$cycloalkyl, $OC_{6-14}$aryl, $SC_{6-14}$aryl, $C_{1-4}$alkylene$C_{6-14}$aryl, $NH_2$, $NH(C_{1-6}$alkyl$)$ and $N(C_{1-6}$alkyl$)(C_{1-6}$alkyl$)$;

$R^6$ is selected from H and $C_{1-4}$alkyl;

p is 1 or 2;

X is selected from C—$R^7$ and N;

X' is selected from C—$R^{7'}$ and N $R^7$ and $R^{7'}$ are independently selected from H, $C_{1-6}$alkyl, $OC_{1-6}$alkyl, $SC_{1-6}$alkyl, $NHC_{1-6}$alkyl, $N(C_{1-6}$alkyl$)(C_{1-6}$alkyl$)$, $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$, or $R^7$ and $R^3$ and/or $R^{7'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$; and $Y^-$ and $Y^{'-}$ are, independently, a counter anion.

The present disclosure also includes a method of treating or preventing an infection by a *Plasmodium* or *Babesia* parasite comprising administering to a subject in need thereof, an effective amount of one or more compounds selected from a compound of Formula II, and pharmaceutically acceptable salts, solvates, and prodrugs thereof:

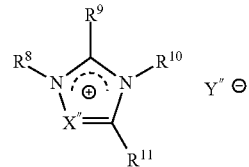

(II)

wherein, $R^8$ and $R^{10}$ are independently selected from $C_{1-20}$alkyl, $C_{6-14}$aryl, $C_{3-20}$cycloalkyl and $C_{1-20}$alkylene-$C_{6-14}$aryl, where each $C_{1-20}$alkyl, $C_{3-20}$cycloalkyl and $C_{1-20}$alkylene is, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, =O, =S, $C_{6-10}$aryl, $C_{1-4}$alkylene$C_{6-10}$aryl and $C(O)R^{12}$, and/or one or more carbon atoms are optionally replaced with a heteroatom independently selected from O, S and $NR^{13}$, and each $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^{12}$;

$R^9$ is independently selected from H, $C_{1-6}$alkyl, $C_{3-10}$cycloalkyl and $C_{6-14}$aryl, where each $C_{1-6}$alkyl, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$ and $C(O)R^{12}$;

$R^{11}$ is selected from H, $C_{1-6}$alkyl, $OC_{1-6}$alkyl, $SC_{1-6}$alkyl, $NHC_{1-6}$alkyl, $N(C_{1-6}$alkyl$)(C_{1-6}$alkyl$)$, $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl), $NO_2$, $C_{6-10}$aryl, $C_{1-4}$alkylene$C_{6-10}$aryl and $C(O)R^{12}$, or $R^{10}$ and $R^{11}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl), $NO_2$, $C_{6-10}$aryl, $C_{1-4}$alkylene$C_{6-10}$aryl and $C(O)R^{12}$;

$R^{12}$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$ cycloalkyl, $OC_{6-14}$aryl, $SC_{6-14}$aryl, $C_{1-4}$alkylene$C_{6-14}$ aryl, $NH_2$, $NH(C_{1-6}$alkyl) and $N(C_{1-6}$alkyl$)(C_{1-6}$alkyl);

$R^{13}$ is selected from H and $C_{1-4}$alkyl;

X" is selected from C—$R^{14}$ and N;

$R^{14}$ is selected from H, $C_{1-6}$alkyl, $OC_{1-6}$alkyl, $SC_{1-6}$alkyl, $NHC_{1-6}$alkyl, $N(C_{1-6}$alkyl$)(C_{1-6}$alkyl), $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl), $NO_2$, $C_{6-10}$aryl, $C_{1-4}$alkylene$C_{6-10}$aryl and $C(O)R^{12}$, or $R^{14}$ and $R^8$ are joined to form, together with the atoms to which they are attached, a monocyclic or bicyclic ring, where the ring is saturated, unsaturated or aromatic and is unsubstituted or substituted one or substituents independently selected from halo, $C_{1-6}$alkyl, $OC_{1-6}$alkyl, $SC_{1-6}$ alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl), $NO_2$, $C_{6-10}$aryl, $C_{1-4}$alkylene$C_{6-10}$aryl and $C(O)R^{12}$, or $R^{14}$ and $R^{11}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl), $NO_2$, $C_{6-10}$aryl, $C_{1-4}$alkylene$C_{6-10}$aryl and $C(O)R^{12}$; and Y"⁻ is a counter anion.

In further embodiments, the present disclosure includes a use of one or more compounds selected from a compound of Formula I and II as defined above, and pharmaceutically acceptable salts, solvates, and prodrugs thereof, for the prevention or treatment of an infection by a *Plasmodium* or *Babesia* parasite as well as a use of one or more compounds selected from a compound of Formula I and II as defined above, and pharmaceutically acceptable salts, solvates, and prodrugs thereof, for the preparation of a medicament for the prevention or treatment of an infection by a *Plasmodium* or *Babesia* parasite.

The present disclosure further includes a method of preventing or treating an invasion of a *Plasmodium* or *Babesia* parasite into an erythrocyte comprising administering to the erythrocyte an effective amount of one or more compounds selected from a compound of Formula I and II as defined above, and pharmaceutically acceptable salts, solvates, and prodrugs thereof.

The present disclosure also includes a use of one or more compounds selected from a compound of Formula I and II as defined above, and pharmaceutically acceptable salts, solvates, and prodrugs thereof, to prevent or treat an invasion of a *Plasmodium* or *Babesia* parasite into an erythrocyte as well as a use of one or more compounds selected from a compound of Formula I and II as defined above, and pharmaceutically acceptable salts, solvates, and prodrugs thereof, to prepare a medicament to prevent or treat an invasion of a *Plasmodium* or *Babesia* parasite into an erythrocyte.

According to another aspect of the present disclosure, there is included a pharmaceutical composition for the treatment or prevention of an infection by a *Plasmodium* or *Babesia* parasite comprising an antimalarial effective amount of one or more compounds selected from a compound of Formula I and II as defined above, and pharmaceutically acceptable salts, solvates, and prodrugs thereof, and a pharmaceutically acceptable carrier or diluent. In a further aspect of the present disclosure, there is included a pharmaceutical composition for the treatment of prevention of an invasion of a *Plasmodium* or *Babesia* parasite into an erythrocyte comprising an antimalarial effective amount of one or more compounds selected from a compound of Formula I and II as defined above, and pharmaceutically acceptable salts, solvates, and prodrugs thereof, and a pharmaceutically acceptable carrier or diluent.

Also included within the present disclosure is a compound selected from a compound of Formula I and II as defined above, and pharmaceutically acceptable salts, solvates, and prodrugs thereof, for use as a medicament, in particular for the prevention or treatment of an infection by a *Plasmodium* or *Babesia* parasite or the prevention or treatment of an invasion of a *Plasmodium* or *Babesia* parasite into an erythrocyte.

In a particular embodiment of the present disclosure, there are included novel compounds of Formula Ia wherein X is N. Accordingly, the present application includes a compound selected from a compound of Formula Ia, and pharmaceutically acceptable salts, solvates and prodrugs thereof:

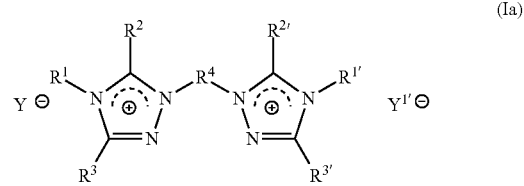

(Ia)

wherein, $R^1$ and $R^{1'}$ are independently selected from $C_{1-20}$alkyl, $C_{3-20}$cycloalkyl, $C_{6-14}$aryl and $C_{1-20}$alkylene-$C_{6-14}$aryl, where each $C_{1-20}$alkyl, $C_{3-20}$cycloalkyl and $C_{1-20}$alkylene is, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl), $NO_2$, =O, =S, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, $SC_{1-6}$ alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$;

$R^2$ and $R^{2'}$ are independently selected from H, $C_{1-6}$alkyl, $C_{3-10}$cycloalkyl and $C_{6-14}$aryl, where $C_{1-6}$alkyl, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$ and $C(O)R^5$;

$R^3$ and $R^{3'}$ are independently selected from H, $C_{1-6}$alkyl, $OC_{1-6}$alkyl, $SC_{1-6}$alkyl, $NHC_{1-6}$alkyl, $N(C_{1-6}alkyl)(C_{1-6}alkyl)$, $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$, or $R^1$ and $R^3$ and/or $R^{1'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$;

$R^4$ is selected from $C_{10-20}$alkylene, $(C_{6-10}arylene)_p$, $C_{1-10}$alkylene-$(C_{6-10}arylene)_p$, $(C_{6-10}arylene)_p$-$C_{1-10}$alkylene, $C_{1-10}$alkylene-$(C_{6-10}arylene)_p$-$C_{1-10}$alkylene and $(C_{6-10}arylene)$-$C_{1-10}$alkylene-$(C_{6-10}arylene)$, wherein each $C_{10-20}$alkylene and $C_{1-10}$alkylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $=O$, $=S$ and $C(O)R^5$, and/or one or more carbon atoms are optionally replaced with a heteroatom independently selected from O, S and $NR^6$, and each $C_{6-10}$arylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$ and $C(O)R^5$;

$R^5$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$ cycloalkyl, $OC_{6-14}$aryl, $SC_{6-14}$aryl, $C_{1-4}$alkylene$C_{6-14}$ aryl, $NH_2$, $NH(C_{1-6}alkyl)$ and $N(C_{1-6}alkyl)(C_{1-6}alkyl)$;

$R^6$ is selected from H and $C_{1-4}$alkyl;

p is 1 or 2;

and $Y^-$ and $Y^{1-}$ are, independently, a counter anion, with the proviso that when $R^4$ is $C_{12}$alkylene and $R^2$, $R^{2'}$, $R^3$ and $R^{3'}$ are all $CH_3$, then $R^1$ and $R^{1'}$ are not both $C_{10}$alkyl.

In a further particular embodiment of the present disclosure, there are included novel compounds of Formula Ib wherein X is N and $R^2$, $R^{2'}$, $R^3$ and $R^{3'}$ are H. Accordingly, the present application includes a compound selected from a compound of Formula Ib, and pharmaceutically acceptable salts, solvates and prodrugs thereof:

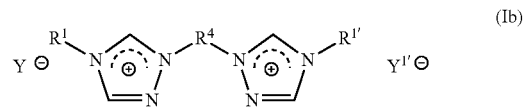

(Ib)

$R^1$ and $R^{1'}$ are independently selected from $C_{1-20}$alkyl, $C_{3-20}$cycloalkyl, $C_{6-14}$aryl and $C_{1-20}$alkylene-$C_{6-14}$aryl, where each $C_{1-20}$alkyl, $C_{3-20}$cycloalkyl and $C_{1-20}$alkylene is, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $=O$, $=S$, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, $SC_{1-6}$ alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$;

$R^4$ is selected from $C_{10-20}$alkylene, $(C_{6-10}arylene)_p$, $C_{1-10}$alkylene-$(C_{6-10}arylene)_p$, $(C_{6-10}arylene)_p$-$C_{1-10}$alkylene, $C_{1-10}$alkylene-$(C_{6-10}arylene)_p$-$C_{1-10}$alkylene and $(C_{6-10}arylene)$-$C_{1-10}$alkylene-$(C_{6-10}arylene)$, wherein each $C_{10-20}$alkylene and $C_{1-10}$alkylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $=O$, $=S$ and $C(O)R^5$, and/or one or more carbon atoms are optionally replaced with a heteroatom independently selected from O, S and $NR^6$, and each $C_{6-10}$arylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$ and $C(O)R^5$;

$R^5$ is selected from H, OH, SH, $C_{3-10}$cycloalkyl, $C_{6-14}$aryl, $OC_{1-6}$alkyl, $SC_{1-6}$alkyl, $OC_{3-10}$cycloalkyl, $SC_{3-10}$cycloalkyl, $OC_{6-14}$aryl, $SC_{6-14}$aryl, $C_{1-4}$alkylene$C_{6-14}$aryl, $NH_2$, $NH(C_{1-6}alkyl)$ and $N(C_{1-6}alkyl)(C_{1-6}alkyl)$;

$R^6$ is selected from H and $C_{1-4}$alkyl;

p is 1 or 2; and $Y^-$ and $Y^{1-}$ are, independently, a counter anion.

In another particular embodiment of the present disclosure, there are included novel compounds of Formula Ic wherein $R^4$ comprises a bi-phenyl group. Accordingly, the present application includes a compound selected from a compound of Formula Ic, and pharmaceutically acceptable salts, solvates and prodrugs thereof:

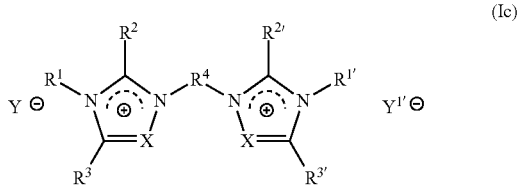

(Ic)

R¹ and R¹' are independently selected from $C_{1-20}$alkyl, $C_{3-20}$cycloalkyl, $C_{6-14}$aryl and $C_{1-20}$alkylene-$C_{6-14}$aryl, where each $C_{1-20}$alkyl, $C_{3-20}$cycloalkyl and $C_{1-20}$alkylene is, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, =O, =S, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$;

$R^2$ and $R^{2'}$ are independently selected from H, $C_{1-6}$alkyl, $C_{3-10}$cycloalkyl and $C_{6-14}$aryl, where each $C_{1-6}$alkyl, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$ and $C(O)R^5$;

$R^3$ and $R^{3'}$ are independently selected from H, $C_{1-6}$alkyl, $OC_{1-6}$alkyl, $SC_{1-6}$alkyl, $NHC_{1-6}$alkyl, $N(C_{1-6}$alkyl)($C_{1-6}$alkyl), $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl or $C_{6-14}$aryl, is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$, or $R^1$ and $R^3$ and/or $R^{1'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$;

$R^4$ is selected from biphenylene, $CH_2$-biphenylene, biphenylene-$CH_2$, $CH_2$-biphenylene-$CH_2$, where each biphenylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$ and $C(O)R^5$;

$R^5$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$ cycloalkyl, $OC_{6-14}$aryl, $SC_{6-14}$aryl, $C_{1-4}$alkylene$C_{6-14}$ aryl, $NH_2$, $NH(C_{1-6}$alkyl) and $N(C_{1-6}$alkyl)($C_{1-6}$alkyl);

$R^6$ is selected from H and $C_{1-4}$alkyl;

p is 1 or 2;

X is selected from C—$R^7$ and N;

X' is selected from C—$R^{7'}$ and N $R^7$ and $R^{7'}$ are independently selected from H, $C_{1-6}$alkyl, $OC_{1-6}$alkyl, $SC_{1-6}$alkyl, $NHC_{1-6}$alkyl, $N(C_{1-6}$alkyl)($C_{1-6}$alkyl), $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$, or $R^7$ and $R^3$ and/or $R^{7'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$; and $Y^-$ and $Y^{1-}$ are, independently, a counter anion, with the proviso that, when $R^4$ is $CH_2$-biphenylene-$CH_2$, $R^1$ is not $CH_2$Ph.

In another particular embodiment of the present disclosure, there is included certain novel compounds of Formula II. Accordingly, the present application includes a compound selected from a compound of Formula IIa, and pharmaceutically acceptable salts, solvates and prodrugs thereof

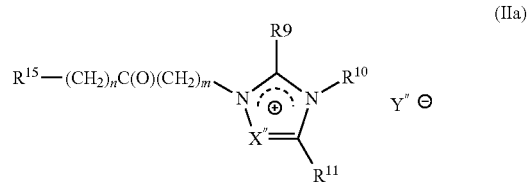

(IIa)

wherein:

$R^9$ is selected from H and phenyl, $R^{10}$ is selected from $C_{1-6}$alkyl;

$R^{11}$ and $R^{15}$ are independently selected from $C_{6-14}$aryl which is unsubstituted or substituted with one or more substituents, independently selected from halo, $C_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$ and $C(O)R^{12}$;

$R^{12}$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$ cycloalkyl, $OC_{6-14}$aryl, $SC_{6-14}$aryl, $NH_2$, $NH(C_{1-6}$alkyl) and $N(C_{1-6}$alkyl)($C_{1-6}$alkyl);

n is 0, 1, 2, 3 or 4;

m is 1, 2, 3 or 4;

X" is selected from C—R$^{14}$ and N;

R$^{14}$ is selected from H, C$_{1-10}$alkyl, C$_{3-10}$cycloalkyl and C$_{6-10}$aryl, where each C$_{1-6}$alkyl, C$_{3-10}$cycloalkyl, and C$_{6-14}$aryl are unsubstituted or substituted with one or more substituents independently selected from halo, C$_{1-6}$alkyl, OC$_{1-6}$alkyl, SC$_{1-6}$alkyl, fluoro-substituted C$_{1-6}$alkyl, fluoro-substituted OC$_{1-6}$alkyl, fluoro-substituted SC$_{1-6}$alkyl, OH, SH, CN, NH$_2$, NHC$_{1-6}$alkyl, N(C$_{1-6}$alkyl)(C$_{1-6}$alkyl), NO$_2$ and C(O)R$^{12}$; and Y"$^-$ is a counter anion.

The present disclosure further includes a pharmaceutical composition comprising one or more compounds selected from a compound of Formula Ia, Ib, Ic and IIa as defined above, and pharmaceutically acceptable salts, solvates, and prodrugs thereof, and a pharmaceutically acceptable carrier and/or diluent.

The present disclosure also includes one or more compounds selected from a compound of Formula Ia, Ib, Ic and IIa as defined above, and or pharmaceutically acceptable salts, solvates, and/or prodrugs thereof, for use as a medicament.

Also included in the present disclosure is one or more compounds of Formula Ia, Ib, Ic or IIa as defined above, and/or pharmaceutically acceptable salts, solvates, and/or prodrugs thereof, for use to prevent or treat an infection by a *Plasmodium* or *Babesia* parasite as well as a use of one or more compounds of Formula Ia, Ib, Ic or IIa as defined above, and/or pharmaceutically acceptable salts, solvates, and/or prodrugs thereof, for use to prevent or treat an invasion of a *Plasmodium* or *Babesia* parasite into an erythrocyte.

Also included in the present disclosure is one or more compounds of Formula Ia, Ib, Ic or IIa as defined above, and/or pharmaceutically acceptable salts, solvates, and/or prodrugs thereof, for use to prepare a medicament to prevent or treat an infection by a *Plasmodium* or *Babesia* parasite as well as a use of one or more compounds of Formula Ia, Ib, Ic or IIa as defined above, and/or pharmaceutically acceptable salts, solvates, and/or prodrugs thereof, for use to prepare a medicament to prevent or treat an invasion of a *Plasmodium* or *Babesia* parasite into an erythrocyte.

In an embodiment of the disclosure, the parasite is a *Plasmodium* parasite and the methods and uses are directed to the prevention and treatment of malaria in a subject in need thereof.

In a further embodiment of the present disclosure there is also included a compound selected from QT72, QT74, QT75, QT76, QT78, QT79, QT80, QT81, QT82, QT83, QT84, QT92, QT93, QT95, QT97, QT99, QT101, QT107, QT109, QT114, QT116, QT118, QT119 and QT123 as shown in Table 1, and pharmaceutically acceptable salts, solvates, and/or prodrugs thereof.

The present disclosure further includes a pharmaceutical composition comprising one or more compounds selected from QT72, QT74, QT75, QT76, QT78, QT79, QT80, QT81, QT82, QT83, QT84, QT92, QT93, QT95, QT97, QT99, QT101, QT107, QT109, QT114, QT116, QT118, QT119 and QT123 as shown in Table 1, and pharmaceutically acceptable salts, solvates, and/or prodrugs thereof, and a pharmaceutically acceptable carrier and/or diluent.

The present disclosure also includes one or more compounds selected from QT72, QT74, QT75, QT76, QT78, QT79, QT80, QT81, QT82, QT83, QT84, QT92, QT93, QT95, QT97, QT99, QT101, QT107, QT109, QT114, QT116, QT118, QT119 and QT123 as shown in Table 1, and pharmaceutically acceptable salts, solvates, and/or prodrugs thereof, for use as a medicament.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the drawings in which.

DETAILED DESCRIPTION OF THE DISCLOSURE

I. Definitions

Figure 1:
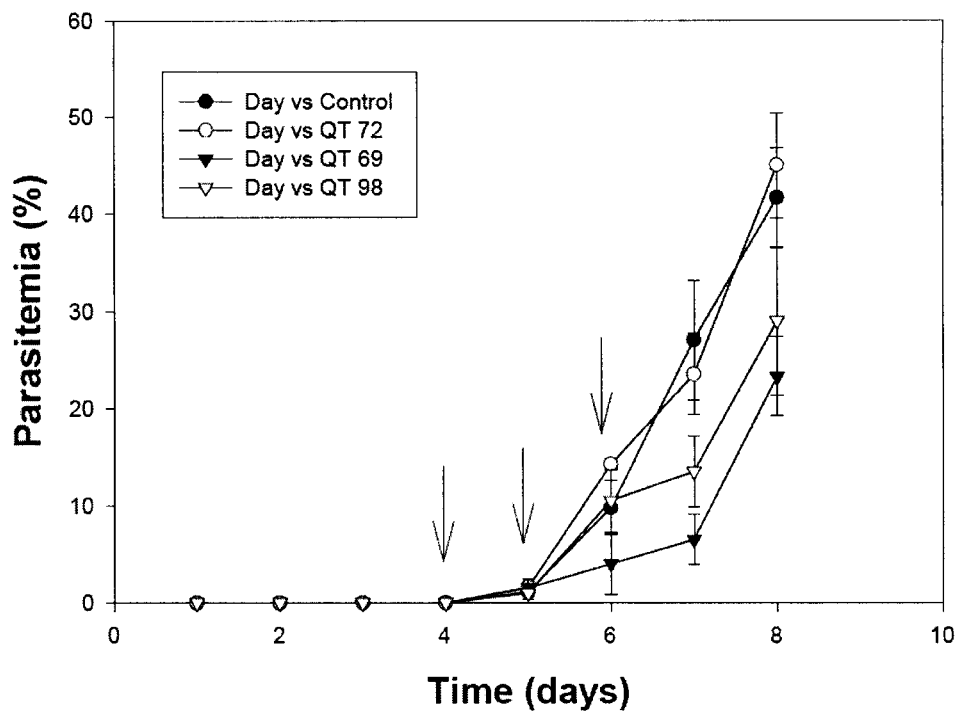
FIG. 1 shows graphs depicting the effects of certain compounds of the disclosure on parasitemias in mice infected with 10$^6$ *P. berghi* parasites i.p.
Figure 1:
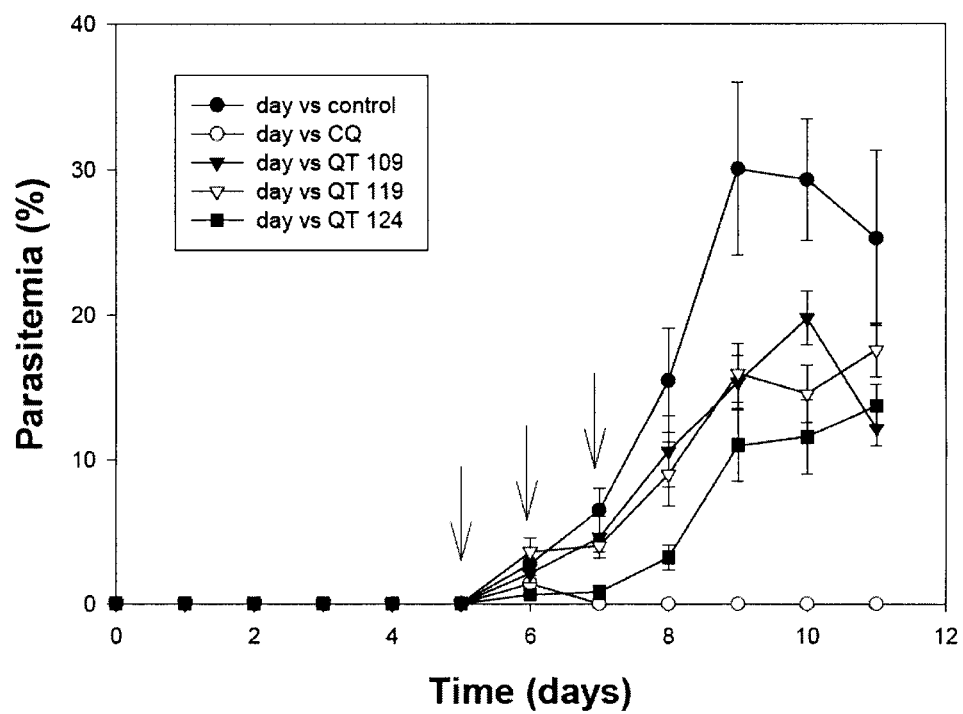

The term "alkyl" as used herein means straight and/or branched chain, saturated alkyl groups and includes methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

The suffix "ene" when added to any of the claimed groups means that the group is divalent (i.e. attached at each of two points by another group).

The term "aryl' as used herein means a monocyclic or polycyclic carbocycle that contains at least one aromatic ring and includes phenyl, naphthyl and indanyl and the like.

The term "cycloalkyl" as used herein means a monocyclic or polycyclic saturated carbocycle and includes cyclopropyl, cyclobutyl, cyclopentyl, cyclohexyl, cycloheptyl, cyclooctyl, cyclododecyl, adamantanyl and the like.

The term "polycyclic" as used herein means a group that contains more than one ring linked together and includes, for example, groups that contain two (bicyclic), three (tricyclic) or four (quadracyclic) rings. The rings may be linked through a single bond, a single atom (spirocyclic) or through two atoms (fused and bridged).

The term "biphenylene" as used herein refers to the a group of the following formula:

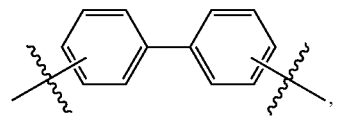

suitably of the formula:

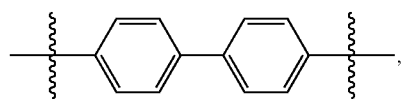

which is unsubstituted or, where specified, substituted.

The term "halo" or "halogen atom" means chloro, fluoro, bromo or iodo.

The term "substituted with one or more substituents" as used herein means that one or all of the substitutable hydrogens on the referred-to group is replaced with one of the substituents provided in the list of substituents for that group.

The term "fluoro-substituted" as used herein means that one or more, including all, of the hydrogen atoms on the referred-to group is replaced with fluorine. For example, fluoro-substituted alkyl includes $CF_3$, $CHF_2$, $CH_2CF_3$, $CF_2CF_3$ and $CF_2CF_2CF_3$, and fluoro-substituted aryl includes $C_6F_5$.

The term "unsaturated" as used herein means that the referenced group has one or more double bonds, suitably one, two or three double bonds, more suitable one or two double bonds.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the disclosure will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the present disclosure may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine). Some common esters which have been utilized as prodrugs are phenyl esters, aliphatic ($C_1$-$C_{24}$) esters, acyloxymethyl esters, carbamates and amino acid esters.

The term "compound(s) of the disclosure" or "compound(s) of the present disclosure" as used herein means a compound(s) of Formula I, II, Ia, Ib, Ic or IIa, or salts, solvates or prodrugs thereof.

The term "pharmaceutically acceptable" means compatible with the treatment of patients.

The term "pharmaceutically acceptable acid addition salt" as used herein means any non-toxic organic or inorganic salt of any base compound of the disclosure, or any of its intermediates. The compounds of the disclosure are all in the salt form, that is they all contain at least one positive charge and, therefore at least one counter anion. The counter anion(s) ($Y^-$, $Y'^-$ and $Y''^-$) may be any suitable anion for example, but not limited to, halides (iodide, chloride, bromide or fluoride), sulfates, formates, acetates, alkylsulfonates, aryl sulfonates, borates and phosphates. Other basic functionalities in compounds of the disclosure may also form an acid addition salt including, for example, those having a basic nitrogen, such as an $NH_2$, NHalkyl or N(alkyl)$_2$. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Such salts may exist in either a hydrated, solvated or substantially anhydrous form. The selection of the appropriate salt will be known to one skilled in the art. Other non-pharmaceutically acceptable salts, e.g. oxalates, may be used, for example, in the isolation of the compounds of the disclosure, for laboratory use, or for subsequent conversion to a pharmaceutically acceptable acid addition salt.

The formation of a desired compound salt is achieved using standard techniques. For example, the neutral compound is treated with an acid or base in a suitable solvent and the formed salt is isolated by filtration, extraction or any other suitable method.

The term "malaria" as used herein refers to an infectious disease, also known as ague or marsh fever, typically caused by a protistan parasite of the genus *Plasmodium*, suitably, *P. falciparum, P. virax, P. ovale, P. berghei, P. chabaudi chabaudi, P. malariae* or *P. knowlesi*. This parasite is transmitted primarily by female *Anopheles* mosquitoes. *Plasmodium* invades and consumes the red blood cells, or erythrocytes, of its hosts, which leads to symptoms including fever, anemia, and in severe cases, a coma potentially leading to death.

The term "*Babesia*" as used herein refers to a protozoan from the phylum Apicomplexa. Examples of *Babesia* parasites include, for example, *Babesia bovis, Babesia bigemina, Babesia divergens, Babesia canis, Babesia cabaffi* and *Babesia ovis*.

The term a "therapeutically effective amount", "effective amount" or a "sufficient amount" of a compound of the present disclosure is a quantity sufficient to, when administered to a cell or a subject, including a mammal, for example a human, effect beneficial or desired results, including clinical results, and, as such, an "effective amount" or synonym thereto depends upon the context in which it is being applied. For example, in the context of disease, therapeutically effective amounts of the compounds of the present disclosure are used to treat, modulate, attenuate, reverse, or affect a parasite infection in a mammal. For example, an "effective amount" is intended to mean that amount of a compound that is sufficient to treat, prevent or inhibit malaria or a disease associated with malaria. In some suitable embodiments, malaria or the disease or disorder associated with malaria is caused by a *Plasmodium* parasite, suitably, *P. falciparum, P. virax, P. ovale, P. berghei, P. chabaudi chabaudi* or *P. malariae*, thus it is the amount sufficient to, when administered to the cell or subject, including a mammal, e.g., a human, to treat, prevent or inhibit malaria or a disease or a disorder associated with malaria or a malarial parasite, e.g. *Plasmodium* parasite. In another example, an "effective amount" is intended to mean that amount of a compound that is sufficient to treat, prevent or inhibit malaria or a disease associated with babesiosis or a disease associated with babesiosis. In some suitable embodiments, babesiosis or the disease or disorder associated with babesiosis is caused by a *Babesia* parasite, including, for example, *Babesia bovis, Babesia bigemina, Babesia divergens, Babesia canis, Babesia caballi* and *Babesia ovis*, thus it is the amount sufficient to, when administered to the cell or subject, including a mammal, e.g., a human, cattle or dog, to treat, prevent or inhibit babesiosis or a disease or a disorder associated with babesiosis or a *Babesia* parasite. The amount of a given compound of the present disclosure that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present disclosure is an amount which prevents, inhibits, suppresses or reduces malaria (e.g., as determined by clinical symptoms or the amount of malarial parasites, e.g., *Plasmodium* organisms), or an amount which prevents, inhibits, suppresses or reduces babesiosis (e.g., as determined by clinical symptoms or the amount of *Babesia* parasites) in a subject as compared to a control. As defined herein, a therapeutically effective amount of a compound of the present disclosure may be readily determined by one of ordinary skill by routine methods known in the art.

In an embodiment, a therapeutically effective amount of a compound of the present disclosure is about 0.1 to about 50 mg/kg body weight, suitably about 0.5 to about 20 mg/kg body weight, more suitably, about 1.0 to about 10 mg/kg body weight and more suitably, about 2 to about 3 mg/kg body weight, per day, in single or divided doses. In another embodiment, a therapeutically effective amount of a compound of the present disclosure is about 10 mg to about 5000 mg, suitably about 30 mg to about 1500 mg, more suitably about 50 mg to about 1000 mg, more suitably about 100 mg to about 500 mg, per day, in single or divided doses. The skilled artisan will appreciate that certain factors may influence the dosage required to effectively treat a subject, or prevent a subject, from being afflicted with malaria and these factors include, but are not limited to, the severity of the disease or disorder, previous treatments, the general health and/or age of the subject and other diseases present.

Moreover, a "treatment" or "prevention" regime of a subject with a therapeutically effective amount of the compound of the present disclosure may consist of a single administration, or alternatively comprise a series of applications. For example, the compound of the present disclosure may be administered at least once a week. However, in another embodiment, the compound may be administered to the patient from about one time per week to one or more, for example one to four, times daily for a given treatment. The length of the treatment period depends on a variety of factors, such as the severity of the disease, the age of the patient, the concentration and the activity of the compounds of the present disclosure, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. The compounds of the present disclosure may be administered before, during or after exposure to malaria or malarial parasite, e.g. *Plasmodium* parasite, or after exposure to babesiosis or a *Babesia* parasite.

As used herein, "administered contemporaneously" means that two substances are administered to a subject such that they are both biologically active in the subject at the same time. The exact details of the administration will depend on the pharmacokinetics of the two substances in the presence of each other, and can include administering one substance within 24 hours of administration of the other, if the pharmacokinetics are suitable. Design of suitable dosing regimens are routine for one skilled in the art. In particular embodiments, two substances will be administered substantially simultaneously, i.e. within minutes of each other, or in a single composition that comprises both substances.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with malaria or manifesting a symptom associated with malaria or a reduction in the risk or probability of a malaria parasite invading an erythrocyte.

The term "subject" as used herein includes all members of the animal kingdom including human, dogs, cattle and other livestock. The subject is suitably a human.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The definitions and embodiments described in particular sections are intended to be applicable to other embodiments herein described for which they are suitable as would be understood by a person skilled in the art.

II. Methods and uses of the Disclosure

The activity of several triazolium and imidazolium salts in both human and mouse *Plasmodium* cultures showed that these compounds have anti-*Plasmodium* activity and further suggests that these compounds interact with a component of the parasite that is both essential and conserved. Several compounds were active in the nM range with 4 to 6 log differences in the relative activities in *P. falciparum* and CHO cell cultures.

Accordingly, the present disclosure includes a method of treating or preventing an infection by a *Plasmodium* or *Babesia* parasite comprising administering to a subject in need thereof, an effective amount of one or more compounds selected from a compound of Formula I, and pharmaceutically acceptable salts, solvates, and prodrugs thereof:

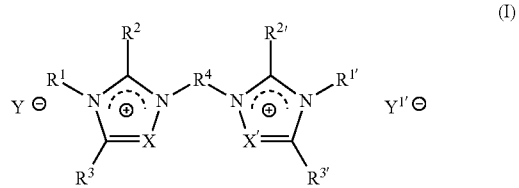

(I)

wherein, $R^1$ and $R^{1'}$ are independently selected from $C_{1-20}$alkyl, $C_{3-20}$cycloalkyl, $C_{6-14}$aryl and $C_{1-20}$alkylene-$C_{6-14}$aryl, where each $C_{1-20}$alkyl, $C_{3-20}$cycloalkyl and $C_{1-20}$alkylene is, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, =O, =S, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$;

$R^2$ and $R^{2'}$ are independently selected from H, $C_{1-6}$alkyl, $C_{3-10}$cycloalkyl and $C_{6-14}$aryl, where each $C_{1-6}$alkyl, $C_{3-10}$cycloalkyl and $C_{6-14}$aryl are unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$ and $C(O)R^5$;

$R^3$ and $R^{3'}$ are independently selected from H, $C_{1-6}$alkyl, $OC_{1-6}$alkyl, $NHC_{1-6}$alkyl, $N(C_{1-6}$alkyl)($C_{1-6}$alkyl), $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$, or $R^1$ and $R^3$ and/or $R^{1'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$;

$R^4$ is selected from $C_{10-20}$alkylene, $(C_{6-10}$arylene$)_p$, $C_{1-10}$alkylene-$(C_{6-10}$arylene$)_p$, $(C_{6-10}$arylene$)_p$-$C_{1-10}$alkylene, $C_{1-10}$alkylene-$(C_{6-10}$arylene$)_p$-$C_{1-10}$alkylene and $(C_{6-10}$arylene$)$-$C_{1-10}$alkylene-$(C_{6-10}$arylene$)$, wherein each $C_{10-20}$alkylene and $C_{1-10}$alkylene are unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, =O, =S and $C(O)R^5$, and/or one or more carbon atoms are optionally replaced with a heteroatom independently selected from O, S and $NR^6$, and each $C_{6-10}$arylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$ and $C(O)R^5$;

$R^5$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$cycloalkyl, $OC_{6-14}$aryl, $SC_{6-14}$aryl, $C_{1-4}$alkylene$C_{6-14}$aryl, $NH_2$, $NH(C_{1-6}$alkyl) and $N(C_{1-6}$alkyl)($C_{1-6}$alkyl);

$R^6$ is selected from H and $C_{1-4}$alkyl;

p is 1 or 2;

X is selected from C—$R^7$ and N;

X' is selected from C—$R^{7'}$ and N $R^7$ and $R^{7'}$ are independently selected from H, $C_{1-6}$alkyl, $OC_{1-6}$alkyl, $SC_{1-6}$alkyl, $NHC_{1-6}$alkyl, $N(C_{1-6}$alkyl)($C_{1-6}$alkyl), $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$, or $R^7$ and $R^3$ and/or $R^{7'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)($C_{1-6}$alkyl), $NO_2$, $C_{6-10}$aryl, $C_{1-4}$alkylene$C_{6-10}$aryl and $C(O)R^5$; and $Y^-$ and $Y^{'-}$ are, independently, a counter anion.

In further embodiments, the present disclosure includes a use of one or more compounds selected from a compound of Formula I as defined above, and pharmaceutically acceptable salts, solvates, and prodrugs thereof, for the prevention or treatment of an infection by a *Plasmodium* or *Babesia* parasite as well as a use of one or more compounds selected from a compound of Formula I as defined above, and pharmaceutically acceptable salts, solvates, and prodrugs thereof, for the preparation of a medicament for the prevention or treatment of an infection by a *Plasmodium* or *Babesia* parasite.

The present disclosure further includes a method of preventing or treating an invasion of a *Plasmodium* or *Babesia* parasite into an erythrocyte comprising administering to the erythrocyte one or more compounds selected from a compound of Formula I as defined above, and pharmaceutically acceptable salts, solvates, and prodrugs thereof.

The present disclosure also includes a use of one or more compounds selected from a compound of Formula I as defined above, and pharmaceutically acceptable salts, solvates, and prodrugs thereof, to prevent or treat an invasion of a *Plasmodium* or *Babesia* parasite into an erythrocyte as well as a use of one or more compounds selected from a compound of Formula I as defined above, and pharmaceutically acceptable salts, solvates, and prodrugs thereof, to prepare a medicament to prevent or treat an invasion of a *Plasmodium* or *Babesia* parasite into an erythrocyte.

In an embodiment of the methods and uses of the disclosure $R^1$ and $R^{1'}$ in the compounds of Formula I are independently selected from $C_{1-10}$alkyl, $C_{3-10}$cycloalkyl, $C_{6-10}$aryl and $C_{1-10}$alkylene-$C_{6-10}$aryl, where each $C_{1-10}$alkyl and $C_{1-10}$alkylene is, independently, unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$ alkyl, OH, SH, CN, $NH_2$, $NHC_{1-4}$alkyl, $N(C_{1-4}$alkyl)$(C_{1-4}$ alkyl), $NO_2$, =O and =S and/or one to three carbon atoms are optionally replaced with a heteroatom independently selected from O, S and $NR^6$, and each $C_{6-10}$aryl is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$. In a further embodiment of the disclosure, $R^1$ and $R^{1'}$ in the compounds of Formula I are independently selected from $C_{1-4}$alkyl, phenyl and $C_{1-4}$alkylene-phenyl, where each $C_{1-4}$alkyl and $C_{1-4}$alkylene is, independently, unsubstituted or fluoro-substituted and/or substituted with one or two groups independently selected from chloro, bromo, iodo, $CH_3$, $OCH_3$, $CF_3$, $OCF_3$, OH, CN, $NH_2$, $NHCH_3$, $N(CH_3)_2$, $NO_2$ and =O and/or one or two carbon atoms are optionally replaced with O, and each $C_{6-10}$aryl is unsubstituted or fluoro-substituted and/or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$, $NO_2$ and =O. In a further embodiment of the present disclosure, $R^1$ and $R^{1'}$ in the compounds of Formula I are independently $C_{1-6}$alkyl or $C_{1-4}$alkylene-phenyl, where phenyl is unsubstituted, fluoro-substituted or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$ and $NO_2$. In a further embodiment, $R^1$ and $R^{1'}$ in the compounds of Formula I are the same and are both selected from $CH_3$, $CH_2CH_3$, $(CH_2)_2CH_3$, $CH(CH_3)_2$, $(CH_2)_3CH_3$, $CH_2CH(CH_3)_2$, $C(CH_3)_3$, $CH(CH_3)CH_2CH_3$, $CH_2$-phenyl, $CH_2$-(4-nitrophenyl), $CH_2$-(3-nitrophenyl) and $CH_2$-(2-nitrophenyl).

In another embodiment of the methods and uses of the disclosure $R^2$ and $R^{2'}$ in the compounds of Formula I are independently selected from H, $C_{1-4}$alkyl, $C_{3-6}$cycloalkyl and $C_{6-10}$aryl, where $C_{1-4}$alkyl, $C_{3-6}$cycloalkyl and $C_{6-10}$aryl are unsubstituted or fluoro-substituted and/or substituted with one to three substituents independently selected from chloro, bromo, iodo, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$. In a further embodiment $R^2$ and $R^{2'}$ in the compounds of Formula I are independently selected from H, $CH_3$, cyclopentyl, cyclohexyl and phenyl, where cyclopentyl, cyclohexyl and phenyl are unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$. In a further embodiment, $R^2$ and $R^{2'}$ in the compounds of Formula I are the same and are both selected from H and $CH_3$, suitably H.

In another embodiment of the methods and uses of the disclosure $R^3$ and $R^{3'}$ in the compounds of Formula I are independently selected from H, $C_{1-4}$alkyl, $OC_{1-4}$alkyl, $SC_{1-4}$alkyl, $NHC_{1-4}$alkyl, $N(C_{1-4}$alkyl)$(C_{1-4}$alkyl), $C_{3-6}$cycloalkyl, $OC_{3-6}$cycloalkyl, $SC_{3-6}$cycloalkyl, $C_{6-10}$aryl, $C_{1-4}$alkylene$C_{6-10}$aryl, $OC_{6-10}$aryl and $SC_{6-10}$aryl, where each $C_{1-4}$alkyl, $C_{1-4}$alkylene, $C_{3-6}$cycloalkyl and $C_{6-10}$aryl is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$. In a further embodiment $R^3$ and $R^{3'}$ in the compounds of Formula I are independently selected from H, $CH_3$, $OCH_3$, $SCH_3$, $NHCH_3$, $N(CH_3)_2$, cyclopentyl, cyclohexyl, O-cyclopentyl, O-cyclohexyl, phenyl, benzyl, O-phenyl and S-phenyl, where, each phenyl, cyclopentyl and cyclohexyl, is unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$. In a further embodiment, $R^3$ and $R^{3'}$ in the compounds of Formula I are the same and are both selected from H and $CH_3$, suitably H.

In another embodiment of the methods and uses of the disclosure, $R^1$ and $R^3$ and/or $R^{1'}$ and $R^{3'}$ in the compounds of Formula I are joined to form, together with the atoms to which they are attached, a monocyclic 5- or 6-membered ring, where the ring is unsaturated and is unsubstituted or fluoro-substituted and/or substituted with one to two substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$. In another embodiment, $R^1$ and $R^3$ and/or $R^{1'}$ and $R^{3'}$ in the compounds of Formula I are joined to form, together with the atoms to which they are attached, a monocyclic 5-membered ring, where the ring is unsaturated and is unsubstituted or substituted with one substituent selected from fluoro, chloro, bromo, iodo, $CH_3$, $OCH_3$, $CF_3$, $OCF_3$, OH, SH, CN, $NH_2$, $NHCH_3$, $N(CH_3)_2$ and $NO_2$. In another embodiment, $R^1$ and $R^3$ and $R^{1'}$ and $R^{3'}$ in the compounds of Formula I are joined to form, together with the atoms to which they are attached, a monocyclic 5-membered ring, where the ring is unsaturated and is unsubstituted.

In another embodiment of the methods and uses of the disclosure, $R^4$ in the compounds of Formula I is selected from $C_{11-17}$alkylene, (phenylene)$_p$, $C_{1-4}$alkylene-(phenylene)$_p$, (phenylene)$_p$-$C_{1-4}$alkylene, $C_{1-4}$alkylene-(phenylene)$_p$-$C_{1-4}$alkylene and phenylene-$C_{1-4}$alkylene-phenylene, wherein each alkylene is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl), $NO_2$, =O and =S and/or one to three carbon atoms are optionally replaced with a heteroatom independently selected from O, S and $NR^6$, and each phenylene is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$, and p is 1 or 2. In another embodiment, $R^4$ in the compounds of Formula I is selected from $C_{12-15}$alkylene, biphenylene, $CH_2$-biphenylene, biphenylene-$CH_2$, $CH_2$-biphenylene-$CH_2$, wherein each alkylene, is unsubstituted or fluoro-substituted and/or substituted with one to two substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$ and =O and/or one to two carbon atoms are optionally replaced with a heteroatom independently selected from O, S and $NR^6$, and each phenylene is unsubstituted or fluoro-substituted and/or substituted with one to two substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In a further embodiment of the disclosure, $R^4$ in the compounds of Formula I is selected from $C_{12-15}$alkylene and biphenylene both of which are unsubstituted. In a further embodiment of the disclosure, $R^4$ in the compounds of Formula I is selected from $C_{13}$alkylene and biphenylene both of which are unsubstituted.

In a further embodiment of the methods and uses of the present disclosure, $R^5$ in the compounds of Formula I is selected from H, OH, SH, $C_{1-4}$alkyl, $C_{3-6}$cycloalkyl, $C_{6-10}$aryl, $OC_{1-4}$alkyl, $SC_{1-4}$alkyl, $OC_{3-6}$cycloalkyl, $SC_{3-6}$cycloalkyl, $OC_{6-10}$aryl, $SC_{6-10}$aryl, $NH_2$, $NH(C_{1-4}$alkyl) and $N(C_{1-4}$alkyl)$_2$. In a further embodiment, $R^5$ in the compounds of Formula I is selected from H, OH. $CH_3$, cyclopentyl, cyclohexyl, phenyl, OCH$_3$, O-cyclopentyl, O-cyclohexyl, O-phenyl, NH$_2$, NH(CH$_3$) and N(CH$_3$)$_2$. In a further embodiment, R$^5$ in the compounds of Formula I is selected from CH$_3$, OH, OCH$_3$, NH$_2$, NH(CH$_3$) and N(CH$_3$)$_2$. In a further embodiment, R$^5$ in the compounds of Formula I is CH$_3$.

In a further embodiment of the methods and uses of the present disclosure, R$^6$ in the compound of Formula I is selected from H and CH$_3$.

In a further embodiment of the methods and uses of the present disclosure, X and X' in the compounds of Formula I are, independently, C—R$^7$.

In a further embodiment of the methods and uses of the present disclosure, X and X' in the compounds of Formula I are, independently, N.

In a further embodiment of the methods and uses of the present disclosure, R$^7$ and R$^{7'}$ in the compounds of Formula I are independently selected from H, C$_{1-6}$alkyl, C$_{3-6}$cycloalkyl and C$_{6-10}$aryl, where each C$_{1-6}$alkyl, C$_{3-6}$cycloalkyl and C$_{6-10}$aryl is unsubstituted or fluoro-substituted and/or substituted with one to three substituents independently selected from chloro, bromo, iodo, OC$_{1-4}$alkyl, fluoro-substituted C$_{1-4}$alkyl, fluoro-substituted OC$_{1-4}$alkyl, OH, SH, CN, NH$_2$, NHC$_{1-4}$alkyl, N(C$_{1-4}$alkyl)(C$_{1-4}$alkyl) and NO$_2$. In a further embodiment R$^7$ and R$^{7'}$ in the compounds of Formula I are independently selected from H, CH$_3$, cyclopentyl, cyclohexyl and phenyl, where cyclopentyl, cyclohexyl and phenyl are unsubstituted or fluoro-substituted and/or substituted with one to two substituents independently selected from CH$_3$, OCH$_3$, CF$_3$, OCF$_3$, OH, CN, NH$_2$, NHCH$_3$, N(CH$_3$)$_2$ and NO$_2$. In a further embodiment, R$^7$ and R$^{7'}$ in the compounds of Formula I are the same and are both selected from H and CH$_3$, suitably H.

In another embodiment of the methods and uses of the disclosure, R$^7$ and R$^3$ and/or R$^{7'}$ and R$^{3'}$ in the compounds of Formula I are joined to form, together with the atoms to which they are attached, a monocyclic 5- or 6-membered ring, where the ring is unsaturated or aromatic and is unsubstituted or fluoro-substituted and/or substituted with one to two substituents independently selected from chloro, bromo, iodo, fluoro-substituted C$_{1-4}$alkyl, fluoro-substituted OC$_{1-4}$alkyl, OH, SH, CN, NH$_2$, NHC$_{1-4}$alkyl, N(C$_{1-4}$alkyl)(C$_{1-4}$alkyl) and NO$_2$. In another embodiment, R$^7$ and R$^3$ and/or R$^{7'}$ and R$^{3'}$ in the compounds of Formula I are joined to form, together with the atoms to which they are attached, a monocyclic 6-membered ring, where the ring is unsaturated or aromatic and is unsubstituted or substituted with one substituent selected from fluoro, chloro, bromo, iodo, CH$_3$, OCH$_3$, CF$_3$, OCF$_3$, OH, SH, CN, NH$_2$, NHCH$_3$, N(CH$_3$)$_2$ and NO$_2$. In another embodiment, R$^7$ and R$^3$ and R$^{7'}$ and R$^{3'}$ in the compounds of Formula I are joined to form, together with the atoms to which they are attached, an unsubstituted phenyl ring.

In a further embodiment of the methods and uses of the disclosure, Y$^-$ and Y$^{'-}$ in the compounds of Formula I are, independently, any suitable counter anion, including, but not limited to, halides (iodide, chloride, bromide or fluoride), sulfates, formates, acetates, alkylsulfonates, aryl sulfonates, borates and phosphates. Suitably the anion is Cl$^-$, F$^-$, I$^-$, Br$^-$ or BF$_4^-$.

It is an embodiment of the methods and uses of the disclosure that the two positively charged imidazolium or triazolium rings in the compounds of Formula I are the same.

It is a further embodiment of the methods and uses of the disclosure that the compounds of Formula I are selected from QT71, QT86, QT87, QT88, QT89, QT98, QT99, QT101, QT102, QT103, QT107, QT109, QT110, QT113, QT114, QT116, QT118, QT119, QT123 and QT124 as shown in Table 1, and pharmaceutically acceptable salts, solvates and prodrugs thereof. In another embodiment, the compounds of Formula I are selected from QT88, QT89, QT98, QT99, QT101, QT102, QT103, QT107, QT109, QT110, QT113, QT116, QT118, QT119, QT123 and QT124 as shown in Table 1, and pharmaceutically acceptable salts, solvates and prodrugs thereof.

The present disclosure also includes a method of treating or preventing an infection by a *Plasmodium* or *Babesia* parasite comprising administering to a subject in need thereof, an effective amount of one or more compounds selected from a compound of Formula II, and pharmaceutically acceptable salts, solvates, and prodrugs thereof:

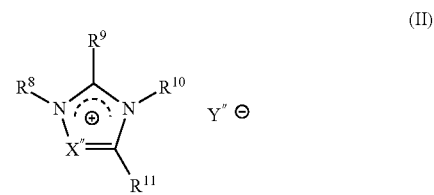

(II)

wherein,

R$^8$ and R$^{10}$ are independently selected from C$_{1-20}$alkyl, C$_{6-14}$aryl, C$_{3-20}$cycloalkyl and C$_{1-20}$alkylene-C$_{6-14}$aryl, where each C$_{1-20}$alkyl, C$_{3-20}$cycloalkyl and C$_{1-20}$alkylene is, independently, unsubstituted or substituted with one or more substituents independently selected from halo, C$_{1-6}$alkyl, OC$_{1-6}$alkyl, SC$_{1-6}$alkyl, fluoro-substituted C$_{1-6}$alkyl, fluoro-substituted OC$_{1-6}$alkyl, fluoro-substituted SC$_{1-6}$alkyl, OH, SH, CN, NH$_2$, NHC$_{1-6}$alkyl, N(C$_{1-6}$alkyl)(C$_{1-6}$alkyl), NO$_2$, =O, =S, C$_{6-10}$aryl, C$_{1-4}$alkyleneC$_{6-10}$aryl and C(O)R$^{12}$, and/or one or more carbon atoms are optionally replaced with a heteroatom independently selected from O, S and NR$^{13}$, and each C$_{6-14}$aryl is unsubstituted or substituted with one or more substituents independently selected from halo, C$_{1-6}$alkyl, OC$_{1-6}$alkyl, SC$_{1-6}$ alkyl, fluoro-substituted C$_{1-6}$alkyl, fluoro-substituted OC$_{1-6}$ alkyl, fluoro-substituted SC$_{1-6}$alkyl, OH, SH, CN, NH$_2$, NHC$_{1-6}$alkyl, N(C$_{1-6}$alkyl)(C$_{1-6}$alkyl), NO$_2$, C$_{6-10}$aryl, C$_{1-4}$alkyleneC$_{6-10}$aryl and C(O)R$^{12}$;

R$^9$ is independently selected from H, C$_{1-6}$alkyl, C$_{3-10}$cycloalkyl and C$_{6-14}$aryl, where each C$_{1-6}$alkyl, C$_{3-10}$cycloalkyl and C$_{6-14}$aryl is unsubstituted or substituted with one or more substituents independently selected from halo, C$_{1-6}$alkyl, OC$_{1-6}$alkyl, SC$_{1-6}$alkyl, fluoro-substituted C$_{1-6}$alkyl, fluoro-substituted OC$_{1-6}$alkyl, fluoro-substituted SC$_{1-6}$alkyl, OH, SH, CN, NH$_2$, NHC$_{1-6}$alkyl, N(C$_{1-6}$alkyl)(C$_{1-6}$alkyl), NO$_2$ and C(O)R$^{12}$;

R$^{11}$ is selected from H, C$_{1-6}$alkyl, OC$_{1-6}$alkyl, SC$_{1-6}$alkyl, NHC$_{1-6}$alkyl, N(C$_{1-6}$alkyl)(C$_{1-6}$alkyl), C$_{3-10}$cycloalkyl, OC$_{3-10}$cycloalkyl, SC$_{3-10}$cycloalkyl, C$_{6-14}$aryl, C$_{1-6}$alkyleneC$_{6-14}$aryl, OC$_{6-14}$aryl and SC$_{6-14}$aryl, where each C$_{1-6}$alkyl, C$_{1-6}$alkylene, C$_{3-10}$cycloalkyl and C$_{6-14}$aryl is unsubstituted or substituted with one or more substituents independently selected from halo, C$_{1-6}$alkyl, OC$_{1-6}$alkyl, SC$_{1-6}$alkyl, fluoro-substituted C$_{1-6}$alkyl, fluoro-substituted OC$_{1-6}$alkyl, fluoro-substituted SC$_{1-6}$alkyl, OH, SH, CN, NH$_2$, NHC$_{1-6}$alkyl, N(C$_{1-6}$alkyl)(C$_{1-6}$alkyl), NO$_2$, C$_{6-10}$aryl, C$_{1-4}$alkyleneC$_{6-10}$aryl and C(O)R$^{12}$, or R$^{10}$ and R$^{11}$ are joined to form, together with the atoms to which they are attached, a monocyclic or bicyclic ring, where the ring is saturated, unsaturated or aromatic and is unsubstituted or substituted with one or more substituents independently selected from halo, C$_{1-6}$alkyl, OC$_{1-6}$alkyl, SC$_{1-6}$alkyl, fluoro-substituted C$_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^{12}$;

$R^{12}$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$cycloalkyl, $OC_{6-14}$aryl, $SC_{6-14}$aryl, $C_{1-4}$alkylene$C_{6-14}$aryl, $NH_2$, $NH(C_{1-6}$alkyl$)$ and $N(C_{1-6}$alkyl$)(C_{1-6}$alkyl$)$;

$R^{13}$ is selected from H and $C_{1-4}$alkyl;

X″ is selected from C—$R^{14}$ and N;

$R^{14}$ is selected from H, $C_{1-6}$alkyl, $OC_{1-6}$alkyl, $SC_{1-6}$alkyl, $NHC_{1-6}$alkyl, $N(C_{1-6}$alkyl$)(C_{1-6}$alkyl$)$, $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^{12}$, or $R^{14}$ and $R^{11}$ are joined to form, together with the atoms to which they are attached, a monocyclic or bicyclic ring, where the ring is saturated, unsaturated or aromatic and is unsubstituted or substituted one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^{12}$, or $R^{14}$ and $R^8$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^{12}$; and Y‴⁻ is a counter anion.

In further embodiments, the present disclosure includes a use of one or more compounds selected from a compound of Formula II as defined above, and pharmaceutically acceptable salts, solvates, and prodrugs thereof, for the prevention or treatment of an infection by a *Plasmodium* or *Babesia* parasite as well as a use of one or more compounds selected from a compound of Formula II as defined above, and pharmaceutically acceptable salts, solvates, and prodrugs thereof, for the preparation of a medicament for the prevention or treatment of an infection by a *Plasmodium* or *Babesia* parasite.

The present disclosure further includes a method of preventing or treating an invasion of a *Plasmodium* or *Babesia* parasite into an erythrocyte comprising administering to the erythrocyte an effective amount of one or more compounds selected from a compound of Formula II as defined above, and pharmaceutically acceptable salts, solvates, and prodrugs thereof.

The present disclosure also includes a use of one or more compounds selected from a compound of Formula II as defined above, and pharmaceutically acceptable salts, solvates, and prodrugs thereof, to prevent or treat an invasion of a *Plasmodium* or *Babesia* parasite into an erythrocyte as well as a use of one or more compounds selected from a compound of Formula II as defined above, and pharmaceutically acceptable salts, solvates, and prodrugs thereof, to prepare a medicament to prevent or treat an invasion of a *Plasmodium* or *Babesia* parasite into an erythrocyte.

In an embodiment of the methods and uses of the disclosure, $R^8$ in the compounds of Formula II is selected from $C_{1-6}$alkyl, phenyl, naphthyl, $C_{1-6}$alkyene-phenyl and $C_{1-6}$alkyene-naphthyl, where each $C_{1-6}$alkyl and $C_{1-6}$alkylene is unsubstituted or substituted with one to three, suitably one or two, more suitably one, substituent independently selected from chloro, bromo, iodo, fluoro, $CH_3$, $OCH_3$, $CF_3$, $OCF_3$, OH, SH, CN, $NH_2$, $NHCH_3$, $N(CH_3)_2$, $NO_2$ and =O, and each phenyl and naphthyl is unsubstituted or substituted with one, two, three four or five, substituents independently selected from chloro, bromo, iodo, fluoro, $CH_3$, $OCH_3$, $CF_3$, $OCF_3$, OH, SH, CN, $NH_2$, $NHCH_3$, $N(CH_3)_2$ and $NO_2$.

In an embodiment of the methods and uses of the disclosure, $R^9$ in the compounds of Formula II is selected from H, $C_{1-6}$alkyl and phenyl, where $C_{1-6}$alkyl and phenyl are unsubstituted or fluoro-substituted and/or substituted with one to three substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. Suitably $R^9$ in the compounds of Formula II is selected from H and unsubstituted phenyl.

In an embodiment of the methods and uses of the disclosure, $R^{10}$ in the compounds of Formula II is selected from $C_{1-6}$alkyl, phenyl, naphthyl, $C_{1-6}$alkyene-phenyl and $C_{1-6}$alkyene-naphthyl, where each $C_{1-6}$alkyl and $C_{1-6}$alkylene is unsubstituted or substituted with one to three, suitably one or two, more suitably one, substituent independently selected from chloro, bromo, iodo, fluoro, $CH_3$, $OCH_3$, $CF_3$, $OCF_3$, OH, SH, CN, $NH_2$, $NHCH_3$, $N(CH_3)_2$, $NO_2$ and =O, and each phenyl and naphthyl is unsubstituted or substituted with one, two, three, four or five, substituents independently selected from chloro, bromo, iodo, fluoro, $CH_3$, $OCH_3$, $CF_3$, $OCF_3$, OH, SH, CN, $NH_2$, $NHCH_3$, $N(CH_3)_2$ and $NO_2$.

In an embodiment of the methods and uses of the disclosure, $R^{11}$ in the compounds of Formula II is selected from H, $CH_3$, $OCH_3$, $SCH_3$, $NHCH_3$, $N(CH_3)_2$, cyclopentyl, cyclohexyl, O-cyclopentyl, O-cyclohexyl, O-cyclopentyl, O-cyclohexyl, phenyl, naphthyl, benzyl, O-phenyl, O-naphthyl, S-phenyl and S-naphthyl, the latter 13 groups being unsubstituted or substituted with one, two, three or five, substituents independently selected from chloro, bromo, iodo, fluoro, $CH_3$, $OCH_3$, $CF_3$, $OCF_3$, OH, SH, CN, $NH_2$, $NHCH_3$, $N(CH_3)_2$ and $NO_2$. In an embodiment, $R^{11}$ in the compounds of Formula II is selected from H, $SCH_3$ and phenyl.

In a further embodiment of the methods and uses of the present disclosure, $R^{10}$ and $R^{11}$ in the compounds of Formula II are joined to form, together with the atoms to which they are attached, a monocyclic 5- or 6-membered ring, where the ring is unsaturated and is unsubstituted or fluoro-substituted and/or substituted with one to two substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl$)(C_{1-4}$alkyl$)$ and $NO_2$. In another embodiment, $R^{10}$ and $R^{11}$ in the compounds of Formula II are joined to form, together with the atoms to which they are attached, a monocyclic 5-membered ring, where the ring is unsaturated and is unsubstituted or substituted with one substituent selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In another embodiment, $R^{10}$ and $R^{11}$ in the compounds of Formula II are joined to form, together with the atoms to which they are attached, a monocyclic 5-membered ring, where the ring is unsaturated and is unsubstituted.

In an embodiment of the methods and uses of the disclosure, $R^{12}$ in the compounds of Formula II is selected from H, OH, SH, $C_{3-6}$cycloalkyl, $C_{6-10}$aryl, $OC_{1-4}$alkyl, $SC_{1-4}$alkyl, $OC_{3-6}$cycloalkyl, $SC_{3-6}$cycloalkyl, $OC_{6-10}$aryl, $SC_{6-10}$aryl, $NH_2$, $NH(C_{1-4}alkyl)$ and $N(C_{1-4}alkyl)_2$. In a further embodiment, $R^{12}$ in the compounds of Formula II is selected from H, OH, $CH_3$, cyclopentyl, cyclohexyl, phenyl, $OCH_3$, O-cyclopentyl, O-cyclohexyl, O-phenyl, $NH_2$, $NH(CH_3)$ and $N(CH_3)_2$. In a further embodiment, $R^{12}$ in the compounds of Formula II is selected from $CH_3$, OH, $OCH_3$, $NH_2$, $NH(CH_3)$ and $N(CH_3)_2$. In a further embodiment, $R^{12}$ in the compounds of Formula II is $CH_3$.

In an embodiment of the methods and uses of the disclosure, $R^{13}$ in the compounds of Formula II is selected from H and $CH_3$.

In a further embodiment of the methods and uses of the present disclosure, X" in the compounds of Formula II is C—$R^{14}$.

In a further embodiment of the methods and uses of the present disclosure, X" in the compounds of Formula II is N.

In a further embodiment of the methods and uses of the present disclosure, $R^{14}$ in the compounds of Formula II is selected from H, $C_{1-6}$alkyl, $C_{3-6}$cycloalkyl and $C_{6-10}$aryl, where each $C_{1-6}$alkyl, $C_{3-6}$cycloalkyl and $C_{6-10}$aryl is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}alkyl)(C_{1-4}alkyl)$ and $NO_2$. In a further embodiment $R^{14}$ in the compounds of Formula II is selected from H, $CH_3$, cyclopentyl, cyclohexyl and phenyl, where cyclopentyl, cyclohexyl and phenyl are unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$. In a further embodiment, $R^{14}$ compounds of Formula II is selected from H, phenyl and $CH_3$, suitably H In a further embodiment of the methods and uses of the present disclosure, $R^{14}$ and $R^{11}$ in the compounds of Formula II are joined to form, together with the atoms to which they are attached, a monocyclic 5- or 6-membered ring, where the ring is unsaturated or aromatic and is unsubstituted or fluoro-substituted and/or substituted with one to two substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}alkyl)(C_{1-4}alkyl)$ and $NO_2$. In another embodiment, $R^{14}$ and $R^{11}$ in the compounds of Formula II are joined to form, together with the atoms to which they are attached, a monocyclic 6-membered ring, where the ring is unsaturated or aromatic and is unsubstituted or substituted with one substituent selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In another embodiment, $R^{14}$ and $R^{11}$ in the compounds of Formula II are joined to form, together with the atoms to which they are attached, an unsubstituted phenyl ring.

In a further embodiment of the methods and uses of the present disclosure, $R^{14}$ and $R^8$ in the compounds of Formula II are joined to form, together with the atoms to which they are attached, a monocyclic 5- or 6-membered ring, where the ring is unsaturated and is unsubstituted or fluoro-substituted and/or substituted with one to two substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}alkyl)(C_{1-4}alkyl)$ and $NO_2$. In another embodiment, $R^{14}$ and $R^8$ in the compounds of Formula II are joined to form, together with the atoms to which they are attached, a monocyclic 5-membered ring, where the ring is unsaturated and is unsubstituted or substituted with one substituent selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In another embodiment, $R^{14}$ and $R^8$ in the compounds of Formula II are joined to form, together with the atoms to which they are attached, a monocyclic 5-membered ring, where the ring is unsaturated and is unsubstituted.

In a further embodiment of the methods and uses of the disclosure, $Y''^-$ in the compounds of Formula II is any suitable counter anion, including, but not limited to, halides (iodide, chloride, bromide or fluoride), sulfates, formates, acetates, alkylsulfonates, aryl sulfonates, borates and phosphates. Suitably the anion is $Cl^-$, $F^-$, $I^-$, $Br^-$ or $BF_4^-$.

It is a further embodiment of the methods and uses of the disclosure that the compounds of Formula II are selected from QT55, QT57, QT58, QT59, QT60, QT68, QT69, QT70, QT72, QT73, QT74, QT75, QT76, QT77, QT78, QT79, QT80, QT81, QT82, QT83, QT84, QT85, QT90, QT91, QT92, QT93, QT94, QT95, QT96, QT104 and QT105 as shown in Table 1, and pharmaceutically acceptable salts, solvates and prodrugs thereof.

The compounds of Formula I and/or II are used alone or contemporaneously with other types of treatment for an infection by a *Plasmodium* or *Babesia* parasite or for malaria or for babesiosis.

In an embodiment of the disclosure, the parasite is a *Plasmodium* parasite and the methods and uses are directed to the prevention and treatment of malaria in a subject in need thereof.

III. Novel Compounds of the Disclosure

Novel compounds showing anti-parasitic, for example, anti-*Plasmodium*, activity have been prepared. Accordingly, the present disclosure includes all uses of these novel compounds including their use in therapeutic methods and compositions for treating or preventing malaria, their use in diagnostic assays and their use as research tools and as starting materials and/or intermediates in the preparation of other chemical entities.

In a particular embodiment of the present disclosure, there are included novel compounds of Formula Ia wherein X is N. Accordingly, the present application includes compound selected from a compound of Formula Ia, and pharmaceutically acceptable salts, solvates and prodrugs thereof:

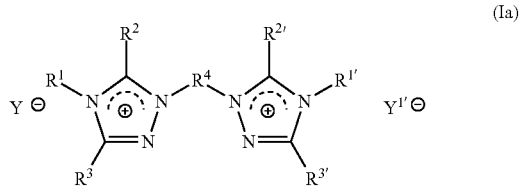

(Ia)

wherein, $R^1$ and $R^{1'}$ are independently selected from $C_{1-20}$alkyl, $C_{3-20}$cycloalkyl, $C_{6-14}$aryl and $C_{1-20}$alkylene-$C_{6-14}$aryl, where each $C_{1-20}$alkyl, $C_{3-20}$cycloalkyl and $C_{1-20}$alkylene is, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, =O, =S, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$;

$R^2$ and $R^{2'}$ are independently selected from H, $C_{1-6}$alkyl, $C_{3-10}$cycloalkyl and $C_{6-14}$aryl, where each $C_{1-6}$alkyl, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$ and $C(O)R^5$;

$R^3$ and $R^{3'}$ are independently selected from H, $C_{1-6}$alkyl, $OC_{1-6}$alkyl, $SC_{1-6}$alkyl, $NHC_{1-6}$alkyl, $N(C_{1-6}$alkyl$)(C_{1-6}$alkyl$)$, $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{3-10}$cycloalkyl or $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$, or $R^1$ and $R^3$ and/or $R^{1'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$;

$R^4$ is selected from $C_{10-20}$alkylene, $(C_{6-10}$arylene$)_p$, $C_{1-10}$alkylene-$(C_{6-10}$arylene$)_p$, $(C_{6-10}$arylene$)_p$-$C_{1-10}$alkylene, $C_{1-10}$alkylene-$(C_{6-10}$arylene$)_p$-$C_{1-10}$alkylene and $(C_{6-10}$arylene$)$-$C_{1-10}$alkylene-$(C_{6-10}$arylene$)$, wherein each $C_{10-20}$alkylene and $C_{1-10}$alkylene are unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $=O$, $=S$ and $C(O)R^5$, and/or one or more carbon atoms are optionally replaced with a heteroatom independently selected from O, S and $NR^6$, and each $C_{6-10}$arylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$ and $C(O)R^5$;

$R^5$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$cycloalkyl, $OC_{6-14}$aryl, $SC_{6-14}$aryl, $C_{1-4}$alkylene$C_{6-14}$aryl, $NH_2$, $NH(C_{1-6}$alkyl$)$ and $N(C_{1-6}$alkyl$)(C_{1-6}$alkyl$)$;

$R^6$ is selected from H and $C_{1-4}$alkyl;

p is 1 or 2;

and $Y^-$ and $Y^{'-}$ are, independently, a counter anion, with the proviso that when $R^4$ is $C_{12}$alkylene and $R^2$, $R^{2'}$, $R^3$ and $R^{3'}$ are all $CH_3$, then $R^1$ and $R^{1'}$ are not both $C_{10}$alkyl.

In an embodiment of the disclosure, $R^1$ and $R^{1'}$ in the compounds of Formula Ia are independently selected from $C_{1-10}$alkyl, $C_{3-10}$cycloalkyl, $C_{6-10}$aryl and $C_{1-10}$alkylene-$C_{6-10}$aryl, where $C_{1-10}$alkyl and $C_{1-10}$alkylene are, independently, unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl$)(C_{1-4}$alkyl$)$, $NO_2$, $=O$ and $=S$ and/or one to three carbon atoms are optionally replaced with a heteroatom independently selected from O, S and $NR^6$, and each $C_{6-10}$aryl is unsubstituted or fluoro-substituted and/or substituted with one to three substituents independently selected from chloro, bromo, iodo, fluoro-substituted $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl$)(C_{1-4}$alkyl$)$ and $NO_2$. In a further embodiment of the disclosure, $R^1$ and $R^{1'}$ in the compounds of Formula Ia are independently selected from $C_{1-4}$alkyl, phenyl and $C_{1-4}$alkylene-phenyl, where $C_{1-4}$alkyl and $C_{1-4}$alkylene are, independently, unsubstituted or fluoro-substituted and/or substituted with one or two groups independently selected from chloro, bromo, iodo, $CH_3$, $OCH_3$, $CF_3$, $OCF_3$, OH, CN, $NH_2$, $NHCH_3$, $N(CH_3)_2$, $NO_2$ and $=O$ and/or one or two carbon atoms are optionally replaced with O, and each phenyl is unsubstituted or fluoro-substituted and/or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$, $NO_2$ and $=O$. In a further embodiment of the present disclosure, $R^1$ and $R^{1'}$ in the compounds of Formula Ia are independently $C_{1-6}$alkyl or $C_{1-4}$alkylene-phenyl, where phenyl is unsubstituted, fluoro-substituted or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$ and $NO_2$. In a further embodiment, $R^1$ and $R^{1'}$ in the compounds of Formula Ia are the same and are both selected from $CH_3$, $CH_2CH_3$, $(CH_2)_2CH_3$, $CH(CH_3)_2$, $(CH_2)_3CH_3$, $CH_2CH(CH_3)_2$, $C(CH_3)_3$, $CH(CH_3)CH_2CH_3$, $CH_2$phenyl, $CH_2$-(4-nitrophenyl), $CH_2$-(3-nitrophenyl) and $CH_2$-(2-nitrophenyl).

In another embodiment of the disclosure $R^2$ and $R^{2'}$ in the compounds of Formula Ia are independently selected from H, $C_{1-4}$alkyl, $C_{3-6}$cycloalkyl and $C_{6-10}$aryl, where $C_{1-4}$alkyl, $C_{3-6}$cycloalkyl and $C_{6-10}$aryl are unsubstituted or fluoro-substituted and/or substituted with one to three substituents independently selected from chloro, bromo, iodo, $C_{1-4}$alkyl, $OC_{1-4}$ alkyl, fluoro-substituted $C_{1-4}$alkyl, fluoro-substituted $OC_{1-4}$ alkyl, OH, SH, CN, $NH_2$, $NHC_{1-4}$alkyl, $N(C_{1-4}$alkyl$)(C_{1-4}$ alkyl$)$ and $NO_2$. In a further embodiment $R^2$ and $R^{2'}$ in the compounds of Formula Ia are independently selected from H, $CH_3$, cyclopentyl, cyclohexyl and phenyl, where cyclopentyl, cyclohexyl and phenyl are unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$. In a further embodiment, $R^2$ and $R^{2'}$ in the compounds of Formula Ia are the same and are both selected from H and $CH_3$, suitably H.

In another embodiment of the disclosure $R^3$ and $R^{3'}$ in the compounds of Formula Ia are independently selected from H, $C_{1-4}$alkyl, $OC_{1-4}$alkyl, $SC_{1-4}$alkyl, $NHC_{1-4}$alkyl, $N(C_{1-4}$alkyl$)(C_{1-4}$alkyl$)$, $C_{3-6}$cycloalkyl, $OC_{3-6}$cycloalkyl, $SC_{3-6}$cycloalkyl, $C_{6-10}$aryl, $C_{1-4}$alkylene$C_{6-10}$aryl, $OC_{6-10}$aryl and $SC_{6-10}$aryl, where each $C_{1-4}$alkyl, $C_{1-4}$alkylene, $C_{3-6}$cycloalkyl or $C_{6-10}$aryl is unsubstituted or fluoro-substituted and/or substituted with one to three substituents independently selected from chloro, bromo, iodo, $C_{1-4}$alkyl, $OC_{1-4}$ alkyl, fluoro-substituted $C_{1-4}$alkyl, fluoro-substituted $OC_{1-4}$ alkyl, OH, SH, CN, $NH_2$, $NHC_{1-4}$alkyl, $N(C_{1-4}$alkyl$)(C_{1-4}$ alkyl$)$ and $NO_2$. In a further embodiment $R^3$ and $R^{3'}$ in the compounds of Formula Ia are independently selected from H, $CH_3$, $OCH_3$, $SCH_3$, $NHCH_3$, $N(CH_3)_2$, cyclopentyl, cyclohexyl, O-cyclopentyl, O-cyclohexyl, phenyl, benzyl, O-phenyl and S-phenyl, where, each phenyl, cyclopentyl and cyclohexyl is unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$. In a further embodiment, $R^3$ and $R^{3'}$ in the compounds of Formula Ia are the same and are both selected from H and $CH_3$, suitably H.

In another embodiment of the disclosure, $R^1$ and $R^3$ and/or $R^{1'}$ and $R^{3'}$ in the compounds of Formula Ia are joined to form, together with the atoms to which they are attached, a monocyclic 5- or 6-membered ring, where the ring is unsaturated and is unsubstituted or fluoro-substituted and/or substituted with one to two substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}alkyl)(C_{1-4}alkyl)$ and $NO_2$. In another embodiment, $R^1$ and $R^3$ and/or $R^{1'}$ and $R^{3'}$ in the compounds of Formula Ia are joined to form, together with the atoms to which they are attached, a monocyclic 5-membered ring, where the ring is unsaturated and is unsubstituted or substituted with one substituent selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In another embodiment, $R^1$ and $R^3$ and $R^{1'}$ and $R^{3'}$ in the compounds of Formula Ia are joined to form, together with the atoms to which they are attached, a monocyclic 5-membered ring, where the ring is unsaturated and is unsubstituted.

In another embodiment of the disclosure, $R^4$ in the compounds of Formula Ia is selected from $C_{11-17}$alkylene, (phenylene)$_p$, $C_{1-4}$alkylene-(phenylene)$_p$, (phenylene)$_p$-$C_{1-4}$alkylene, $C_{1-4}$alkylene-(phenylene)$_p$-$C_{1-4}$alkylene and phenylene-$C_{1-4}$alkylene-phenylene, wherein each alkylene is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}alkyl)(C_{1-4}alkyl)$, $NO_2$, =O and =S and/or one to three carbon atoms are optionally replaced with a heteroatom independently selected from O, S and $NR^6$, and each phenylene is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}alkyl)(C_{1-4}alkyl)$ and $NO_2$, and p is 1 or 2. In another embodiment, $R^4$ in the compounds of Formula Ia is selected from $C_{12-15}$alkylene, biphenylene, $CH_2$-biphenylene, biphenylene-$CH_2$, $CH_2$-biphenylene-$CH_2$, wherein each alkylene, is unsubstituted or fluoro-substituted and/or substituted with one to two substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$ and =O and/or one to two carbon atoms are optionally replaced with a heteroatom independently selected from O, S and $NR^6$, and each biphenylene is unsubstituted or fluoro-substituted and/or substituted with one to two substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In a further embodiment of the disclosure, $R^4$ in the compounds of Formula Ia is selected from $C_{12-15}$alkylene and biphenylene both of which are unsubstituted. In a further embodiment of the disclosure, $R^4$ in the compounds of Formula Ia is selected from $C_{13}$alkylene and biphenylene both of which are unsubstituted.

In a further embodiment of the present disclosure, $R^5$ in the compounds of Formula Ia is selected from H, OH, SH, $C_{1-4}$alkyl, $C_{3-6}$cycloalkyl, $C_{6-10}$aryl, $OC_{1-4}$alkyl, $SC_{1-4}$alkyl, $OC_{3-6}$cycloalkyl, $SC_{3-6}$cycloalkyl, $OC_{6-10}$aryl, $SC_{6-10}$aryl, $NH_2$, $NH(C_{1-4}alkyl)$ and $N(C_{1-4}alkyl)_2$. In a further embodiment, $R^5$ in the compounds of Formula Ia is selected from H, OH. $CH_3$, cyclopentyl, cyclohexyl, phenyl, $OCH_3$, O-cyclopentyl, O-cyclohexyl, O-phenyl, $NH_2$, $NH(CH_3)$ and $N(CH_3)_2$. In a further embodiment, $R^5$ in the compounds of Formula Ia is selected from $CH_3$, OH, $OCH_3$, $NH_2$, $NH(CH_3)$ and $N(CH_3)_2$. In a further embodiment, $R^5$ in the compounds of Formula Ia is $CH_3$.

In a further embodiment of the methods and uses of the present disclosure, $R^6$ in the compound of Formula Ia is selected from H and $CH_3$.

In a further embodiment of the disclosure, $Y^-$ and $Y'^-$ in the compounds of Formula Ia are, independently, any suitable counter anion, including, but not limited to, halides (iodide, chloride, bromide or fluoride), sulfates, formates, acetates, alkylsulfonates, aryl sulfonates, borates and phosphates. Suitably the anion is $Cl^-$, $F^-$, $I^-$, $Br^-$ or $BF_4^-$.

It is an embodiment of the disclosure that the two positively charged triazolium rings in the compounds of Formula Ia are the same.

It is a further embodiment of the disclosure that the compounds of Formula Ia is

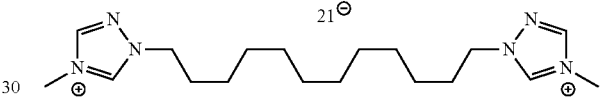

(QT124 as shown in Table 1), and pharmaceutically acceptable salts, solvates and prodrugs thereof.

In a further particular embodiment of the present disclosure, there are included novel compounds of Formula Ib wherein X is N and $R^2$, $R^{2'}$, $R^3$ and $R^{3'}$ are H. Accordingly, the present application includes compound selected from a compound of Formula Ib, and pharmaceutically acceptable salts, solvates and prodrugs thereof:

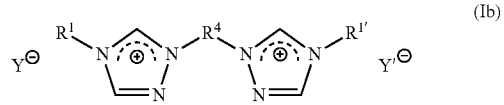

(Ib)

$R^1$ and $R^{1'}$ are independently selected from $C_{1-20}$alkyl, $C_{3-20}$cycloalkyl, $C_{6-14}$aryl and $C_{1-20}$alkylene-$C_{6-14}$aryl, where $C_{1-20}$alkyl, $C_{3-20}$cycloalkyl and $C_{1-20}$alkylene are, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, =O, =S, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$;

$R^4$ is selected from $C_{10-20}$alkylene, $(C_{6-10}$arylene$)_p$, $C_{1-10}$alkylene-$(C_{6-10}$arylene$)_p$, $(C_{6-10}$arylene$)_p$-$C_{1-10}$alkylene, $C_{1-10}$alkylene-$(C_{6-10}$arylene$)_p$-$C_{1-10}$alkylene and $(C_{6-10}$-arylene)-$C_{1-10}$alkylene-$(C_{6-10}$arylene), wherein each $C_{10-20}$alkylene and $C_{1-10}$alkylene are unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)$(C_{1-6}$alkyl), $NO_2$, =O, =S and $C(O)R^5$, and/or one or more carbon atoms are optionally replaced with a heteroatom independently selected from O, S and $NR^6$, and each $C_{6-10}$arylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl)$(C_{1-6}$alkyl), $NO_2$ and $C(O)R^5$;

$R^5$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$cycloalkyl, $OC_{6-14}$aryl, $SC_{6-14}$aryl, $C_{1-4}$alkylene $C_{6-14}$aryl, $NH_2$, $NH(C_{1-6}$alkyl) and $N(C_{1-6}$alkyl)$(C_{1-6}$alkyl);

$R^6$ is selected from H and $C_{1-4}$alkyl;

p is 1 or 2; and $Y^-$ and $Y'^-$ are, independently, a counter anion.

In an embodiment of the disclosure, $R^1$ and $R^{1'}$ in the compounds of Formula Ib are independently selected from $C_{1-10}$alkyl, $C_{3-10}$cycloalkyl, $C_{6-10}$aryl and $C_{1-10}$alkylene-$C_{6-10}$aryl, where $C_{1-10}$alkyl, $C_{3-10}$cycloalkyl and $C_{1-10}$alkylene are, independently, unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl), $NO_2$, =O and =S and/or one to three carbon atoms are optionally replaced with a heteroatom independently selected from O, S and $NR^6$, and each $C_{6-10}$aryl is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$. In a further embodiment of the disclosure, $R^1$ and $R^{1'}$ in the compounds of Formula Ib are independently selected from $C_{1-4}$alkyl, phenyl and $C_{1-4}$alkylene-phenyl, where $C_{1-4}$alkyl and $C_{1-4}$alkylene are, independently, unsubstituted or fluoro-substituted and/or substituted with one or two groups independently selected from chloro, bromo, iodo, $CH_3$, $OCH_3$, $CF_3$, $OCF_3$, OH, CN, $NH_2$, $NHCH_3$, $N(CH_3)_2$, $NO_2$ and =O and/or one or two carbon atoms are optionally replaced with O, and each phenyl is unsubstituted or fluoro-substituted and/or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$, $NO_2$ and =O. In a further embodiment of the present disclosure, $R^1$ and $R^{1'}$ in the compounds of Formula Ib are independently $C_{1-6}$alkyl or $C_{1-4}$alkylene-phenyl, where phenyl is unsubstituted, fluoro-substituted or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$ and $NO_2$. In a further embodiment, $R^1$ and $R^{1'}$ in the compounds of Formula Ib are the same and are both selected from $CH_3$, $CH_2CH_3$, $(CH_2)_2CH_3$, $CH(CH_3)_2$, $(CH_2)_3CH_3$, $CH_2CH(CH_3)_2$, $C(CH_3)_3$, $CH(CH_3)CH_2CH_3$, $CH_2$phenyl, $CH_2$-(4-nitrophenyl), $CH_2$-(3-nitrophenyl) and $CH_2$-(2-nitrophenyl).

In another embodiment of the disclosure, $R^4$ in the compounds of Formula Ib is selected from $C_{11-17}$alkylene, (phenylene)$_p$, $C_{1-4}$alkylene-(phenylene)$_p$, (phenylene)$_p$-$C_{1-4}$alkylene, $C_{1-4}$alkylene-(phenylene)$_p$-$C_{1-4}$alkylene and phenylene-$C_{1-4}$alkylene-phenylene, wherein each alkylene is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl), $NO_2$, =O and =S and/or one to three carbon atoms are optionally replaced with a heteroatom independently selected from O, S and $NR^6$, and each phenylene is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$, and p is 1 or 2. In another embodiment, $R^4$ in the compounds of Formula Ib is selected from $C_{12-15}$alkylene, biphenylene, $CH_2$-biphenylene, biphenylene-$CH_2$, $CH_2$-biphenylene-$CH_2$, wherein each alkylene, is unsubstituted or fluoro-substituted and/or substituted with one to two substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$ and =O and/or one to two carbon atoms are optionally replaced with a heteroatom independently selected from O, S and $NR^6$, and each biphenylene is unsubstituted or fluoro-substituted and/or substituted with one to two substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In a further embodiment of the disclosure, $R^4$ in the compounds of Formula Ib is selected from $C_{12-15}$alkylene and biphenylene both of which are unsubstituted. In a further embodiment of the disclosure, $R^4$ in the compounds of Formula Ib is selected from $C_{13}$alkylene and biphenylene both of which are unsubstituted.

In a further embodiment of the present disclosure, $R^5$ in the compounds of Formula Ib is selected from H, OH, SH, $C_{1-4}$alkyl, $C_{3-6}$cycloalkyl, $C_{6-10}$aryl, $OC_{1-4}$alkyl, $SC_{1-4}$alkyl, $OC_{3-6}$cycloalkyl, $SC_{3-6}$cycloalkyl, $OC_{6-10}$aryl, $SC_{6-10}$aryl, $NH_2$, $NH(C_{1-4}$alkyl) and $N(C_{1-4}$alkyl)$_2$. In a further embodiment, $R^5$ in the compounds of Formula Ib is selected from H, OH. $CH_3$, cyclopentyl, cyclohexyl, phenyl, $OCH_3$, O-cyclopentyl, O-cyclohexyl, O-phenyl, $NH_2$, $NH(CH_3)$ and $N(CH_3)_2$. In a further embodiment, $R^5$ in the compounds of Formula Ib is selected from $CH_3$, OH, $OCH_3$, $NH_2$, $NH(CH_3)$ and $N(CH_3)_2$. In a further embodiment, $R^5$ in the compounds of Formula Ia is $CH_3$.

In a further embodiment of the methods and uses of the present disclosure, $R^6$ in the compound of Formula Ib is selected from H and $CH_3$.

In a further embodiment of the disclosure, $Y^-$ and $Y'^-$ in the compounds of Formula Ib are, independently, any suitable counter anion, including, but not limited to, halides (iodide, chloride, bromide or fluoride), sulfates, formates, acetates, alkylsulfonates, aryl sulfonates, borates and phosphates. Suitably the anion is $Cl^-$, $F^-$, $I^-$, $Br^-$ or $BF_4^-$.

It is an embodiment of the disclosure that the two positively charged triazolium rings in the compounds of Formula Ib are the same.

It is a further embodiment of the disclosure that the compounds of Formula Ib is

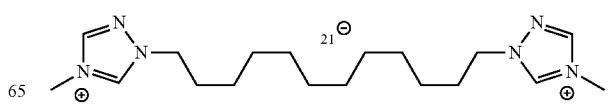

(QT124 as shown in Table 1), and pharmaceutically acceptable salts, solvates and prodrugs thereof.

In another particular embodiment of the present disclosure, there are included novel compounds of Formula Ic wherein $R^4$ comprises a bi-phenyl linker. Accordingly, the present application includes compound selected from a compound of Formula Ic, and pharmaceutically acceptable salts, solvates and prodrugs thereof:

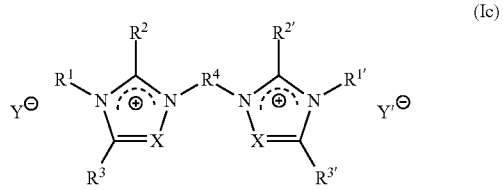

(Ic)

$R^1$ and $R^{1'}$ are independently selected from $C_{1-20}$alkyl, $C_{3-20}$cycloalkyl, $C_{6-14}$aryl and $C_{1-20}$alkylene-$C_{6-14}$aryl, where $C_{1-20}$alkyl, $C_{3-20}$cycloalkyl and $C_{1-20}$alkylene are, independently, unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $=O$, $=S$, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$;

$R^2$ and $R^{2'}$ are independently selected from H, $C_{1-6}$alkyl, $C_{3-10}$cycloalkyl and $C_{6-14}$aryl, where $C_{1-6}$alkyl, $C_{3-10}$cycloalkyl and $C_{6-14}$aryl are unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$ and $C(O)R^5$;

$R^3$ and $R^{3'}$ are independently selected from H, $C_{1-6}$alkyl, $OC_{1-6}$alkyl, $SC_{1-6}$alkyl, $NHC_{1-6}$alkyl, $N(C_{1-6}$alkyl$)(C_{1-6}$alkyl$)$, $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl, is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$, or $R^1$ and $R^3$ and/or $R^{1'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$;

$R^4$ is selected from biphenylene, $CH_2$-biphenylene, biphenylene-$CH_2$, $CH_2$-biphenylene-$CH_2$, wherein each biphenylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$ and $C(O)R^5$;

$R^5$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$cycloalkyl, $OC_{6-14}$aryl, $SC_{6-14}$aryl, $C_{1-4}$alkylene $C_{6-14}$aryl, $NH_2$, $NH(C_{1-6}$alkyl$)$ and $N(C_{1-6}$alkyl$)(C_{1-6}$alkyl$)$;

$R^6$ is selected from H and $C_{1-4}$alkyl;

p is 1 or 2;

X is selected from C—$R^7$ and N;

X' is selected from C—$R^{7'}$ and N;

$R^7$ and $R^{7'}$ are independently selected from H, $C_{1-6}$alkyl, $OC_{1-6}$alkyl, $SC_{1-6}$alkyl, $NHC_{1-6}$alkyl, $N(C_{1-6}$alkyl$)(C_{1-6}$alkyl$)$, $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl, is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$, or $R^7$ and $R^3$ and/or $R^{7'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}$alkyl$)(C_{1-6}$alkyl$)$, $NO_2$, $C_{6-10}$aryl, $C_{1-4}$alkylene$C_{6-10}$aryl and $C(O)R^5$; and $Y^-$ and $Y^{'-}$ are, independently, a counter anion, with the proviso that, when $R^4$ is $CH_2$-biphenylene-$CH_2$, $R^1$ is not $CH_2$Ph.

In an embodiment of the disclosure $R^1$ and $R^{1'}$ in the compounds of Formula Ic are independently selected from $C_{1-10}$alkyl, $C_{3-10}$cycloalkyl, $C_{6-10}$aryl and $C_{1-10}$alkylene-$C_{6-10}$aryl, where $C_{1-10}$alkyl, $C_{3-10}$cycloalkyl and $C_{1-10}$alkylene are, independently, unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl$)(C_{1-4}$alkyl$)$, $NO_2$, $=O$ and $=S$ and/or one to three carbon atoms are optionally replaced with a heteroatom independently selected from O, S and $NR^6$, and each $C_{6-10}$aryl is unsubstituted or fluoro-substituted and/or substituted with one to three substituents independently selected from chloro, bromo, iodo, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl$)(C_{1-4}$alkyl$)$ and $NO_2$. In a further embodiment of the disclosure, $R^1$ and $R^{1'}$ in the compounds of Formula Ic are independently selected from $C_{1-4}$alkyl, phenyl and $C_{1-4}$alkylene-phenyl, where $C_{1-4}$alkyl and $C_{1-4}$alkylene are, independently, unsubstituted or fluoro-substituted and/or substituted with one or two groups independently selected from chloro, bromo, iodo, $CH_3$, $OCH_3$, $CF_3$, $OCF_3$, OH, CN, $NH_2$, $NHCH_3$, $N(CH_3)_2$, $NO_2$ and =O and/or one or two carbon atoms are optionally replaced with O, and each phenyl is unsubstituted or fluoro-substituted and/or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$, $NO_2$ and =O. In a further embodiment of the present disclosure, $R^1$ and $R^{1'}$ in the compounds of Formula Ic are independently $C_{1-6}$alkyl or $C_{1-4}$alkylene-phenyl, where phenyl is unsubstituted, fluoro-substituted or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$ and $NO_2$. In a further embodiment, $R^1$ and $R^{1'}$ in the compounds of Formula Ic are the same and are both selected from $CH_3$, $CH_2CH_3$, $(CH_2)_2CH_3$, $CH(CH_3)_2$, $(CH_2)_3CH_3$, $CH_2CH(CH_3)_2$, $C(CH_3)_3$, $CH(CH_3)CH_2CH_3$, $CH_2$-phenyl, $CH_2$-(4-nitrophenyl), $CH_2$-(3-nitrophenyl) and $CH_2$-(2-nitrophenyl).

In another embodiment of the disclosure $R^2$ and $R^{2'}$ in the compounds of Formula Ic are independently selected from H, $C_{1-4}$alkyl, $C_{3-6}$cycloalkyl and $C_{6-10}$aryl, where $C_{1-4}$alkyl, $C_{3-6}$cycloalkyl and $C_{6-10}$aryl are unsubstituted or fluoro-substituted and/or substituted with one to three substituents independently selected from chloro, bromo, iodo, $C_{1-4}$alkyl, $OC_{1-4}$ alkyl, fluoro-substituted $C_{1-4}$alkyl, fluoro-substituted $OC_{1-4}$ alkyl, OH, SH, CN, $NH_2$, $NHC_{1-4}$alkyl, $N(C_{1-4}$alkyl)$(C_{1-4}$ alkyl) and $NO_2$. In a further embodiment $R^2$ and $R^{2'}$ in the compounds of Formula Ic are independently selected from H, $CH_3$, cyclopentyl, cyclohexyl and phenyl, where cyclopentyl, cyclohexyl and phenyl are unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$. In a further embodiment, $R^2$ and $R^{2'}$ in the compounds of Formula Ic are the same and are both selected from H and $CH_3$, suitably H.

In another embodiment of the disclosure $R^3$ and $R^{3'}$ in the compounds of Formula Ic are independently selected from H, $C_{1-4}$alkyl, $OC_{1-4}$alkyl, $SC_{1-4}$alkyl, $NHC_{1-4}$alkyl, $N(C_{1-4}$alkyl)$(C_{1-4}$alkyl), $C_{3-6}$cycloalkyl, $OC_{3-6}$cycloalkyl, $SC_{3-6}$cycloalkyl, $C_{6-10}$aryl, $C_{1-4}$alkylene$C_{6-10}$aryl, $OC_{6-10}$aryl and $SC_{6-10}$aryl, where each $C_{1-4}$alkyl, $C_{1-4}$alkylene, $C_{3-6}$cycloalkyl or $C_{6-10}$aryl is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$ alkyl, OH, SH, CN, $NH_2$, $NHC_{1-4}$alkyl, $N(C_{1-4}$alkyl)$(C_{1-4}$ alkyl) and $NO_2$. In a further embodiment $R^3$ and $R^{3'}$ in the compounds of Formula Ic are independently selected from H, $CH_3$, $OCH_3$, $SCH_3$, $NHCH_3$, $N(CH_3)_2$, cyclopentyl, cyclohexyl, O-cyclopentyl, O-cyclohexyl, phenyl, benzyl, O-phenyl and S-phenyl, where, each phenyl, cyclopentyl and cyclohexyl is unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$. In a further embodiment, $R^3$ and $R^{3'}$ in the compounds of Formula Ic are the same and are both selected from H and $CH_3$, suitably H.

In another embodiment of the disclosure, $R^1$ and $R^3$ and/or $R^{1'}$ and $R^{3'}$ in the compounds of Formula Ic are joined to form, together with the atoms to which they are attached, a monocyclic 5- or 6-membered ring, where the ring is unsaturated and is unsubstituted or fluoro-substituted and/or substituted with one to two substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$. In another embodiment, $R^1$ and $R^3$ and/or $R^{1'}$ and $R^{3'}$ in the compounds of Formula Ic are joined to form, together with the atoms to which they are attached, a monocyclic 5-membered ring, where the ring is unsaturated and is unsubstituted or substituted with one substituent selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In another embodiment, $R^1$ and $R^3$ and $R^{1'}$ and $R^{3'}$ in the compounds of Formula Ic are joined to form, together with the atoms to which they are attached, a monocyclic 5-membered ring, where the ring is unsaturated and is unsubstituted.

In another embodiment of the disclosure, $R^4$ in the compounds of Formula Ic is selected from $R^4$ is selected from biphenylene, $CH_2$-biphenylene, biphenylene-$CH_2$, $CH_2$-biphenylene-$CH_2$, wherein each biphenylene is unsubstituted or fluoro-substituted and/or substituted with one to three substituents independently selected from chlor, bromo, iodo, $C_{1-4}$alkyl, $OC_{1-4}$alkyl, $SC_{1-4}$alkyl, fluoro-substituted $C_{1-4}$alkyl, fluoro-substituted $OC_{1-4}$alkyl, fluoro-substituted $SC_{1-4}$alkyl, OH, SH, CN, $NH_2$, $NHC_{1-4}$alkyl, $N(C_{1-4}$alkyl) $(C_{1-4}$alkyl) and $NO_2$. In another embodiment, $R^4$ in the compounds of Formula Ic is selected from $R^4$ is selected from biphenylene, $CH_2$-biphenylene, biphenylene-$CH_2$, $CH_2$-biphenylene-$CH_2$, wherein each biphenylene is unsubstituted or fluoro-substituted and/or substituted with one to two substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In another embodiment, $R^4$ in the compounds of Formula Ic is selected from $R^4$ is unsubstituted biphenylene.

In a further embodiment of the present disclosure, $R^5$ in the compounds of Formula Ic is selected from H, OH, SH, $C_{1-4}$alkyl, $C_{3-6}$cycloalkyl, $C_{6-10}$aryl, $OC_{1-4}$alkyl, $SC_{1-4}$alkyl, $OC_{3-6}$cycloalkyl, $SC_{3-6}$cycloalkyl, $OC_{6-10}$aryl, $SC_{6-10}$aryl, $NH_2$, $NH(C_{1-4}$alkyl) and $N(C_{1-4}$alkyl)$_2$. In a further embodiment, $R^5$ in the compounds of Formula Ic is selected from H, OH. $CH_3$, cyclopentyl, cyclohexyl, phenyl, $OCH_3$, O-cyclopentyl, O-cyclohexyl, O-phenyl, $NH_2$, $NH(CH_3)$ and $N(CH_3)_2$. In a further embodiment, $R^5$ in the compounds of Formula I is selected from $CH_3$, OH, $OCH_3$, $NH_2$, $NH(CH_3)$ and $N(CH_3)_2$. In a further embodiment, $R^5$ in the compounds of Formula Ic is $CH_3$.

In a further embodiment of the disclosure, $R^6$ in the compound of Formula Ic is selected from H and $CH_3$.

In a further embodiment of the disclosure, X and X' in the compounds of Formula Ic are, independently, C—$R^7$.

In a further embodiment of the disclosure, X and X' in the compounds of Formula Ic are, independently, N.

In a further embodiment of the disclosure, $R^7$ and $R^{7'}$ in the compounds of Formula Ic are independently selected from H, $C_{1-6}$alkyl, $C_{3-6}$cycloalkyl and $C_{6-10}$aryl, where each $C_{1-6}$alkyl, $C_{3-6}$cycloalkyl and $C_{6-10}$aryl is unsubstituted or fluoro-substituted and/or substituted with one to three substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}$alkyl)$(C_{1-4}$alkyl) and $NO_2$. In a further embodiment $R^7$ and $R^{7'}$ in the compounds of Formula Ic are independently selected from H, $CH_3$, cyclopentyl, cyclohexyl and phenyl, where cyclopentyl, cyclohexyl and phenyl are unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$. In a further embodiment, $R^7$ and $R^{7'}$ in the compounds of Formula Ic are the same and are both selected from H and $CH_3$, suitably H.

In another embodiment of the disclosure, $R^7$ and $R^3$ and/or $R^{7'}$ and $R^{3'}$ in the compounds of Formula Ic are joined to form, together with the atoms to which they are attached, a monocyclic 5- or 6-membered ring, where the ring is unsaturated or aromatic and is unsubstituted or fluoro-substituted and/or substituted with one to two substituents independently selected from chloro, bromo, iodo, $C_{1-4}$alkyl, $OC_{1-4}$alkyl, fluoro-substituted $C_{1-4}$alkyl, fluoro-substituted $OC_{1-4}$alkyl, OH, SH, CN, $NH_2$, $NHC_{1-4}$alkyl, $N(C_{1-4}alkyl)(C_{1-4}alkyl)$ and $NO_2$. In another embodiment, $R^7$ and $R^3$ and/or $R^{7'}$ and $R^{3'}$ in the compounds of Formula Ic are joined to form, together with the atoms to which they are attached, a monocyclic 6-membered ring, where the ring is unsaturated or aromatic and is unsubstituted or substituted with one substituent selected from chloro, bromo, iodo, $CH_3$, $OCH_3$, $CF_3$, $OCF_3$, OH, SH, CN, $NH_2$, $NHCH_3$, $N(CH_3)_2$ and $NO_2$. In another embodiment, $R^7$ and $R^3$ and $R^{7'}$ and $R^{3'}$ in the compounds of Formula Ic are joined to form, together with the atoms to which they are attached, an unsubstituted phenyl ring.

In a further embodiment of the disclosure, $Y^-$ and $Y'^-$ in the compounds of Formula Ic are, independently, any suitable counter anion, including, but not limited to, halides (iodide, chloride, bromide or fluoride), sulfates, formates, acetates, alkylsulfonates, aryl sulfonates, borates and phosphates. Suitably the anion is $Cl^-$, $F^-$, $I^-$, $Br^-$ or $BF_4^-$.

It is an embodiment of the disclosure that the two positively charged imidazolium or triazolium rings in the compounds of Formula Ic are the same.

It is a further embodiment of the disclosure that the compounds of Formula Ic are selected from QT98, QT102, QT103, QT110 and QT113, as shown in Table 1, and pharmaceutically acceptable salts, solvates and prodrugs thereof.

In another particular embodiment of the present disclosure, there is included certain novel compounds of Formula II. Accordingly, the present application includes compound selected from a compound of Formula IIa, and pharmaceutically acceptable salts, solvates and prodrugs thereof

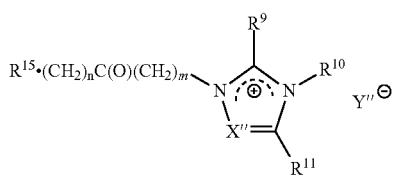

(IIa)

wherein:

$R^9$ is selected from H and phenyl, $R^{10}$ is selected from $C_{1-6}$alkyl;

$R^{11}$ and $R^{15}$ are independently selected from $C_{6-14}$aryl which is unsubstituted or substituted with one or more substituents, independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$ and $C(O)R^{12}$;

$R^{12}$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$cycloalkyl, $OC_{6-14}$aryl, $SC_{6-14}$aryl, $NH_2$, $NH(C_{1-6}alkyl)$ and $N(C_{1-6}alkyl)(C_{1-6}alkyl)$;

n is 0, 1, 2, 3 or 4;

m is 1, 2, 3 or 4;

X" is selected from $C-R^{14}$ and N;

$R^{14}$ is selected from H, $C_{1-10}$alkyl, $C_{3-10}$cycloalkyl and $C_{6-10}$aryl, where each $C_{1-6}$alkyl, $C_{3-10}$cycloalkyl, and $C_{6-14}$aryl are unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$ and $C(O)R^{12}$; and $Y'''^-$ is a counter anion.

It is a further embodiment of the disclosure that the compounds of Formula II are selected from QT58, QT60 and QT93, as shown in Table 1, and pharmaceutically acceptable salts, solvates and prodrugs thereof.

Also included in the present disclosure is one or more compounds of Formula Ia, Ib, Ic and IIa as defined above, and/or pharmaceutically acceptable salts, solvates, and/or prodrugs thereof, for use to prevent or treat an infection by a *Plasmodium* or *Babesia* parasite as well as a use of one or more compounds of Formula Ia, Ib, Ic and IIa as defined above, and/or pharmaceutically acceptable salts, solvates, and/or prodrugs thereof, for use to prevent or treat an invasion of a *Plasmodium* or *Babesia* parasite into an erythrocyte.

Also included in the present disclosure is one or more compounds of Formula Ia, Ib, Ic and IIa as defined above, and/or pharmaceutically acceptable salts, solvates, and/or prodrugs thereof, for use to prepare a medicament to prevent or treat an infection by a *Plasmodium* or *Babesia* parasite as well as a use of one or more compounds of Formula Ia, Ib, Ic and IIa as defined above, and/or pharmaceutically acceptable salts, and/or prodrugs thereof, for use to prepare a medicament to prevent or treat an invasion of a *Plasmodium* or *Babesia* parasite into an erythrocyte.

In a further embodiment of the present disclosure there is also included a compound selected from QT72, QT74, QT75, QT76, QT78, QT79, QT80, QT81, QT82, QT83, QT84, QT92, QT93, QT95, QT97, QT99, QT101, QT107, QT109, QT114, QT116, QT118, QT119 and QT123 as shown in Table 1, and pharmaceutically acceptable salts, solvates, and/or prodrugs thereof. In a further embodiment, there is included a compound that is selected from QT101, QT107, QY109, QT116, QT118, QT119 and QT123 as shown in Table 1, and pharmaceutically acceptable salts, solvates, and/or prodrugs thereof.

In a further embodiment of the present disclosure, there is also included a compound that is:

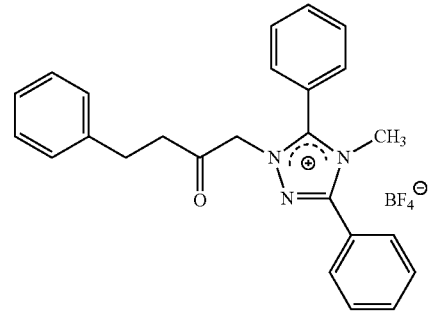

(QT58)

or a pharmaceutically acceptable salt, hydrate or solvate thereof and a compound that is:

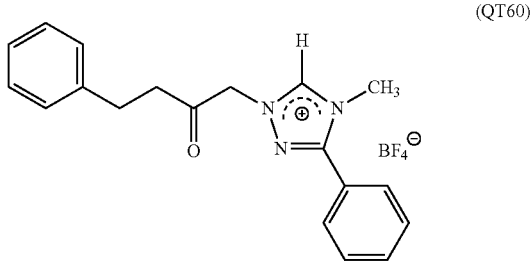

(QT60)

or a pharmaceutically acceptable salt, hydrate or solvate thereof. Also included in the present disclosure is a pharmaceutical composition comprising the compound QT58 or QT60 as shown above and a pharmaceutically acceptable carrier and/or diluent.

IV. Compositions Comprising the Compounds of the Disclosure

The compounds of the disclosure are suitably formulated into pharmaceutical compositions for administration to subjects in a biologically compatible form suitable for administration in vivo. Therefore according to another aspect of the present disclosure, there is included a pharmaceutical composition for the treatment or prevention of an infection by a *Plasmodium* or *Babesia* parasite comprising an effective amount of one or more compounds selected from a compound of the disclosure, and pharmaceutically acceptable salts, solvates, and prodrugs thereof, and a pharmaceutically acceptable carrier or diluent.

In particular embodiments, the present disclosure includes a pharmaceutical composition comprising one or more compounds of Formula Ia, Ib, Ic and IIa as defined above, and/or pharmaceutically acceptable salts, solvates, and/or prodrugs thereof, along with a pharmaceutically acceptable carrier and/or diluent.

In another embodiment, the present disclosure also includes one or more compounds of Formula Ia, Ib, Ic and IIa as defined above, and/or pharmaceutically acceptable salts, solvates, and/or prodrugs thereof, for use as a medicament.

The present disclosure further includes a pharmaceutical composition comprising one or more compounds selected from QT72, QT74, QT75, QT76, QT78, QT79, QT80, QT81, QT82, QT83, QT84, QT92, QT93, QT95, QT97, QT99, QT101, QT107, QT109, QT114, QT116, QT118, QT119 and QT123 as shown in Table 1, and pharmaceutically acceptable salts, solvates, and/or prodrugs thereof, and a pharmaceutically acceptable carrier and/or diluent. In a further embodiment, there is included a pharmaceutical composition comprising one or more compounds selected from QT101, QT107, QY109, QT116, QT118, QT119 and QT123 as shown in Table 1, and pharmaceutically acceptable salts, solvates, and/or prodrugs thereof, and a pharmaceutically acceptable carrier and/or diluent.

The present disclosure also includes one or more compounds selected from QT72, QT74, QT75, QT76, QT78, QT79, QT80, QT81, QT82, QT83, QT84, QT92, QT93, QT95, QT97, QT99, QT101, QT107, QT109, QT114, QT116, QT118, QT119 and QT123 as shown in Table 1, and pharmaceutically acceptable salts, solvates, and/or prodrugs thereof, for use as a medicament. In a further embodiment, there is included a compound that is selected from QT101, QT107, QY109, QT116, QT118, QT119 and QT123 as shown in Table 1, and pharmaceutically acceptable salts, solvates, and/or prodrugs thereof, for use as a medicament.

The term "compound(s) of the disclosure" or "compound(s) of the present disclosure" as used herein means a compound(s) of Formula I, II, Ia, Ib, Ic or IIa, as defined above, including all of the particular embodiments thereof, or salts, solvates or prodrugs thereof. In embodiments, the compounds of present disclosure are used pharmaceutically in the form of salts, solvates and/or as hydrates. All forms are within the scope of the disclosure.

The compositions containing the compounds of the disclosure are prepared by known methods for the preparation of pharmaceutically acceptable compositions which are administered to subjects, such that an effective quantity of the active substance is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

In accordance with embodiments of the methods of the disclosure, the described compounds of the disclosure, are administered to a patient in a variety of forms depending on the selected route of administration, as will be understood by those skilled in the art. In embodiments, the compounds of the disclosure are administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. In an embodiment, parenteral administration is by continuous infusion over a selected period of time.

In an embodiment of the disclosure, the compounds of the disclosure are orally administered, for example, with an inert diluent or with an assimilable edible carrier, or they are enclosed in hard or soft shell gelatin capsules, or they are compressed into tablets, or they are incorporated directly with the food of the diet. For oral therapeutic administration, the compounds of the disclosure are, for example, incorporated with excipient and used in the form of ingestible tablets, buccal tablets, troches, capsules, elixirs, suspensions, syrups, wafers, and the like.

In a further embodiment of the disclosure, the compounds of the disclosure are administered parenterally. Solutions of a compound of the disclosure are, for example, prepared in water suitably mixed with a surfactant such as hydroxypropylcellulose. Dispersions are also prepared, for example, in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

The pharmaceutical forms suitable for injectable use include, for example, sterile aqueous solutions or dispersion and sterile powders for the extemporaneous preparation of sterile injectable solutions or dispersions. In all cases the form must be sterile and must be fluid to the extent that easy syringability exists.

Compositions for nasal administration are, for example, conveniently formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which takes, for example, the form of a cartridge or refill for use with an atomizing device. Alternatively, the sealed container is, for example, a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. The aerosol dosage forms can also take the form of a pump-atomizer.

Compositions suitable for buccal or sublingual administration include, for example, tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

In embodiments, the compounds of the disclosure, are administered to an animal alone or in combination with pharmaceutically acceptable carriers, as noted above, the proportion of which is determined by the solubility and chemical nature of the compound, chosen route of administration and standard pharmaceutical practice.

The dosage of the compounds of the disclosure varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. In an embodiment, the compounds of the disclosure are administered initially in a suitable dosage that is adjusted as required, depending on the clinical response. For ex vivo treatment of cells over a short period, for example for 30 minutes to 1 hour or longer, higher doses of compound are used than for long term in vivo therapy. In an embodiment of the disclosure, dosage forms (compositions suitable for administration) contain from about 0.01 mg to about 1000 mg, suitably about 0.1 mg to about 750 mg, more suitably about 1 mg to about 500 mg, more suitably about 10 mg to about 250 mg, of active ingredient (one or more compounds of the disclosure) per unit. In these pharmaceutical compositions, the active ingredient will ordinarily be present in an amount of about 0.5% to about 95%, suitably 1.0% to about 80%, more suitable about 5.0% to about 50%, weight based on the total weight of the composition.

V. Methods of Preparing the Compounds of the Disclosure

The compounds of the present disclosure are either commercially available or can be prepared using methods known in the art. For example, in as shown in Scheme 1 (Protocol 1), in one embodiment, most of the symmetrical 1,3-disubstituted-imidazolium salts (including QT-68, QT-81, QT-72, QT-74, QT-78-QT-80, QT-82, QT-83, QT-85, QT-90, and QT-92) were synthesized directly by the treatment of imidazole with an excess amount of alkyl halide (including substituted benzyl halides and 2-(bromomethyl)naphthalene) in toluene, following a modification (omission of base) to a previously published procedure (Brenna, S.; Posset, T.; Furrer, J.; Bluemel, J. *Chemistry—A European Journal* 2006, 12, 2880-2888; Starikova, O. V.; Dolgushin, G. V.; Larina, L. I.; Ushakov, P. E.; Komarova, T. N.; Lopyrev, V. A. Russ. *J. Org. Chem.* 2003, 39, 1467-1470). In alternative embodiments, other procedures for the formation of symmetrical 1,3-disubstituted-imidazolium salts are employed: for example compounds QT-91 and QT-97 were prepared (Scheme 1, Protocol 2) by the dialkylation of imidazole with the appropriate α-bromoketone in DMF, (a side-reaction noticed in original attempts at monoalkylation using these very active electrophiles); compound QT-70 was prepared (Scheme 1, Protocol 3) by the alkylation of 1-methylimidazole with iodomethane in a suitable solvent, such as 1-propanol, following a related published procedure (Becker, H. G. O.; Hoffmann, G.; Gwan, K. M.; Knüpfer, L. *Journal fuer Praktische Chemie* 1988, 330, 325-337). Also shown in Scheme 1 (Protocol 3), is another embodiment where the unsymmetrical 1,3-disubstituted-imidazolium salts QT-69, QT-95, QT-75, and QT-73 were prepared by the alkylation of the appropriate 1-substituted imidazole with the appropriate alkyl or benzyl halide in toluene following a similar reported procedure (Chu, Y.; Deng, H.; Cheng, J-P. *J. Org. Chem.* 2007, 72, 7790-7793).

Scheme 1

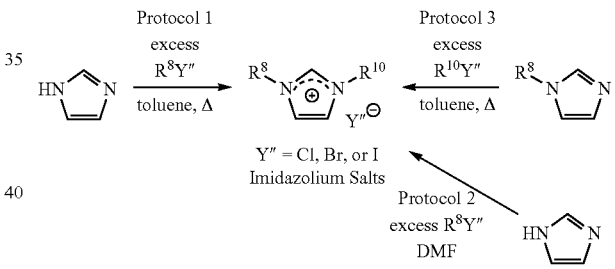

Protocol 1
QT-68 $R^8 = R^{10}$ = benzyl
QT-81 $R^8 = R^{10}$ = (2-naphthalene)methyl
QT-92 $R^8 = R^{10}$ = 4-fluorobenzyl
QT-80 $R^8 = R^{10}$ = 4-chlorobenzyl
QT-72 $R^8 = R^{10}$ = 4-bromobenzyl
QT-78 $R^8 = R^{10}$ = 4-iodobenzyl
QT-74 $R^8 = R^{10}$ = 3-chlorobenzyl
QT-83 $R^8 = R^{10}$ = 3-bromobenzyl
QT-90 $R^8 = R^{10}$ = 2-chlorobenzyl
QT-82 $R^8 = R^{10}$ = 2-bromobenzyl
QT-79 $R^8 = R^{10}$ = 4-methoxybenzyl
QT-85 $R^8 = R^{10}$ = 4-nitrobenzyl Protocol 2
QT-91 $R^8 = R^{10}$ = 2-oxo-2-(4-chlorophenyl)ethyl
QT-97 $R^8 = R^{10}$ = 2-oxo-2-(4-benzylphenyl)ethyl Protocol 3
QT-69 $R^8$ = benzyl, $R^{10}$ = (2-naphthalene)methyl
QT-95 $R^8$ = 4-bromobenzyl, $R^{10}$ = (2-naphthalene)methyl
QT-75 $R^8$ = benzyl, $R^{10}$ = 4-bromobenzyl
QT-73 $R^8$ = methyl, $R^{10}$ = n-propyl
QT-70 $R^8$ = methyl, $R^{10}$ = methyl, 1-propanol as solvent In a further embodiment, as shown in Scheme 2, 1,4-disubstituted-[1,2,4]triazolium salts are prepared by two main protocols. For example, Compound QT-94 was prepared (Scheme 2, Protocol 4) by the alkylation of [1,2,4]triazole using benzyl bromide in $K_2CO_3$-THF, following (by logical extension) similar reported procedures (Owen, C. P.; Patel, C. H.; Dhanani, S.; Ahmed, S. *Letters in Drug Design & Discovery* 2006, 3, 761-765; Owen, C. P.; Dhanani, S.; Patel, C. H.; Shahid, I.; Ahmed, S. *Biorg. Med. Chem. Lett.* 2006, 16, 4011-4015). In another example, compound QT-77 was prepared (Scheme 2, Protocol 4) by the alkylation of [1,2,4] triazole using 4,2'-dibromoacetophenone in DMF. Using a alternative embodiment, compound QT-76 was, for example, prepared (Scheme 2, Protocol 5) by the alkylation of QT-65 (free base form) with benzyl bromide in 1-propanol.

Scheme 2

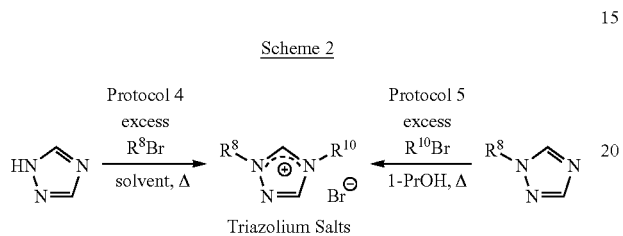

Triazolium Salts

Protocol 4
QT-94 $R^8 = R^{10}$ = benzyl, $K_2CO_3$-THF as solvent
QT-77 $R^8 = R^{10}$ = 2-oxo-2-(4-bromophenyl)ethyl, DMF as solvent Protocol 5
QT-76 $R^8$ = 2-oxo-2-phenylethyl, $R^{10}$ = benzyl In a further embodiment, the synthesis of tri- and tetra-substituted-[1,2,4]triazoles involved the preparation of substituted triazole precursors. Thus, 3,5-diphenyl-[1,2,4]triazole was synthesized by the ring-forming condensation reaction of benzoic hydrazide with benzonitrile (Weidinger, H.; Kranz, J. DE Patent 1958, 1,076,136). 1-Benzyl-3,5-diphenyl-[1,2,4]triazole and 1-(4-bromobenzyl)-3,5-diphenyl-[1,2,4]triazole were prepared by the alkylation of 3,5-diphenyl-[1,2,4]triazole with benzyl bromide and 4-bromobenzyl bromide, respectively, in $K_2CO_3$-DMF (Owen, C. P.; Patel, C. H.; Dhanani, S.; Ahmed, S. *Letters in Drug Design & Discovery* 2006, 3, 761-765). As shown in Scheme 3 (Protocol 6), the 1,3,4-trisubstituted-[1,2,4]triazolium salt QT-60 was synthesized by the methylation of 4-phenyl-1-(3-phenyl-[1,2,4]triazol-1-yl)-butan-2-one in the 4-position using trimethyloxonium tetrafluoroborate in 1,2-dichloroethane following a modification of a similar reported procedure (Lee, L. A.; Evans, R.; Wheeler, J. W. *J. Org. Chem.* 1972, 37, 343-347). Similarly, the 1,3,4,5-tetrasubstituted-[1,2,4]triazolium salts (including QT-84, QT-93, and QT-58) were synthesized by the methylation of the appropriate 1,3,5-trisubstituted-[1,2,4]triazole in the 4-position using trimethyloxonium tetrafluoroborate in 1,2-dichloroethane, as shown in Scheme 3 (Protocol 6). The wide diversity of available starting materials (most notably substituted benzyl halides) allowed control over the nature and position of substituents when designing these imidazolium and triazolium compounds. This flexibility allowed the systematic exploration of structure—activity relationships of several imidazolium and triazolium salts with the goal of finding effective antimalarial candidates.

Scheme 3

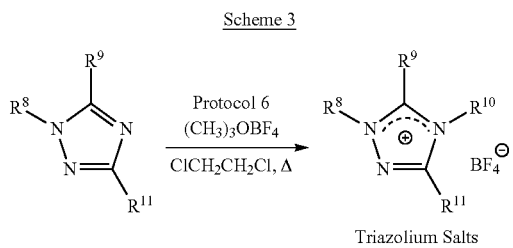

Triazolium Salts

Protocol 6
QT-84 $R^8$ = benzyl, $R^{11}$ = phenyl, $R^{10}$ = methyl, $R^9$ = phenyl
QT-93 $R^8$ = 4-bromobenzyl, $R^{11}$ = phenyl, $R^{10}$ = methyl, $R^9$, phenyl
QT-58 $R^8$ = 2-oxo-4-phenylbutyl, $R^{11}$ = phenyl, $R^{10}$ = methyl, $R^9$ = phenyl
QT-60 $R^8$ = 2-oxo-4-phenylbutyl, $R^{11}$ = phenyl, $R^{10}$ = methyl, $R^9$ = hydrogen In a further embodiment, the bis-imidazole compounds (including QT-126, QT-127, QT-128, QT-129, QT-117, QT-130, QT-108, QT-106, QT-100, and QT-115) containing an alkane linkage were synthesized from the corresponding ω-dihaloalkane (purchased or synthesized) using a nucleophilic displacement reaction of the halide with imidazole, as shown in Scheme 4. The dihydrochloride salt form of these bis-imidazole compounds were tested for anti-malarial activity, although in some cases only the free base was synthesized and tested; these compounds do not contain a permanent positively-charged ring system (unlike their bis-imidazolium salt analogs) and subsequently do not show potent anti-malarial activity. The free base form of these bis-imidazole compounds were converted to the final bis-imidazolium salt compounds (including QT-86, QT-87, QT-71, QT-88, QT-118, QT-89, QT-99, QT-119, QT-109, QT-107, QT-101, and QT-116) by treatment with methyl iodide or other alkyl halide, as shown in Scheme 4.

Scheme 4

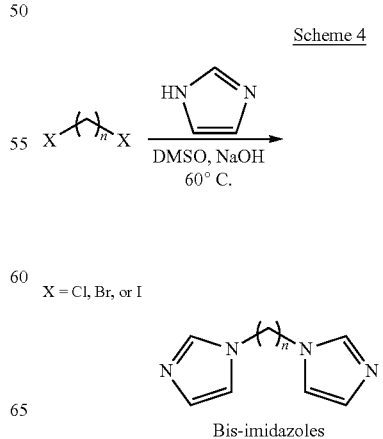

X = Cl, Br, or I

Bis-imidazoles

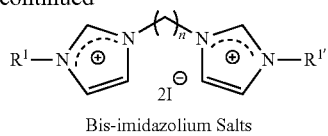

Bis-imidazolium Salts free base form of:
QT-126 n = 4
QT-127 n = 6
QT-128 n = 8
QT 129 n = 10
QT-117 n = 11
QT-130 n =12
QT-108 n = 13
QT-106 n = 14
QT-100 n = 15
QT-115 n = 20

QT-86 n = 4, $R^1$, $R^{1'}$ = $CH_3$
QT-87 n = 6, $R^1$, $R^{1'}$ = $CH_3$
QT-71 n = 8, $R^1$, $R^{1'}$ = $CH_3$
QT-88 n = 10, $R^1$, $R^{1'}$ = $CH_3$
QT-118 n = 12, $R^1$, $R^{1'}$ = $CH_3$
QT-89 n = 12, $R^1$, $R^{1'}$ = $CH_3$
QT-99 n = 12, $R^1$, $R^{1'}$ = $CH_2CH_2$
QT-119 n = 12, $R^1$, $R^{1'}$ = $CH_2CH_2CH_3$
QT-109 n = 13, $R^1$, $R^{1'}$ = $CH_3$
QT-107 n = 14, $R^1$, $R^{1'}$ = $CH_3$
QT-101 n =15, $R^1$, $R^{1'}$ = $CH_3$
QT-116 n = 20, $R^1$, $R^{1'}$ = $CH_3$

Various other bis-imidazole, bis-imidazolium salt, bis-triazole, and bis-triazolium salt compounds were synthesized and are also included (schematic depiction not shown).

A person skilled in the art would appreciate that the above-described reactions can be modified by replacement of any well-known chemical equivalent for another. For example, there are many examples of well known leaving groups, aside from halides, that would be effective in the above-described reactions. As well, a person skilled in the art could vary the identity of solvents, bases, acids, catalyst and the like, to achieve similar chemical transformations. Further, in some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 3$^{rd}$ Edition, 1999. Further reaction temperatures, times and solvents may be adjusted depending on, for example, the physical characteristics and reactivity of the participating reagents, as would be known to those skilled in the art.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the disclosure will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the present disclosure may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine). Some common esters which have been utilized as prodrugs are phenyl esters, aliphatic ($C_1$-$C_{24}$) esters, acyloxymethyl esters, carbamates and amino acid esters.

The present disclosure includes radiolabeled forms of the compounds of the disclosure, for example, compounds of the disclosure labeled by incorporation within the structure of $^3$H, $^{11}$C or $^{14}$C or a radioactive halogen such as $^{125}$I and $^{18}$F. A radiolabeled compound of the disclosure may be prepared using standard methods known in the art. For example, tritium may be incorporated into a compound of the disclosure using standard techniques, for example by hydrogenation of a suitable precursor to a compound of the disclosure using tritium gas and a catalyst. Alternatively, a compound of the disclosure containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo-, suitably iodo-, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C. Further, a compound of the disclosure containing a radioactive fluorine may be prepared, for example, by reaction of K[$^{18}$F]/K222 with a suitable precursor compound, such as a compound of the disclosure comprising a suitable leaving group, for example a tosyl group, that may be displaced with the $^{18}$F anion.

The following non-limiting examples are illustrative of the present disclosure.

VI. Examples

1. Materials and Methods for Synthesis Examples

Flash column chromatography was performed on Silicycle silica gel (230-400 mesh, 60 Å). Analytical thin-layer chromatography was performed on glass-backed precoated silica gel 60 F254 plates (Silicycle), and the compounds were visualized either by UV illumination (254 nm), or by heating after spraying with phosphomolybdic acid in ethanol. Melting points were taken on a MeI-Temp II apparatus and are uncorrected. $^1$H and $^{13}$C NMR spectra were recorded on a Bruker Avance 400 spectrometer in $CDCl_3$, $CD_3OD$, or DMSO-$d_6$. The chemical shifts are reported in d (ppm) relative to tetramethylsilane (Gottlieb, H. E.; Kotlyar, V.; Nudelman, A. *J. Org. Chem.* 1997, 62, 7512). High-resolution ES mass spectra were recorded on a Fisons VG Quattro triple quadrupole mass spectrometer; peaks reported as m/z. All chemical reagents were obtained from Sigma-Aldrich, and were used without further purification.

2.1. Representative Procedure for the Formation of 1-Substituted Imidazoles Precursors 2.1.1. 1-(4-Bromobenzyl)imidazole. Imidazole (400 mg, 5.80 mmol, 1 equiv) was added to a mixture of DMSO (10 mL) and potassium hydroxide (394 mg, 7.05 mmol, 1.2 equiv) and the mixture was stirred for 30 min at 80° C. under an atmosphere of $N_2$. 4-Bromobenzyl bromide (1.76 g, 7.05 mmol, 1.2 equiv) was added and the mixture stirred for 2.5 h at 80° C. After cooling to rt, water was added and the mixture was extracted with ether (2×25 mL). The combined organic phases were washed with water, dried over $Na_2SO_4$ and concentrated. The residue was purified by flash column chromatography on silica gel (30:1 $CHCl_3$—$CH_3OH$ as eluent, then straight CH₃OH) to give the product (680 mg, 2.87 mmol, 49%) as an orange oil; ¹H NMR (400 MHz, DMSO-d₆): δ 5.41 (s, 2H), 7.40 (d, J=8.5 Hz, 2H), 7.63 (d, J=8.5 Hz, 2H), 7.84 (s, 1H), 9.39 (s, 1H); ¹³C NMR (400 MHz, DMSO-d₆): δ 51.3, 119.8, 122.2, 122.9, 130.8, 132.0, 134.0, 136.4; HRMS (EI): Calcd. for $C_{10}H_9N_2Br$ (M)⁺ 235.9949. Found: 235.9940.

2.2. General Procedure for the Formation of Symmetrical Di-Substituted Imidazolium Salts, as Outlined in Scheme 1

Under an atmosphere of $N_2$, a solution of the benzyl or alkyl halide (11.01 mmol, 3 equiv) in toluene (5 mL) was added dropwise to a solution of imidazole (3.67 mmol, 1 equiv) in toluene (10 mL). The mixture was stirred at rt for 30 min and then for 72 h at 70° C. After removing the toluene the crude product was washed with diethyl ether to remove the excess benzyl or alkyl halide. Purification by flash column chromatography on silica gel (9:1 $CH_2Cl_2$—$CH_3OH$) followed by recrystallization from 2-propanol afforded the corresponding symmetrical di-substituted imidazolium salt.

2.3. Characterization of the Compounds Synthesized Following the General Procedure for the Formation of Symmetrical Di-Substituted Imidazolium Salts 2.3.1. 1,3-Dibenzylimidazolium bromide (QT-68). Prepared using imidazole and benzyl bromide as starting materials to give the product (724 mg, 87%) as a clear oil; ¹H NMR (400 MHz, DMSO-d₆): δ 5.43 (s, 4H), 7.39-7.43 (m, 10H), 7.83 (d, J=1.5 Hz, 2H), 9.41 (s, 1H); ¹³C NMR (400 MHz, DMSO-d₆): δ 52.1, 122.9, 128.3, 128.8, 129.0, 134.8, 136.3; HRMS (ESI): Calcd. for $C_{17}H_{17}N_2$ ([M−Br]⁺) 249.1391. Found: 249.1388.

2.3.2. 1,3-Bis-(naphthalen-2-yl-methyl)imidazolium bromide (QT-81). Prepared using imidazole and 2-(bromomethyl)naphthalene as starting materials to give the product (754 mg, 48%) as a white solid; ¹H NMR (400 MHz, DMSO-d₆): δ 5.61 (s, 4H), 7.55-7.58 (m, 7H), 7.90-7.97 (m, 7H), 8.00 (s, 2H), 9.50 (s, 1H); ¹³C NMR (400 MHz, DMSO-d₆): δ 52.3, 123.1, 125.7, 126.8, 127.6, 127.7, 127.9, 128.8, 132.2, 132.7, 132.8, 136.6; HRMS (ESI) Calcd. for $C_{25}H_{21}N_2$ ([M−Br]⁺) 349.1704. Found: 349.1700.

2.3.3. 1,3-Bis-(4-fluorobenzyl)imidazolium bromide (QT-92). Prepared using imidazole and 4-fluorobenzyl bromide as starting materials to give the product (737 mg, 55%) as an off-white oil; ¹H NMR (400 MHz, DMSO-d₆): δ 5.40 (s, 4H), 7.24-7.29 (m, 4H), 7.49-7.52 (m, 4H), 7.80 (d, J=1.4 Hz, 2H), 9.36 (s, 1H); ¹³C NMR (400 MHz, DMSO-d₆): δ 51.4, 115.9, 116.1, 122.9, 131.0, 131.1, 136.2; HRMS (ESI): Calcd. for $C_{17}H_{15}F_2N_2$ ([M−Br]⁺) 285.1203. Found: 285.1196.

2.3.4. 1,3-Bis-(4-chlorobenzyl)imidazolium chloride (QT-80). Prepared using imidazole and 4-chlorobenzyl chloride as starting materials to give the product (150 mg, 12%) as a white sticky solid; ¹H NMR (400 MHz, DMSO-d₆): δ 5.48 (s, 4H), 7.49-7.50 (m, 10H), 7.89 (d, J=1.4 Hz, 2H), 9.68 (s, 1H); ¹³C NMR (400 MHz, DMSO-d₆): δ 51.1, 122.9, 129.0, 130.5, 133.5, 133.8, 136.6; HRMS (ESI): Calcd. for $C_{17}H_{15}Cl_2N_2$ ([M−Cl]⁺) 317.0612. Found: 317.0628.

2.3.5. 1,3-Bis-(4-bromobenzyl)imidazolium bromide (QT-72). Prepared using imidazole and 4-bromobenzyl bromide as starting materials to give the product (263 mg, 47%) as a white solid; ¹H NMR (400 MHz, DMSO-d₆): δ 5.43 (s, 4H), 7.40 (d, J=8.5 Hz, 4H), 7.60 (d, J=8.5 Hz, 4H), 7.85 (d, J=1.6 Hz, 2H), 9.43 (s, 1H); ¹³C NMR (400 MHz, DMSO-d₆): δ 51.3, 122.2, 122.9, 130.7, 131.9, 134.0, 136.4; HRMS (ESI): Calcd. for $C_{17}H_{15}Br_2N_2$ ([M−Br]⁺) 404.9601. Found: 404.9571.

2.3.6. 1,3-Bis-(4-iodobenzyl)imidazolium bromide (QT-78). Prepared using imidazole and 4-iodobenzyl bromide as starting materials to give the product (66 mg, 28%) as a white solid; ¹H NMR (400 MHz, DMSO-d₆): δ 5.39 (s, 4H), 7.22 (d, J=8.3 Hz, 4H), 7.79 (d, J=8.3 Hz, 4H), 7.82 (d, J=1.5 Hz, 2H), 9.38 (s, 1H); ¹³C NMR (400 MHz, DMSO-d₆): δ 51.4, 95.4, 122.9, 130.6, 134.3, 136.4, 137.7; HRMS (ESI): Calcd. for $C_{17}H_{15}BrI_2N_2$ ([M−Br]⁺) 500.9324. Found: 500.9327.

2.3.7. 1,3-Bis-(3-chlorobenzyl)imidazolium bromide (QT-74). Prepared using imidazole and 3-chlorobenzyl bromide as starting materials to give the product (1.00 g, 68%) as a white solid; ¹H NMR (400 MHz, DMSO-d₆): δ 5.45 (s, 4H), 7.38-7.43 (m, 2H), 7.45-7.48 (m, 4H), 7.55 (s, 2H), 7.85 (d, J=1.4 Hz, 2H), 9.41 (s, 1H); ¹³C NMR (400 MHz, DMSO-d₆): δ 51.3, 122.9, 127.2, 128.4, 128.8, 130.9, 133.5, 136.6, 137.0; HRMS (ESI): Calcd for $C_{17}H_{15}Cl_2N_2$ ([M−Br]⁺) 317.0612. Found: 317.0601.

2.3.8. 1,3-Bis-(3-bromobenzyl)imidazolium bromide (QT-83). Prepared using imidazole and 3-bromobenzyl bromide as starting materials to give the product (581 mg, 32%) as a white solid; ¹H NMR (400 MHz, DMSO-d₆): δ 5.43 (s, 4H), 7.38-7.45 (m, 4H), 7.60-7.62 (m, 2H), 7.69 (s, 2H), 7.85 (d, J=1.4 Hz, 2H), 9.39 (s, 1H); ¹³C NMR (400 MHz, DMSO-d₆): δ 51.3, 122.1, 123.0, 127.6, 131.2, 131.2, 131.7, 136.7, 137.3; HRMS (ESI): Calcd. for $C_{17}H_{15}Br_2N_2$ ([M−Br]⁺) 404.9601. Found: 404.961.

2.3.9. 1,3-Bis-(2-chlorobenzyl)imidazolium bromide (QT-90). Prepared using imidazole and 2-chlorobenzyl bromide as starting materials to give the product (660 mg, 45%) as a white solid; ¹H NMR (400 MHz, DMSO-d₆): δ 5.59 (s, 4H), 7.45-7.48 (m, 6H), 7.55-7.57 (m, 2H), 7.82 (d, J=1.4 Hz, 2H), 9.44 (s, 1H); ¹³C NMR (400 MHz, DMSO-d₆): δ 50.2, 123.1, 128.0, 129.9, 130.9, 131.0, 131.9, 132.9, 137.4; HRMS (ESI): Calcd. for $C_{17}H_{15}Cl_2N_2$ ([M−Br]⁺) 317.0612. Found: 317.0613.

2.3.10. 1,3-Bis-(2-bromobenzyl)imidazolium bromide (QT-82). Prepared using imidazole and 2-bromobenzyl bromide as starting materials to give the product (846 mg, 47%) as a beige solid; ¹H NMR (400 MHz, DMSO-d₆): δ 5.56 (s, 4H), 7.36-7.40 (m, 4H), 7.47-7.51 (m, 2H), 7.73 (d, J=7.9 Hz, 2H), 7.81 (d, J=1.4 Hz, 2H), 9.37 (s, 1H); ¹³C NMR (400 MHz, DMSO-d₆): δ 52.4, 123.1, 123.2, 128.5, 130.7, 131.1, 133.2, 133.5, 137.5; HRMS (ESI): Calcd. for $C_{17}H_{15}Br_2N_2$ ([M−Br]⁺) 404.9601. Found: 404.9616.

2.3.11. 1,3-Bis-(4-methoxybenzyl)imidazolium chloride (QT-79). Prepared using imidazole and 4-methoxybenzyl chloride as starting materials to give the product (550 mg, 43%) as a white solid; ¹H NMR (400 MHz, DMSO-d₆): δ 3.76 (s, 3H), 5.32 (s, 4H), 6.96 (d, J=8.6 Hz, 4H), 7.37 (d, J=8.6 Hz, 4H), 7.58 (d, J=1.5 Hz, 2H), 9.32 (s, 1H); ¹³C NMR (400 MHz, DMSO-d₆): δ 51.6, 55.2, 114.4, 122.6, 129.5, 130.2, 135.7, 159.6; HRMS (ESI): Calcd. for $C_{19}H_{21}N_2O_2$ ([M−Cl]⁺) 309.1603. Found: 309.1617.

2.3.12. 1,3-Bis-(4-nitrobenzyl)imidazolium bromide (QT-85). Prepared using imidazole and 4-nitrobenzyl bromide as starting materials to give the product (731 mg, 47%) as a white solid; ¹H NMR (400 MHz, DMSO-d₆): δ 5.62 (s, 4H), 7.66 (d, J=8.5 Hz, 4H), 7.9 (d, J=0.9 Hz, 2H), 8.29 (d, J=8.5 Hz, 4H), 9.45 (s, 1H); ¹³C NMR (400 MHz, DMSO-d₆): δ 51.2, 123.3, 124.1, 129.6, 137.3, 141.9, 147.7; HRMS (ESI): Calcd. for $C_{17}H_{15}N_4O_4$ ([M−Br]⁺) 339.1093. Found: 339.110.

2.4. Alternative Procedures for the Formation of Symmetrical Di-Substituted Imidazolium Salts, as Outlined in Scheme 1

2.4.1. 1,3-Bis-[2-oxo-2-(4-chlorophenyl)ethyl]imidazolium bromide (QT-91).

Under an atmosphere of $N_2$, 2'-bromo-4-chloroacetophenone (3.50 g, 15 mmol, 1 equiv) was dissolved in DMF (15 mL) and to this was added imidazole (3.06 g, 45 mmol, 3 equiv). The mixture was stirred at rt for 3 h, then slowly poured into water (250 mL). After stirring for 0.5 h, the resulting white precipitate was removed by filtration, and the solid was washed with boiling toluene (100 mL) to remove the monoalkylated product (also desired). The toluene insoluble material was dried under high vacuum and then recrystallized from 1:1 MeOH-EtOH. The solid was removed by filtration and washed with EtOH. High-vacuum drying gave QT-91 (438 mg, 0.96 mmol, 13%) as a white solid: mp>260° C.; $^1$H NMR (400 MHz, DMSO-$d_6$): δ 6.17 (s, 4H), 7.74 (d, J=8.4 Hz, 4H), 7.80 (s, 2H), 8.09 (d, J=8.4 Hz, 4H), 9.09 (s, 1H); $^{13}$C NMR (100 MHz, DMSO-$d_6$): δ 55.6, 123.7, 129.2, 130.0, 132.5, 138.5, 139.3, 190.5; HRMS (ESI): Calcd. for $C_{19}H_{15}Cl_2N_2O_2$ ([M−Br]$^+$) 373.0510. Found: 373.0488.

2.4.2. 1,3-Bis-[2-oxo-2-(4-benzylphenyl)ethyl]imidazolium bromide (QT-97).

Under an atmosphere of $N_2$, 4'-benzyl-2-bromoacetophenone (1.21 g, 4.18 mmol, 1 equiv) was dissolved in DMF (5 mL) and to this was added imidazole (0.85 g, 12.49 mmol, 3 equiv). The mixture was stirred at rt for 3 h, then slowly poured into water (100 mL). After stirring for 0.5 h, the resulting white precipitate was removed by filtration, and the solid was washed with boiling toluene (50 mL) to remove the monoalkylated product (also desired). The toluene insoluble material was dried under high vacuum and then recrystallized from EtOH (5 mL). The solid was removed by filtration and washed with EtOH (1 mL). High-vacuum drying gave QT-97 (131 mg, 0.23 mmol, 11%) as a white solid: mp 215-217° C.; $^1$H NMR (400 MHz, DMSO-$d_6$): δ 4.07 (s, 4H), 6.11 (s, 4H), 7.18-7.34 (m, 10H), 7.50 (d, J=8.4 Hz, 4H), 7.76 (d, J=1.2 Hz, 2H), 7.99 (d, J=8.0 Hz, 4H), 9.08 (s, 1H); $^{13}$C NMR (100 MHz, DMSO-$d_6$): δ 41.0, 55.5, 123.7, 126.3, 128.5, 128.6, 128.8, 129.4, 131.8, 138.6, 140.4, 148.5, 190.8; HRMS (ESI): Calcd. for $C_{33}H_{29}N_2O_2$ ([M−Br]$^+$) 485.2229. Found: 485.2219.

2.4.3. 1,3-Dimethylimidazolium iodide (QT-70).

1-Methylimidazole (202 mg, 2.46 mmol, 1 equiv) was dissolved in 1-propanol (2 mL) at rt and to this was added iodomethane (0.31 mL, 4.98 mmol, 2 equiv). The mixture was heated at 100° C. for 19 h, then cooled to 0° C. $Et_2O$ was slowly added with stirring resulting in a yellow precipitate that was removed by filtration and washed with $Et_2O$ (3×) and also with EtOAc (5×). High-vacuum drying gave QT-70 (470 mg, 2.10 mmol, 85%) as a yellow solid: mp 78-80° C.; $^1$H NMR (400 MHz, CD$_3$OD): δ 3.93 (s, 6H), 7.56 (s, 2H), 8.87 (s, 1H); $^{13}$C NMR (100 MHz, CD$_3$OD): δ 36.6, 124.8, 138.6; HRMS (ESI): Calcd. for $C_4H_7N_2$ ([M−I−CH$_2$]$^+$) 83.0609. Found: 83.0593.

2.5. General Procedure for the Formation of Unsymmetrical Di-Substituted Imidazolium Salts, as Outlined in Scheme 1

Under an atmosphere of $N_2$, the benzyl or alkyl halide (4.40 mmol, 1.2 equiv) in toluene (5 mL) was added dropwise to a solution of 1-benzylimidazole, 1-methylimidazole, or another 1-substituted imidazole (3.67 mmol, 1 equiv) in toluene (10 mL). The mixture was stirred for 30 min at room temperature and then for 72 h at 70° C. After removing the toluene, the crude product was washed with diethyl ether to remove the excess benzyl or alkyl bromide. Recrystallization from 2-propanol gave the corresponding unsymmetrical di-substituted imidazolium salt.

2.6. Characterization of the Compounds Synthesized Following the General Procedure for the Formation of Unsymmetrical Di-Substituted Imidazolium Salts

2.6.1. 1-Benzyl-3-(naphthalen-2-yl-methyl)imidazolium bromide (QT-69).

Prepared using 1-benzylimidazole and 2-(bromomethyl)naphthalene as starting materials to give the product (46 mg, 32%) as a white solid; $^1$H NMR (400 MHz, CD$_3$OD): δ 5.43 (s, 2H), 5.60 (s, 2H), 7.41-7.45 (m, 5H), 7.47 (dd, J=2 Hz, 1H), 7.52-7.56 (m, 1H), 7.64-7.69 (m, 1H), 7.88-7.93 (m, 3H), 7.94 (s, 1H), 7.96 (s, 1H), 9.26 (s, 1H); $^{13}$C NMR (400 MHz, CD$_3$OD): δ 54.3, 54.4, 124.1, 124.2, 126.5, 128.0, 128.1, 128.9, 129.1, 129.4, 129.7, 130.4, 130.5, 132.4, 134.8, 134.9, 135.2, 137.7; HRMS (ESI): Calcd. for $C_{21}H_{19}N_2$ ([M−Br]$^+$) 299.1548. Found: 299.1553.

2.6.2. 1-(4-Bromobenzyl)-3-(naphthalen-2-ylmethyl)imidazolium bromide (QT-95).

Prepared using 1-(4-bromobenzyl)imidazole and 2-(bromomethyl)naphthalene as starting materials, recrystallized from 2:1 2-propanol-Et$_2$O to give the product (312 mg, 64%) as a yellow-brown oil; $^1$H NMR (400 MHz, DMSO-$d_6$): δ 5.43 (s, 2H), 5.60 (s, 2H), 7.39 (d, J=8.5 Hz, 2H), 7.52-7.58 (m, 3H), 7.63 (d, J=8.5 Hz, 2H), 7.84 (s, 1H), 7.88 (s, 1H), 7.91-7.99 (m, 4H), 9.43 (s, 1H); $^{13}$C NMR (400 MHz, DMSO-$d_6$): δ 51.3, 52.3, 122.1, 122.8, 123.0, 125.7, 126.7, 126.7, 127.6, 127.8, 128.8, 130.6, 131.9, 131.9, 132.7, 132.7, 134.0, 136.5; HRMS (ESI): Calcd. for $C_{21}H_{18}BrN_2$ ([M−Br]$^+$) 377.0653. Found: 377.0641.

2.6.3. 1-Benzyl-3-(4-bromobenzyl)imidazolium bromide (QT-75).

Prepared using 1-benzylimidazole and 4-bromobenzyl bromide as starting materials to give the product (330 mg, 51%) as a beige solid; $^1$H NMR (400 MHz, CD$_3$OD): δ 5.44 (s, 2H), 5.45 (s, 2H), 7.38-7.436 (m, 4H), 7.63-7.65 (m, 4H), 7.86 (d, J=1.6 Hz, 2H), 9.47 (s, 1H); $^{13}$C NMR (400 MHz, CD$_3$OD): δ 51.2, 52.0, 122.2, 122.8, 122.9, 128.4, 128.8, 129.0, 130.7, 131.9, 134.1, 134.7, 136.3; HRMS (ESI): Calcd. for $C_{17}H_{16}BrN_2$ ([M−Br]$^+$) 327.0496. Found: 327.0513.

2.6.4. 3-Methyl-1-propylimidazolium bromide (QT-73).

Prepared using 1-methylimidazole and 1-bromopropane as starting materials to give the product (519 mg, 83%) as an orange oil; $^1$H NMR (400 MHz, CD$_3$OD): δ 0.96 (t, J=7.4 Hz, 3H), 1.88 (m, 2H), 3.96 (s, 3H), 4.19 (t, J=7.2 Hz, 2H), 7.60 (s, 1H), 7.67 (s, 1H), 9.02 (s, 1H); $^{13}$C NMR (400 MHz, CD$_3$OD): δ 10.9, 24.5, 36.6, 52.3, 123.7, 125.0, 137.9; HRMS (ESI): Calcd. for $C_9H_{13}N_2$ ([M−Br]$^+$) 125.1078. Found: 125.1084.

2.7. Representative Procedures for the Formation of 1,4-Disubstituted-[1,2,4]Triazolium Salts, as Outlined in Scheme 2

2.7.1. 1,4-Dibenzyl-[1,2,4]triazolium bromide (QT-94).

Under a atmosphere of $N_2$, a mixture of [1,2,4]-triazole (500 mg, 14.40 mmol) and potassium carbonate (426 mg, 3.09 mmol) in THF (10 mL) was stirred at it for 10 min. To this was added benzyl bromide (5.00 g, 28.80 mmol) dropwise and the mixture stirred at reflux temperature for 48 h. After cooling to rt, the white precipitate formed was removed by filtration and the filtrate kept was concentrated to a yellow oil. The oil was treated with dichloromethane and the resulting precipitate was removed by filtration. Recrystallization from 2-propanol gave QT-94 (530 mg, 34.6%) as a white solid; $^1$H NMR (400

MHz, DMSO-$d_6$): δ 5.52 (s, 2H), 5.61 (s, 2H), 7.40-7.51 (m, 10H), 9.33 (s, 1H), 10.32 (s, 1H); $^{13}$C NMR (400 MHz, DMSO-$d_6$): δ 50.65, 54.89, 128.82, 128.87, 128.91, 128.96, 129.09, 133.13, 133.5, 142.74, 145.0; HRMS (ESI): Calcd. for $C_{16}H_{16}N_3$ ([M−Br]$^+$) 250.1344. Found: 250.1341.

2.7.2. 4-Benzyl-1-(2-oxo-2-phenylethyl)[1,2,4]triazolium bromide (QT-76). The hydrochloride salt QT-65 (132 mg, 0.59 mmol) was dissolved in water (~5 mL) and the solution basified with excess $K_2CO_3$ (~132 mg, 0.96 mmol). The mixture was extracted with EtOAc (3×), and the combined organic extracts were dried ($Na_2SO_4$), concentrated, and dried under high vacuum leaving the free base (112 mg, 0.59 mmol, 100%). The free base (112 mg, 0.59 mmol, 1 equiv) was dissolved in 1-propanol (2 mL) at rt and to this was added benzyl bromide (0.1 mL, 0.84 mmol, 1.4 equiv). The mixture was heated at reflux temperature for 4 h, then cooled to 0° C. $Et_2O$ was added, and the resulting precipitate was removed by filtration, washed with $Et_2O$ (10×), and dried under high vacuum. Purification by flash column chromatography on silica gel (9:1 $CHCl_3$-MeOH as eluent) gave QT-76 (24 mg, 0.07 mmol, 12%) as a beige solid: mp 166-170° C.; $^1$H NMR (400 MHz, DMSO-$d_6$): δ 5.66 (s, 2H), 6.31 (s, 2H), 7.40-7.55 (m, 5H), 7.63 (app t, J=7.8 Hz, 2H), 7.77 (app t, J=7.4 Hz, 1H), 8.00-8.10 (m, 2H), 9.45 (s, 1H), 10.22 (s, 1H); $^{13}$C NMR (100 MHz, DMSO-$d_6$): δ 50.9, 58.4, 128.5, 128.8, 129.3, 129.4 (2C), 133.5, 133.7, 134.9, 144.4, 144.9, 190.6; HRMS (ESI): Calcd. for $C_{17}H_{16}N_3O$ ([M−Br]$^+$) 278.1293. Found: 278.1283.

2.7.3. 1,4-Bis-[2-oxo-2-(4-bromophenyl)ethyl]-[1,2,4] triazolium bromide (QT-77). Under an atmosphere of $N_2$, 4,2'-dibromoacetophenone (1.12 g, 4 mmol, 1 equiv) was dissolved in DMF (6 mL) and to this was added 1,2,4-triazole (828 mg, 12 mmol, 3 equiv). The mixture was stirred at rt for 3 h, then water was added. The resulting white precipitate was removed by filtration, and the solid was washed with boiling benzene (50 mL) to remove the monoalkylated product. The benzene insoluble material was dried under high vacuum and then purified by flash column chromatography on silica gel (9:1 EtOAc-MeOH as eluent). The yellowish solid obtained was washed once with rt MeOH to remove the yellow color. Recrystallization from MeOH gave QT-77 (100 mg, 0.18 mmol, 9%) as a white solid: mp 244-245° C.; $^1$H NMR (400 MHz, DMSO-$d_6$): δ 6.20 (s, 2H), 6.40 (s, 2H), 7.80-7.92 (m, 4H), 7.95-8.08 (m, 4H), 9.24 (s, 1H), 10.08 (s, 1H); $^{13}$C NMR (100 MHz, DMSO-$d_6$): δ 54.3, 58.5, 129.0, 129.1, 130.3, 130.4, 132.3, 132.4 (2C), 132.6, 145.4, 145.9, 189.8, 189.9; HRMS (ESI): Calcd. for $C_{18}H_{14}Br_2N_3O_2$ ([M−Br]$^+$) 461.9452. Found: 461.9440.

2.8. Representative Procedure for the Formation of 3,5-Disubstituted-[1,2,4]Triazoles 2.8.1. 3,5-Diphenyl-[1,2,4]triazole. Under an atmosphere of $N_2$, a mixture of benzoic hydrazide (4.00 g, 29.30 mmol, 1 equiv) and benzonitrile (39.60 g, 384.00 mmol, 13.1 equiv) was stirred at reflux temperature for 14 h in a round bottom flask equipped with a Dean Stark apparatus to remove water. The mixture was cooled to rt, and the resulting precipitate collected by filtration and washed with 2-propanol. Recrystallization from 2-propanol gave the product (3.77 g, 58%) as a white solid; $^1$H NMR (400 MHz, DMSO-$d_6$): δ 7.41-7.59 (m, 6H), 8.07-8.10 (m, 2H), 8.12 (1s, 1H); $^{13}$C NMR (400 MHz, DMSO-$d_6$): δ 125.9, 126.1, 128.7, 129.1, 130.2, 131.3; HRMS (EI): Calcd. for $C_{14}H_{11}N_3$ (M$^+$) 221.0953. Found: 221.0948.

2.9. Representative Procedures for the Formation of 1,3,5-Trisubstituted-[1,2,4]Triazoles 2.9.1. 1-Benzyl-3,5-diphenyl-[1,2,4]triazole. Under an atmosphere of $N_2$, a mixture of 3,5-diphenyl-[1,2,4]triazole (250 mg, 1.13 mmol) and potassium carbonate (471 mg, 3.39 mmol) in DMF (5 mL) was stirred at 75° C. for 1 h. To this was added a solution of benzyl bromide (386 mg, 2.26 mmol) in DMF (3 mL) and the mixture heated at reflux temperature with stirring for 48 h. The progress of the reaction was monitored by TLC. The mixture was cooled to rt, diluted with EtOAc (25 mL), and the organic layer washed sequentially with water (2×25 mL) and a saturated aqueous solution of $NaHCO_3$ (2×25 mL), dried ($Na_2SO_4$), and concentrated to a beige solid. Recrystallization from hexanes gave the product (282 mg, 3.2 mmol, 80%) as a white solid; $^1$H NMR (400 MHz, $CDCl_3$): δ 7.41-7.59 (m, 6H), 8.07-8.10 (m, 2H), 8.12 (1s, 1H); $^{13}$C NMR (400 MHz, DMSO-$d_6$): δ 52.4, 120.9, 125.8, 126.8, 127.6, 127.8, 128.5, 128.8, 129.0, 129.3, 130.3, 130.7, 136.3, 155.6, 160.3; HRMS (EI): Calcd. for $C_{21}H_{17}N_3$ (M$^+$) 311.1422. Found: 311.1426.

2.9.2. 1-(4-Bromobenzyl)-3,5-diphenyl-[1,2,4]triazole. Under an atmosphere of $N_2$, a mixture of 3,5-diphenyl-[1,2,4]triazole (500 mg, 2.26 mmol) and potassium carbonate (942 mg, 6.78 mmol) in DMF (10 mL) was stirred at 75° C. for 1 h. To this was added a solution of 4-bromobenzyl bromide (1.41 g, 5.65 mmol) in DMF (3 mL) and the mixture was stirred at reflux temperature for 48 h. The progress of the reaction was monitored by TLC. The mixture was cooled to rt, diluted with EtOAc (25 mL), and the organic layer washed sequentially with water (2×25 mL) and a saturated aqueous solution of $NaHCO_3$ (2×25 mL), dried ($Na_2SO_4$), and concentrated to an orange oil. Purification by flash column chromatography on silica gel (chloroform as eluent to remove impurities, followed by elution of the product with methanol) gave the product (563 mg, 64%) as an orange oil: $^1$H NMR (400 MHz, DMSO-$d_6$): δ 5.55 (s, 2H), 7.11 (d, J=8.3 Hz, 2H), 7.44-7.56 (m, 8H), 7.7-7.72 (m, 2H), 8.05 (s, 1H), 8.072-8.074 (d, J=1 Hz, 1H); $^{13}$C NMR (400 MHz, DMSO-$d_6$): δ 51.79, 120.92, 125.85, 127.48, 128.52, 128.75, 128.98, 129.1, 129.31, 130.34, 130.64, 131.66, 135.7, 155.6, 160.42; HRMS (EI): Calcd. for $C_{21}H_{16}N_3Br$ (M$^+$) 389.0528. Found: 389.0536.

2.10. Representative Procedures for the Formation of 1,3,4,5-Tetrasubstituted [1,2,4]Triazolium Salts, as Outlined in Scheme 3

2.10.1. 1-Benzyl-4-methyl-3,5-diphenyl-[1,2,4]triazolium tetrafluoroborate (QT-84). Under an atmosphere of $N_2$, 1-benzyl-3,5-diphenyl-[1,2,4]triazole (200 mg, 0.64 mmol) was dissolved in 1,2-dichlorethane (2 mL). To this was added a solution of trimethyloxonium tetrafluoroborate (104 mg, 0.70 mmol) in 1,2-dichlorethane (1 mL) and the mixture was heated at 65° C. with stirring for 5 h. The progress of the reaction was monitored by TLC (9:1 $CH_2Cl_2$—$CH_3OH$ as eluent). The mixture was concentrated to a clear oil that was purified by flash column chromatography on silica gel (chloroform as eluent to remove impurities, followed by elution of the product with methanol). High-vacuum drying gave QT-84 (175 mg, 66%) as a white solid: $^1$H NMR (400 MHz, DMSO-$d_6$): δ 3.66 (s, 3H), 5.55 (s, 2H), 7.26-7.28 (m, 2H), 7.36-7.38 (m, 3H), 7.69-7.87 (m, 10H); $^{13}$C NMR (400 MHz, DMSO-$d_6$): δ 34.6, 54.1, 119.3, 123.1, 128.1, 128.7, 128.8, 129.4, 129.5, 129.8, 130.2, 132.2, 133.3, 133.5, 152.3, 154.0; HRMS (ESI): Calcd. for $C_{22}H_{20}BF_4N_3$ ([M−$BF_4$]$^+$) 326.1657. Found: 326.166.

2.10.2. 1-(4-Bromobenzyl)-4-methyl-3,5-diphenyl-[1,2,4]triazolium tetrafluoroborate (QT-93). Under an atmosphere of $N_2$, 1-(4-bromobenzyl)-3,5-diphenyl-[1,2,4]triazole (300 mg, 0.77 mmol) was dissolved in 1,2-dichlorethane (5 mL) and to this was added a solution of trimethyloxonium tetrafluoroborate (136 mg, 0.92 mmol) in 1,2-dichlorethane (2 mL). The mixture was heated at 65° C. with stirring for 10 h. The progress of the reaction was monitored by TLC (9:1 $CH_2Cl_2$—$CH_3OH$ as eluent). The mixture was concentrated to a clear oil. Purification by flash column chromatography on silica gel (chloroform as eluent to remove impurities, followed by elution of the product with methanol) gave QT-93 (184 mg, 49%) as a white solid: $^1H$ NMR (400 MHz, DMSO-$d_6$): δ 3.66 (s, 3H), 5.54 (s, 2H), 7.24 (d, J=8.1 Hz, 2H), 7.57 (d, J=8.1 Hz, 3H), 7.71-7.84 (m, 8H), 7.86 (d, J=0.7 Hz, 2H); $^{13}C$ NMR (400 MHz, DMSO-$d_6$): δ 34.58, 53.35, 119.21, 121.99, 123.03, 129.35, 129.46, 129.84, 130.19, 130.43, 131.64, 132.27, 132.65, 133.51, 152.42, 154, 08; HRMS (ESI): Calcd. for $C_{22}H_{19}BrBF_4N_3$ ([M−$BF_4$]$^+$) 404.0762. Found: 404.0771.

2.10.3. 4-Methyl-1-(2-oxo-4-phenylbutyl)-3,5-diphenyl-[1,2,4]triazolium tetrafluoroborate (QT-58). Under an atmosphere of $N_2$, 1-(3,5-diphenyl-[1,2,4]triazol-1-yl)-4-phenyl-butan-2-one (107 mg, 0.29 mmol, 1 equiv) was dissolved in 1,2-dichloroethane (2 mL) and to this was added trimethyloxonium tetrafluoroborate (46 mg, 0.31 mmol, 1.07 equiv). The vial containing the borate was rinsed with 1,2-dichloroethane (1 mL) and the rinse solution added to the reaction mixture. The mixture was heated at 65° C. with stirring for 3.5 h, and then concentrated to a golden oil. High-vacuum drying left a foamy white solid which was purified by flash chromatography on silica gel (load and wash with $CHCl_3$, then elute baseline product with EtOAc) gave QT-58 (49 mg, 0.10 mmol, 34%) as a clear oil: $R_f$=0 ($CHCl_3$); $^1H$ NMR (400 MHz, $CD_3OD$): δ 2.82-2.93 (m, 4H), 3.76 (s, 3H), 5.42 (s, 2H), 7.08-7.25 (m, 5H), 7.60-7.95 (m, 10H); $^{13}C$ NMR (100 MHz, $CD_3OD$): δ 30.0, 35.3, 42.2, 60.4, 120.3, 124.4, 127.3, 129.3, 129.5, 130.5, 130.7, 131.0, 131.2, 133.5, 135.0, 141.5, 155.3, 156.4, 201.8; $^1H$-$^1H$ NOESY: no observable NOE between protons at 5.42 ppm and the protons at 3.76 ppm which confirms methylation in the 4-position; HRMS (ESI): Calcd. for $C_{25}H_{24}N_3O$ ([M−$BF_4$]$^+$) 382.1919. Found: 382.1903.

2.11. Representative Procedure for the Formation of 1,3,4-Trisubstituted[1,2,4]Triazolium Salts, as Outlined in Scheme 3

2.11.1. 4-Methyl-1-(2-oxo-4-phenylbutyl)-3-phenyl-[1,2,4]triazolium tetrafluoroborate (QT-60). Synthesized using the procedure for the formation of 1,3,4,5-tetrasubstituted [1,2,4]triazolium salts above to give a white solid in 40% yield from 4-phenyl-1-(3-phenyl-[1,2,4]triazol-1-yl)-butan-2-one and trimethyloxonium tetrafluoroborate: mp ~50° C.; $R_f$=0.05 ($CHCl_3$); $^1H$ NMR (400 MHz, $CD_3OD$): δ 2.92-3.05 (m, 4H), 4.01 (s, 3H), 5.53 (s, 2H), 7.15-7.20 (m, 1H), 7.21-7.30 (m, 4H), 7.60-7.73 (m, 3H), 7.78-7.84 (m, 2H); $^{13}C$ NMR (100 MHz, $CD_3OD$): δ 30.0, 35.3, 42.3, 60.8, 123.9, 127.3, 129.4, 129.6, 130.5 (3C), 133.5, 141.8, 156.1, 201.2; $^1H$-$^1H$ NOESY: no observable NOE between protons at 4.01 ppm and the protons at 5.53 ppm which confirms methylation in the 4-position; HRMS (ESI): Calcd. for $C_{19}H_{20}N_3O$ ([M−$BF_4$]$^+$): 306.1606. Found: 306.1603.

2.12. Representative Procedure for the Formation of Bis-Imidazole Compounds, as Outlined in Scheme 4

2.12.1. 1,4-Bis-(1H-imidazol-1-yl)butane dihydrochloride (QT-126). Under a $N_2$ atmosphere, a mixture of imidazole (1.70 g, 25 mmol, 2 equiv) and sodium hydroxide (1.00 g, 25 mmol, 2 equiv) in dimethyl sulfoxide (5 mL) was stirred at 60° C. for 1.5 h. To this mixture was added carefully (very exothermic) 1,4-dibromobutane (2.70 g, 12.5 mmol, 1 equiv) and the mixture stirred at 60° C. for 2.5 h. The temperature was increased to ~100° C. and a stream of $N_2$ gas was blown over the mixture to remove dimethyl sulfoxide; the mixture solidified after 2 h. The mushy solid was dried under high vacuum leaving a beige solid which was extracted into benzene (3×75 mL) with excessive stirring and without the addition of water. The combined organic extracts were dried ($MgSO_4$), filtered, and the filtrate concentrated to a clear oil. {Alternatively, in cases where the alkane was longer than dodecane, the free base was isolated simply by cooling the DMSO-containing reaction mixture to 0° C., diluting with water, collecting the solid precipitate by filtration, and washing the solid free base with water.} High-vacuum drying gave the crude free base as a white solid (1.22 g, 6.41 mmol, 51%). To a solution of the free base in warm 2-propanol (2 mL) was added a solution of 37% aqueous HCl (1.46 g, 14.8 mmol, 2.3 equiv) in 2-propanol (2 mL). The mixture was concentrated and dried under high vacuum. The residue was recrystallized from a mixture of methanol/ethanol/2-propanol. High-vacuum drying left QT-126 (881 mg, 3.35 mmol, 27%) as a white solid in the dihydrochloride form: mp>260° C.; $R_f$=0.9 (MeOH); $^1H$ NMR (400 MHz, $CD_3OD$): δ 1.94-2.02 (m, 4H), 4.33-4.41 (m, 4H), 7.60 (s, 2H), 7.73 (s, 2H), 9.07 (s, 2H); $^{13}C$ NMR (100 MHz, $CD_3OD$): δ 28.0, 49.8, 121.2, 123.3, 136.5; HRMS (ESI): Calcd. for $C_{10}H_{15}N_4$ ([M−H−2Cl]$^+$) 191.1297. Found: 191.1288.

2.13. Characterization of Bis-Imidazole Compounds Synthesized Following the Representative Procedure (as Shown for QT-126)

2.13.1. 1,6-Bis-(1H-imidazol-1-yl)hexane dihydrochloride (QT-127). White solid in 24% yield from 1,6-dibromohexane: mp 220-221° C.; $R_f$=0 (EtOAc); $^1H$ NMR (400 MHz, $CD_3OD$): δ 1.38-1.49 (m, 4H), 1.88-2.00 (m, 4H), 4.30 (t, J=7.2 Hz, 4H), 7.59 (s, 2H), 7.71 (s, 2H), 9.04 (s, 2H); $^{13}C$ NMR (100 MHz, $CD_3OD$): δ 26.6, 30.9, 50.4, 121.1, 123.4, 136.3; HRMS (ESI): Calcd. for $C_{12}H_{19}N_4$ ([M−H−2Cl]$^+$) 219.1610. Found: 219.1599.

2.13.2. 1,8-Bis-(1H-imidazol-1-yl)octane dihydrochloride (QT-128). White solid (recrystallized instead from EtOH/2-propanol) in 77% yield from 1,8-dibromooctane: mp 176-177 C; $R_f$=0 (EtOAc); $^1H$ NMR (400 MHz, $CD_3OD$): δ 1.30-1.46 (m, 8H), 1.84-1.98 (m, 4H), 4.28 (t, J=7.4 Hz, 4H), 7.59 (app t, J=1.6 Hz, 2H), 7.69 (app t, J=1.8 Hz, 2H), 9.02 (s, 2H); $^{13}C$ NMR (100 MHz, $CD_3OD$): δ 27.1, 29.8, 31.1, 50.6, 121.1, 123.3, 136.3; HRMS (ESI): Calcd. for $C_{14}H_{23}N_4$ ([M−H−2Cl]$^+$) 247.1923. Found: 247.1918.

2.13.3. 1,10-Bis-(1H-imidazol-1-yl)decane dihydrochloride (QT-129). White solid (recrystallized instead from EtOH/2-propanol) in 84% yield from 1,10-dibromodecane: mp 143-144 C; $R_f$=0 (EtOAc); $^1H$ NMR (400 MHz, $CD_3OD$): δ 1.28-1.42 (m, 12H), 1.85-1.96 (m, 4H), 4.27 (t, J=7.4 Hz, 4H), 7.59 (app t, J=1.6 Hz, 2H), 7.69 (app t, J=1.6 Hz, 2H), 9.02 (s, 2H); $^{13}C$ NMR (100 MHz, $CD_3OD$): δ 27.3, 30.0, 30.4, 31.2, 50.6, 121.1, 123.3, 136.3; HRMS (ESI): Calcd. for $C_{16}H_{27}N_4$ ([M−H−2Cl]$^+$) 275.2236. Found: 275.2229.

2.13.4. 1,11-Bis-(1H-imidazol-1-yl)undecane (QT-117). Golden oil (the solid free base was isolated and turned into an oil upon high-vacuum drying) in 96% yield from 1,11-dibromoundecane: $^1H$ NMR (400 MHz, $CDCl_3$): δ 1.15-1.34 (m, 14H), 1.68-1.80 (m, 4H), 3.90 (t, J=7.2 Hz, 4H), 6.88 (s, 2H), 7.03 (s, 2H), 7.43 (s, 2H); $^{13}C$ NMR (100 MHz, $CD_3OD$): δ

26.6, 29.1, 29.4 (2C), 31.1, 47.1, 118.9, 129.4, 137.1; HRMS (ESI): Calcd. for $C_{17}H_{28}N_4$ ($M^+$) 288.2314. Found: 288.2321.

2.13.5. 1,12-Bis-(1H-imidazol-1-yl)dodecane dihydrochloride (QT-130). White solid (recrystallized instead from 2-propanol/$Et_2O$) in 89% yield from 1,12-dibromododecane: mp 164-165 C; $R_f$=0 (EtOAc); $^1H$ NMR (400 MHz, $CD_3OD$): δ 1.27-1.42 (m, 16H), 1.86-1.96 (m, 4H), 4.27 (t, J=7.4 Hz, 4H), 7.58 (app t, J=1.6 Hz, 2H), 7.69 (app t, J=1.6 Hz, 2H), 9.01 (s, 2H); $^{13}C$ NMR (100 MHz, $CD_3OD$): δ 27.3, 30.1, 30.5, 30.6, 31.2, 50.6, 121.1, 123.3, 136.3; HRMS (ESI): Calcd. for $C_{18}H_{31}N_4$ ($[M-H-2Cl]^+$) 303.2549. Found: 303.2535.

2.13.6. 1,13-Bis-(1H-imidazol-1-yl)tridecane dihydrochloride (QT-108). Orange oil (did not crystallize) in 88% yield from 1,13-diiodotridecane: $^1H$ NMR (400 MHz, $CD_3OD$): δ 1.25-1.42 (m, 18H), 1.85-1.95 (m, 4H), 4.27 (t, J=7.4 Hz, 4H), 7.59 (s, 2H), 7.69 (s, 2H), 9.02 (s, 2H); $^{13}C$ NMR (100 MHz, $CD_3OD$): δ 27.3, 30.1, 30.5, 30.6, 30.7, 31.2, 50.6, 121.1, 123.3, 136.3; HRMS (ESI): Calcd. for $C_{19}H_{33}N_4$ ($[M-H-2Cl]^+$) 317.2699. Found: 317.2696.

2.13.7. 1,14-Bis-(1H-imidazol-1-yl)tetradecane dihydrochloride (QT-106). White solid (not recrystallized) in 99% yield from 1,14-diiodotetradecane: mp 142-143° C.; $^1H$ NMR (400 MHz, $CD_3OD$): δ 1.20-1.44 (m, 20H), 1.85-1.98 (m, 4H), 4.26 (t, J=7.4 Hz, 4H), 7.58 (s, 2H), 7.68 (s, 2H), 8.99 (s, 2H); $^{13}C$ NMR (100 MHz, $CD_3OD$): δ 27.4, 30.1, 30.6, 30.7, 30.8, 31.3, 50.7, 121.2, 123.4, 136.4; HRMS (ESI): Calcd. for $C_{20}H_{36}N_4$ ($[M-2Cl]^{2+}/2$) 166.1464. Found: 166.1463.

2.13.8. 1,15-Bis-(1H-imidazol-1-yl)pentadecane dihydrochloride (QT-100). Yellow solid in 100% yield from 1,15-diiodopentadecane: mp 98-99° C.; $^1H$ NMR (400 MHz, $CD_3OD$): δ 1.24-1.43 (m, 22H), 1.85-1.98 (m, 4H), 4.20-4.35 (m, 4H), 7.57 (s, 2H), 7.67 (s, 2H), 8.98 (s, 2H); $^{13}C$ NMR (100 MHz, $CD_3OD$): δ 18.3, 27.4, 30.2, 30.6, 30.7, 30.8, 31.3, 50.9, 121.2, 123.5, 136.6; HRMS (ESI): Calcd. for $C_{21}H_{38}N_4$ ($[M-2Cl]^{2+}/2$) 173.1542. Found: 173.1544.

2.13.9. 1,20-Bis-(1H-imidazol-1-yl)eicosane (QT-115). Off-white solid (isolated as the free base) in 68% yield from 1,20-dibromoeicosane: mp 58-59° C.; $^1H$ NMR (400 MHz, $CDCl_3$): δ 1.18-1.36 (m, 32H), 1.70-1.80 (m, 4H), 3.91 (t, J=7.0 Hz, 4H), 6.89 (s, 2H), 7.04 (s, 2H), 7.45 (s, 2H); $^{13}C$ NMR (100 MHz, $CDCl_3$): δ 26.7, 29.2, 29.55, 29.64, 29.7, 29.77, 29.81 (2C), 31.2, 47.2, 118.9, 129.5, 137.2; HRMS (EI): Calcd. for $C_{26}H_{46}N_4$ ($M^+$) 414.3722. Found: 414.3748.

2.14. Representative Procedure for the Formation of Bis-Imidazolium Compounds, as Outlined in Scheme 4

2.14.1. 1,4-Bis-(3-methylimidazolium-1-yl)butane diiodide (QT-86). The dihydrochloride salt QT-126 (400 mg, 1.52 mmol) was dissolved in water (2 mL) and the solution basified with excess $Na_2CO_3$ (400 mg, 3.77 mmol). The mixture was extracted with EtOAc (3×), and the combined organic extracts were dried ($Na_2SO_4$), concentrated, and dried under high vacuum leaving the free base (167 mg, 0.88 mmol, 58%). The free base (167 mg, 0.88 mmol, 1 equiv) was dissolved in 1-propanol (2 mL) at it and to this was added iodomethane (0.22 mL, 3.52 mmol, 4 equiv). The mixture was stirred at reflux temperature for 24 h, then cooled to 0° C. The resulting oil was washed with $Et_2O$ (3×10 mL, decanted off the $Et_2O$ layer each time), then concentrated at 60° C. and dried under high vacuum leaving a beige solid (395 mg, 0.83 mmol, 94%). The solid was recrystallized from boiling 2-propanol (4 mL), and washed with $Et_2O$. High-vacuum drying left QT-86 (383 mg, 0.81 mmol, 92%) as a white solid in the diiodide form: mp 103-104 C; $^1H$ NMR (400 MHz, DMSO-$d_6$): δ 1.70-1.86 (m, 4H), 3.85 (s, 6H), 4.15-4.26 (m, 4H), 7.71 (s, 2H), 7.76 (s, 2H), 9.11 (s, 2H); $^{13}C$ NMR (100 MHz, DMSO-$d_6$): δ 26.1, 36.0, 48.1, 122.3, 123.7, 136.6; HRMS (ESI): Calcd. for $C_{12}H_{20}N_4$ ($[M-2I]^{2+}/2$) 110.0838. Found: 110.0840.

2.15. Characterization of the Bis-Imidazolium Compounds Synthesized Following the Representative Procedure (as Shown for QT-86) Unless Otherwise Stated 2.15.1. 1,6-Bis-(3-methylimidazolium-1-yl)hexane diiodide (QT-87). White solid (recrystallized instead from 2-propanol/EtOH) in 95% yield from the free base form of QT-127: mp 156-157 C; $^1H$ NMR (400 MHz, DMSO-$d_6$): δ 1.20-1.32 (m, 4H), 1.71-1.83 (m, 4H), 3.85 (s, 6H), 4.16 (t, J=7.0 Hz, 4H), 7.70 (s, 2H), 7.77 (s, 2H), 9.12 (s, 2H); $^{13}C$ NMR (100 MHz, DMSO-$d_6$): δ 24.9, 29.2, 35.9, 48.7, 122.3, 123.6, 136.5; HRMS (ESI): Calcd. for $C_{14}H_{24}N_4$ ($[M-2I]^{2+}/2$) 124.0994. Found: 124.0998.

2.15.2. 1,8-Bis-(3-methylimidazolium-1-yl)octane diiodide (QT-71). White-orange solid (recrystallized instead from 2-propanol/$Et_2O$) in 88% yield from the free base form of QT-128: mp 115-116 C; $^1H$ NMR (400 MHz, DMSO-$d_6$): δ 1.16-1.32 (m, 8H), 1.71-1.82 (m, 4H), 3.85 (s, 6H), 4.15 (t, J=7.2 Hz, 4H), 7.70 (s, 2H), 7.76 (s, 2H), 9.11 (s, 2H); $^{13}C$ NMR (100 MHz, DMSO-$d_6$): δ 25.4, 28.2, 29.4, 35.9, 48.8, 122.3, 123.6, 136.4; HRMS (ESI): Calcd. for $C_{16}H_{28}W$ ($[M-I]^+$) 403.1358. Found: 403.1368.

2.15.3. 1,10-Bis-(3-methylimidazolium-1-yl)decane diiodide (QT-88). Brown oil in 76% yield from the free base form of QT-129: $^1H$ NMR (400 MHz, DMSO-$d_6$): δ 1.16-1.32 (m, 12H), 1.71-1.81 (m, 4H), 3.85 (s, 6H), 4.14 (t, J=7.2 Hz, 4H), 7.69 (s, 2H), 7.76 (s, 2H), 9.10 (s, 2H); $^{13}C$ NMR (100 MHz, DMSO-$d_6$): δ 25.5, 28.4, 28.7, 29.4, 35.8, 48.8, 122.3, 123.6, 136.4; HRMS (ESI): Calcd. for $C_{18}H_{32}N_4I$ ($[M-I]^+$) 431.1671. Found: 431.1658.

2.15.4. 1,11-Bis-(3-methylimidazolium-1-yl)undecane diiodide (QT-118). Brown oil in 96% yield from the free base QT-117: $^1H$ NMR (400 MHz, DMSO-$d_6$): δ 1.12-1.34 (m, 14H), 1.68-1.84 (m, 4H), 3.85 (s, 6H), 4.15 (t, J=7.2 Hz, 4H), 7.71 (s, 2H), 7.78 (s, 2H), 9.13 (s, 2H); $^{13}C$ NMR (100 MHz, DMSO-$d_6$): δ 25.5, 28.4, 28.8, 28.9, 29.4, 35.8, 48.7, 122.2, 123.6, 136.4; HRMS (ESI): Calcd. for $C_{19}H_{34}N_4$ ($[M-2I]^{2+}/2$) 159.1386. Found: 159.1380.

2.15.5. 1,12-Bis-(3-methylimidazolium-1-yl)dodecane diiodide (QT-89). Brown oil in 97% yield from the free base form of QT-130: $^1H$ NMR (400 MHz, DMSO-$d_6$): δ 1.15-1.32 (m, 16H), 1.70-1.82 (m, 4H), 3.85 (s, 6H), 4.14 (t, J=7.2 Hz, 4H), 7.69 (s, 2H), 7.76 (s, 2H), 9.11 (s, 2H); $^{13}C$ NMR (100 MHz, DMSO-$d_6$): δ 25.5, 28.4, 28.8, 28.9, 29.4, 35.8, 48.8, 122.3, 123.6, 136.4; HRMS (ESI): Calcd. for $C_{20}H_{36}N_4I$ ($[M-I]^+$) 459.1984. Found: 459.1977.

2.15.6. 1,12-Bis-(3-ethylimidazolium-1-yl)dodecane diiodide (QT-99). Under a $N_2$ atmosphere, the free base form of QT-130 (205 mg, 0.68 mmol, 1 equiv) was dissolved in 1-propanol (2 mL) at it and to this was added iodoethane (0.49 mL, 955 mg, 6.12 mmol, 9 equiv). The mixture was stirred at reflux temperature (~110° C.) for 24 h, another portion of iodoethane (0.25 mL) was added, and the mixture stirred at ~110° C. for 3 h. The mixture was cooled to 0° C., and $Et_2O$ was added. The resulting insoluble oil was washed with $Et_2O$ (3×10 mL, $Et_2O$ layer removed using a pipette each time), then dried under high vacuum leaving an amber oil (323 mg, 0.53 mmol, 78%). The oil ($R_f$=0, EtOAc) was purified using preparatory-scale thin layer chromatography: the plate was loaded using MeOH, dry, eluted twice using 95:5 EtOAc-MeOH, eluted twice using 90:10 EtOAc-MeOH, bottom of the plate was cut out and extracted using MeOH, the extract was filtered, and the filtrate concentrated. High-vacuum drying left QT-99 (189 mg, 0.31 mmol, 46%) as an amber oil in the diiodide form: $^1$H NMR (400 MHz, DMSO-d$_6$): δ 1.12-1.35 (m, 16H), 1.42 (t, J=7.2 Hz, 6H), 1.73-1.87 (m, 4H), 4.10-4.28 (m, 8H), 7.79 (s, 2H), 7.81 (s, 2H), 9.21 (s, 2H); $^{13}$C NMR (100 MHz, DMSO-d$_6$): δ 15.0, 25.5, 28.4, 28.8, 28.9, 29.3, 44.2, 48.8, 122.1, 122.4, 135.6; HRMS (ESI): Calcd. for C$_{22}$H$_{40}$N$_4$ ([M−2I]$^{2+}$/2) 180.1627. Found: 180.1623.

2.15.7. 1,12-Bis-(3-propylimidazolium-1-yl)dodecane diiodide (QT-119). Under a N$_2$ atmosphere, the free base form of QT-130 (302 mg, 1.00 mmol, 1 equiv) was dissolved in 1-propanol (8 mL) at it and to this was added 1-iodopropane (1.02 g, 6.00 mmol, 6 equiv). The mixture was stirred at reflux temperature for 24 h, another portion of 1-iodopropane (1.02 g, 6.00 mmol, 6 equiv) was added, and the mixture stirred at reflux temperature for 24 h. A final portion of 1-iodopropane (1.02 g, 6.00 mmol, 6 equiv) was added, and the mixture stirred at reflux temperature for a further 42 h. The mixture was concentrated to a brown oil. The oil was purified using flash column chromatography on silica gel (elute with EtOAc-MeOH 9:1 v/v first, then an increasing gradient of methanol was applied). High-vacuum drying left QT-119 (275 mg, 43%) as a brown solid: mp 121-123° C.; $^1$H NMR (400 MHz, DMSO-d$_6$): δ 0.84 (t, J=7.4 Hz, 6H), 1.23 (br s, 18H), 1.73-1.86 (m, 8H), 4.10-4.18 (m, 8H), 7.79 (s, 2H), 7.80 (s, 2H), 9.18 (s, 2H); $^{13}$C NMR (100 MHz, DMSO-d$_6$): δ 10.4, 22.7, 25.5, 28.3, 28.8, 28.9, 29.3, 48.9, 50.3, 122.4, 135.9; HRMS (ESI): Calcd. for C$_{24}$H$_{44}$N$_4$ ([M−2I]$^{2+}$/2) 194.1777. Found 194.1774.

2.15.8. 1,13-Bis-(3-methylimidazolium-1-yl)tridecane diiodide (QT-109). Brown oil in 96% yield from 1,13-bis-(1H-imidazol-1-yl)tridecane (the free base form of QT-108): $^1$H NMR (400 MHz, DMSO-d$_6$): δ 1.16-1.32 (m, 18H), 1.71-1.82 (m, 4H), 3.85 (s, 6H), 4.15 (t, J=7.2 Hz, 4H), 7.71 (s, 2H), 7.77 (s, 2H), 9.12 (s, 2H); $^{13}$C NMR (100 MHz, DMSO-d$_6$): δ 25.5, 28.4, 28.9, 29.0 (2C), 29.4, 35.8, 48.8, 122.2, 123.6, 136.4; HRMS (ESI): Calcd. for C$_{21}$H$_{38}$N$_4$ ([M−2I]$^{2+}$/2) 173.1542. Found: 173.1544.

2.15.9. 1,14-Bis-(3-methylimidazolium-1-yl)tetradecane diiodide (QT-107). Amber oil in 96% yield from 1,14-bis-(1H-imidazol-1-yl)tetradecane (the free base form of QT-106): $^1$H NMR (400 MHz, DMSO-d$_6$): δ 1.15-1.35 (m, 20H), 1.70-1.85 (m, 4H), 3.85 (s, 6H), 4.10-4.20 (m, 4H), 7.71 (s, 2H), 7.77 (s, 2H), 9.12 (s, 2H); $^{13}$C NMR (100 MHz, DMSO-d$_6$): δ 25.5, 28.4, 28.9, 29.0, 29.1, 29.4, 35.8, 48.8, 122.3, 123.6, 136.5; HRMS (ESI): Calcd. for C$_{22}$H$_{40}$N$_4$ ([M−2I]$^{2+}$/2) 180.1621. Found: 180.1622.

2.15.10. 1,15-Bis-(3-methylimidazolium-1-yl)pentadecane diiodide (QT-101). Amber oil in 80% yield from 1,15-bis-(1H-imidazol-1-yl)pentadecane (the free base form of QT-100): $^1$H NMR (400 MHz, DMSO-d$_6$): δ 1.15-1.35 (m, 22H), 1.70-1.85 (m, 4H), 3.85 (s, 6H), 4.15 (t, J=7.2 Hz, 4H), 7.70 (s, 2H), 7.77 (s, 2H), 9.11 (s, 2H); $^{13}$C NMR (100 MHz, DMSO-d$_6$): δ 25.4, 28.3, 28.8, 28.9, 29.0, 29.3, 35.7, 48.7, 122.2, 123.5, 136.4; HRMS (ESI): Calcd. for C$_{23}$H$_{41}$N$_4$ ([M−2I−H]$^{2+}$/2) 373.3325. Found: 373.3326.

2.15.11. 1,20-Bis-(3-methylimidazolium-1-yl)eicosane diiodide (QT-116). Yellow solid in 70% yield from the free base QT-115: mp 78-80 C; $^1$H NMR (400 MHz, DMSO-d$_6$): δ 1.18-1.30 (m, 32H), 1.72-1.82 (m, 4H), 3.85 (s, 6H), 4.15 (t, J=7.2 Hz, 4H), 7.70 (s, 2H), 7.77 (s, 2H), 9.11 (s, 2H); $^{13}$C NMR (100 MHz, DMSO-d$_6$): δ 25.5, 28.8, 28.9, 29.1 (4C), 29.3, 35.8, 48.7, 122.2, 123.6, 136.4; HRMS (ESI): Calcd. for C$_{28}$H$_{52}$N$_4$ ([M−2I]$^{2+}$/2) 222.2090. Found: 222.2089.

2.16. Various Synthetic Procedures 2.16.1. 4,4'-Bis-(1H-imidazol-1-yl)biphenyl (QT-96). Under a N$_2$ atmosphere, a mixture of 4,4'-dibromobiphenyl (5.00 g, 16.03 mmol, 1 equiv), imidazole (4.58 g, 67.33 mmol, 4.2 equiv), K$_2$CO$_3$ (6.98 g, 50.50 mmol, 3.2 equiv), and CuSO$_4$ (51.08 mg, 0.32 mmol, 0.02 equiv) was stirred at ~180° C. for 24 h. The mixture was cooled to rt, water (200 mL) was added, and the solid collected by filtration. The solid was dissolved in warm EtOH (200 mL), the solution filtered, and the filtrate concentrated and dried under high vacuum. The resulting off-white solid was purified using flash column chromatography on silica gel (silica plug made using MeOH, wash with EtOAc, elute with MeOH) to give QT-96 (0.87 g, 3.04 mmol, 19%) as an off-white solid: mp 288-289° C.; $^1$H NMR (400 MHz, DMSO-d$_6$): δ 7.14 (s, 2H), 7.78 (d, J=8.4 Hz, 4H), 7.83 (s, 2H), 7.88 (d, J=8.8 Hz, 4H), 8.35 (s, 2H); $^{13}$C NMR (100 MHz, DMSO-d$_6$): δ 117.9, 120.7, 128.0, 130.0, 135.5, 136.3, 137.3; HRMS (EI): Calcd. for C$_{18}$H$_{14}$N$_4$ (M$^+$) 286.1218. Found: 286.1219.

2.16.2. 4,4'-Bis-(3-methyl-1H-imidazolium-1-yl)biphenyl diiodide (QT-98). Under a N$_2$ atmosphere, a mixture of 4,4'-bis-(1H-imidazol-1-yl)biphenyl (QT-96) (200 mg, 0.70 mmol, 1 equiv), n-propanol (3 mL), and iodomethane (0.44 mL, 994 mg, 7.00 mmol, 10 equiv) was stirred at ~85° C. for 6 h. The solution was stirred at it for 24 h, then diluted with Et$_2$O. The solid was collected by filtration and washed with Et$_2$O. High-vacuum drying left QT-98 (365 mg, 0.64 mmol, 91%) as a yellow solid: mp>300° C.; $^1$H NMR (400 MHz, DMSO-d$_6$): δ 3.98 (s, 6H), 7.93 (d, J=8.4 Hz, 4H), 8.00 (s, 2H), 8.11 (d, J=8.0 Hz, 4H), 8.39 (s, 2H), 9.87 (s, 2H); $^{13}$C NMR (100 MHz, DMSO-d$_6$): δ 36.3, 120.9, 122.3, 124.5, 128.5, 134.5, 136.0, 139.4; HRMS (ESI): Calcd. for C$_{20}$H$_{20}$N$_4$ ([M−2I]$^{2+}$/2) 158.0838. Found: 158.0857.

2.16.3. 4,4'-Bis-(3-benzyl-1H-imidazolium-1-yl)biphenyl dibromide (QT-102). Under a N$_2$ atmosphere, 4,4'-bis-(1H-imidazol-1-yl)biphenyl (QT-96) (200 mg, 0.70 mmol, 1 equiv) was combined with n-propanol (3 mL) and to this was added benzyl bromide (0.33 mL, 479 mg, 2.80 mmol, 4 equiv). The mixture was stirred at ~85° C. for 24 h, and then slowly cooled to 0° C., resulting in a white solid precipitate. The solid was collected by filtration and washed with cold n-propanol and then with Et$_2$O. The white solid obtained was recrystallized from hot MeOH. High-vacuum drying left QT-102 (176 mg, 0.28 mmol, 40%) as a white solid: mp 308-309° C.; $^1$H NMR (400 MHz, DMSO-d$_6$): δ 5.56 (s, 4H), 7.41-7.50 (m, 6H), 7.98 (d, J=8.4 Hz, 4H), 7.98 (d, J=8.4 Hz, 4H), 8.11 (d, J=8.8 Hz, 6H), 8.45 (s, 2H), 10.21 (s, 2H); $^{13}$C NMR (100 MHz, DMSO-d$_6$): δ 52.4, 121.6, 122.4, 123.3, 128.4, 128.6, 128.9, 129.0, 134.5, 134.5, 135.6, 139.4; HRMS (ESI): Calcd. for C$_{32}$H$_{28}$N$_4$ ([M−2Br]$^{2+}$/2) 234.1151. Found: 234.1148.

2.16.4. 4,4'-Bis-[3-(4-nitrobenzyl)-1H-imidazolium-1-yl] biphenyl dibromide (QT-103). Under a N$_2$ atmosphere, 4,4'-bis-(1H-imidazol-1-yl)biphenyl (QT-96) (200 mg, 0.70 mmol, 1 equiv) was combined with n-propanol (6 mL) and to this was added 4-nitrobenzyl bromide (907 mg, 4.20 mmol, 6 equiv). The mixture was stirred at ~110° C. for 72 h, and then slowly cooled to 0° C., resulting in a solid precipitate. The solid was collected by filtration and washed with cold n-propanol and then with Et$_2$O. The yellow solid obtained was recrystallized from hot MeOH (20 mL). High-vacuum drying left QT-103 (127 mg, 0.18 mmol, 26%) as a yellow solid: mp 302-303° C.; $^1$H NMR (400 MHz, DMSO-d$_6$): δ 5.74 (s, 4H), 7.83 (d, J=8.4 Hz, 4H), 7.98 (d, J=8.4 Hz, 4H), 8.12 (d, J=7.2 Hz, 6H), 8.31 (d, J=8.4 Hz, 4H), 8.49 (s, 2H), 10.20 (s, 2H); $^{13}$C NMR (100 MHz, DMSO-d$_6$): δ 51.5, 121.7, 122.4, 123.4, 124.0, 128.4, 129.8, 134.5, 136.2, 139.5, 141.6, 147.7; HRMS (ESI): Calcd. for C$_{32}$H$_{26}$N$_6$O$_4$ ([M−2Br]$^{2+}$/2) 279.1002. Found: 279.1002.

2.16.5. 1,3-Dimethyl-4,5-diphenyl-1H-imidazolium iodide (QT-104). Under a N$_2$ atmosphere, 4,5-diphenylimidazole (200 mg, 0.91 mmol, 1 equiv) was dissolved in toluene (3 mL) over a 30-min period at rt. To this solution was added iodomethane (0.57 mL, 1.29 g, 9.1 mmol, 10 equiv). The mixture was stirred at rt for 15 min, then at ~80° C. Three other portions of iodomethane (0.57 mL, 1.29 g, 9.1 mmol, 10 equiv) were added after 24 h, 48 h, and 120 h at 80° C. After a total reaction time of 6 days at 80° C. the mixture was cooled to rt, and then concentrated. The red oil obtained was recrystallized from MeOH (2 mL) with a few drops of Et$_2$O. The solid was collected by filtration and washed with Et$_2$O (10 mL). High-vacuum drying left QT-104 (146 mg, 0.39 mmol, 43%) as yellow solid: mp 190-191° C.; $^1$H NMR (400 MHz, DMSO-d$_6$): δ 7.39-7.43 (m, 4H), 7.45-7.50 (m, 6H), 9.38 (s, 1H); $^{13}$C NMR (100 MHz, DMSO-d$_6$): δ 34.4, 125.1, 129.0, 130.1, 130.6, 131.5, 136.8; HRMS (ESI): Calcd. for C$_{17}$H$_{17}$N$_2$ ([M−I]$^+$) 249.1391. Found: 249.1383.

2.16.6. 1,3-dibenzyl-4,5-diphenyl-1H-imidazolium bromide (QT-105). Under a N$_2$ atmosphere, 4,5-diphenylimidazole (200 mg, 0.91 mmol, 1 equiv) was dissolved in toluene (2 mL) over a 30-min period at rt. To this solution was added benzyl bromide (1.30 mL, 1.87 g, 10.92 mmol, 12 equiv) and the mixture stirred at 120° C. Two more portions of benzyl bromide (1.30 mL, 1.87 g, 10.92 mmol, 12 equiv) were added after 120 h and 192 h at ~120° C. After a total reaction time of 9 days at ~120° C., the mixture was cooled on ice and diluted with Et$_2$O (100 mL). The resulting white solid precipitate was collected by filtration, washed with Et$_2$O (100 mL), and then purified using flash column chromatography on silica gel (silica plug made using MeOH, wash with EtOAc, elute with MeOH). High-vacuum drying left QT-105 (223 mg, 0.46 mmol, 51%) as a white solid: mp 209-210° C.; $^1$H NMR (400 MHz, DMSO-d$_6$): δ 5.45 (s, 4H), 7.00-7.15 (m, 4H), 7.20-7.45 (m, 16H), 9.73 (s, 1H); $^{13}$C NMR (100 MHz, DMSO-d$_6$): δ 50.5, 125.0, 127.8, 128.5, 128.8, 130.1, 130.8, 131.8, 134.0, 136.6; HRMS (ESI): Calcd. for C$_{29}$H$_{25}$N$_2$ ([M−Br]$^+$) 401.2017. Found: 401.2010.

2.16.7. 4,4'-Bis-(3-methylbenzimidazolium-1-yl)biphenyl diiodide (QT-110). Under a N$_2$ atmosphere, a mixture of 4,4'-dibromobiphenyl (1.00 g, 3.20 mmol, 1 equiv), benzimidazole (1.89 g, 16.00 mmol, 5 equiv), K$_2$CO$_3$ (1.37 g, 9.92 mmol, 3.1 equiv), and CuSO$_4$ (16 mg, 0.10 mmol, 0.03 equiv) was stirred at ~180° C. for 24 h. The mixture was cooled to rt, water (200 mL) was added, and the solid collected by filtration. The solid was dissolved in hot MeOH (200 mL), the solution filtered, and the filtrate concentrated and dried under high vacuum. The resulting grey solid was washed with hot water (3×50 mL) and then recrystallized from hot EtOAc (30 mL). High-vacuum drying left 4,4'-bis-(1H-benzimidazol-1-yl)biphenyl (91 mg, 0.24 mmol, 8%) as a brown solid: mp 258-259° C.; $^1$H NMR (100 MHz, DMSO-d$_6$): δ 7.30-7.42 (m, 4H), 7.72 (d, J=7.6 Hz, 2H), 7.81 (d, J=7.6 Hz, 2H), 7.85 (d, J=8.4 Hz, 4H), 8.04 (d, J=8.4 Hz, 4H), 8.66 (s, 2H); $^{13}$C NMR (400 MHz, DMSO-d$_6$): δ 110.8, 120.1, 122.6, 123.6, 124.2, 128.4, 135.6, 138.3; HRMS (ESI): Calcd. for C$_{26}$H$_{19}$N$_4$ ([M+H]$^+$) 387.1609. Found: 387.1607.

Under a N$_2$ atmosphere, a mixture of 4,4'-bis-(1H-benzimidazol-1-yl)biphenyl (59 mg, 0.15 mmol, 1 equiv), n-propanol (2 mL), and iodomethane (0.09 mL, 213 mg, 1.50 mmol, 10 equiv) was stirred at ~85° C. for 24 h and then stirred at it for 24 h. Et$_2$O (50 mL) was added, and the resulting solid precipitate was collected by filtration, washed with Et$_2$O, and dried under high vacuum to obtain a brown solid. The solid was recrystallized from hot MeOH (7 ml) with a few drops of Et$_2$O. High-vacuum drying left QT-110 (20 mg, 0.03 mmol, 20%) as orange solid: mp>300° C.; $^1$H NMR (400 MHz, DMSO-d$_6$): δ 4.21 (s, 6H), 7.70-8.05 (m, 10H), 8.15-8.25 (m, 6H), 10.19 (s, 2H); $^{13}$C NMR (100 MHz, DMSO-d$_6$): δ 33.6, 114.0, 125.8, 128.9, 130.9, 131.9, 133.1, 140.3, 143.2; HRMS (ESI): Calcd. for C$_{28}$H$_{24}$N$_4$ ([M−2I]$^{2+}$/2) 208.0994. Found: 208.0992.

2.16.8. 4,4'-Bis-(1H-imidazol-1-yl-methyl)biphenyl (QT-111). Under a N$_2$ atmosphere, a mixture of imidazole (569 mg, 8.36 mmol, 2.1 equiv) and sodium hydroxide (334 mg, 8.36 mmol, 2.1 equiv) in dimethyl sulfoxide (3 mL) was stirred at 70-80° C. for 1 h. The mixture was cooled to it and a solution of 4,4'-bis-(chloromethyl)biphenyl (1.00 g, 3.98 mmol, 1 equiv) in dimethyl sulfoxide (5 mL) was slowly added. The mixture was stirred at 70-80° C. for 24 h, then cooled to it and diluted with water (300 mL). The resulting white precipitate was collected by filtration, washed with water (100 mL), dissolved in MeOH (10 mL), and then concentrated. High-vacuum drying left QT-111 (981 mg, 3.12 mmol, 78%) as an off-white solid: mp 161-162° C.; $^1$H NMR (400 MHz, CDCl$_3$): δ 5.17 (s, 4H); 6.94 (s, 2H), 7.12 (s, 2H), 7.23 (d, J=8.0 Hz, 4H), 7.55 (d, J=7.6 Hz, 4H), 7.60 (s, 2H); $^{13}$C NMR (100 MHz, CDCl$_3$): δ 50.6, 119.4, 127.7, 127.9, 130.1, 135.7, 137.6, 140.5; HRMS (EI): Calcd. for C$_{20}$H$_{18}$N$_4$ (M$^+$): 314.1531. Found: 314.1519.

2.16.9. 1,4-Bis-(1H-imidazol-1-yl)benzene (QT-112). Under a N$_2$ atmosphere, a mixture of 1,4-dibromobenzene (2.50 g, 10.60 mmol, 1 equiv), imidazole (3.03 g, 44.52 mmol, 4.2 equiv), K$_2$CO$_3$ (4.69 g, 33.93 mmol, 3.2 equiv), and CuSO$_4$ (34 mg, 0.21 mmol, 0.02 equiv) were stirred at ~180° C. for 24 h. The mixture was cooled to rt, and diluted with water (100 mL). The resulting solid was collected by filtration and washed with water (100 mL). The brown solid obtained was dissolved in hot EtOH (200 mL), the solution filtered, and the filtrate concentrated. High-vacuum drying left QT-112 (1.87 g, 8.90 mmol, 84%) as an white solid: mp 208-209° C.; $^1$H NMR (400 MHz, CDCl$_3$): δ 7.23 (s, 2H), 7.30 (s, 2H), 7.52 (s, 4H), 7.87 (s, 2H); $^{13}$C NMR (100 MHz, CDCl$_3$): δ 118.3, 123.0, 131.1, 135.7, 136.6; HRMS (EI): Calcd. for C$_{12}$H$_{10}$N$_4$ (M$^+$) 210.0905. Found: 210.0900.

2.16.10. 4,4'-Bis-(3-methylimidazolium-1-yl-methyl)biphenyl diiodide (QT-113). Under a N$_2$ atmosphere, a mixture of 4,4'-bis-(1H-imidazol-1-yl-methyl)biphenyl (QT-111) (200 mg, 0.64 mmol, 1 equiv), n-propanol (3 mL), and iodomethane (0.40 mL, 908 mg, 6.40 mmol, 10 equiv) was stirred at ~85° C. for 24 h, then stirred at rt for 24 h. The resulting yellow precipitate was collected by filtration and washed with Et$_2$O (50 mL). High-vacuum drying left QT-113 (346 mg, 0.58 mmol, 91%) as yellow solid: mp 215-216° C.; $^1$H NMR (400 MHz, DMSO-d$_6$): δ 3.87 (s, 6H), 5.48 (s, 4H), 7.53 (d, J=8.0 Hz, 4H), 7.73 (d, J=6.8 Hz, 4H), 7.74 (s, 2H), 7.84 (s, 2H), 9.26 (s, 2H); $^{13}$C NMR (100 MHz, DMSO-d$_6$): δ 35.9, 51.5, 122.3, 124.0, 127.2, 129.0, 134.3, 136.7, 139.7; HRMS (ESI): Calcd. for C$_{22}$H$_{24}$N$_4$ ([M−2I]$^{2+}$/2) 172.0994. Found: 172.0992.

2.16.11. 1,4-Bis-(3-methylimidazolium-1-yl)benzene diiodide (QT-114). Under a N$_2$ atmosphere, a mixture of 1,4-bis-(1H-imidazol-1-yl)benzene (QT-112) (200 mg, 0.95 mmol, 1 equiv), n-propanol (3 mL), and iodomethane (0.57 mL, 1.30 g, 9.50 mmol, 10 equiv) was stirred at it for 1 h, then stirred at ~85° C. for 24 h. The mixture was cooled to it and diluted with Et$_2$O (30 mL). The resulting white precipitate was collected by filtration and washed with Et$_2$O (20 mL). High-vacuum drying left QT-114 (335 mg, 0.68 mmol, 72%) as a white solid: mp 324-325° C.; $^1$H NMR (400 MHz, DMSO-d$_6$): δ 3.98 (s, 6H), 8.01 (s, 2H), 8.11 (s, 4H), 8.40 (s, 2H), 9.91 (s, 2H); $^{13}$C NMR (100 MHz, DMSO-d$_6$): δ 36.4, 120.9, 123.4, 124.6, 135.2, 136.4; HRMS (ESI): Calcd. for C$_{14}$H$_{16}$N$_4$ ([M−2I]$^{2+}$/2) 120.0681. Found: 120.0680.

2.16.12. 1,12-Bis(1H-1,2,4-triazol-1-yl)dodecane dihydrochloride (QT-121). Under a N$_2$ atmosphere, a mixture of 1,2,4-triazole (1035 mg, 15.00 mmol, 2.5 equiv) and NaOH (600 mg, 15.00 mmol, 2.5 equiv) in DMSO (4 mL) was stirred at 70-80° C. for 1 h, then 1,12-dibromododecane (1.97 g, 6.00 mmol, 1 equiv) was added, and the mixture stirred at 70-80° C. overnight. The mixture was diluted with water (50 mL), and the solid that formed was collected by filtration and air-dried to give a mixture of isomeric bis-triazoles (1.50 g, 4.93 mmol, 82%). The solid was dissolved in ethanol (10 mL), and then 37% aqueous HCl (2 g, 20.30 mmol, 2.1 equiv) in ethanol (2 mL) was added. The precipitate that formed was collected by filtration and recrystallized from ethanol. High-vacuum drying left QT-121 (1.45 g, 64%) as a white solid: mp 192-193° C.; $^1$H NMR (400 MHz, DMSO-d$_6$): δ 1.21 (br s, 16H), 1.72-1.83 (m, 4H), 4.20 (t, J=7.0 Hz, 4H), 8.24 (s, 2H), 8.91 (s, 2H); $^{13}$C NMR (100 MHz, DMSO-d$_6$): δ 25.6, 28.3, 28.8, 28.9, 49.6, 142.8, 148.0; HRMS (ESI): Calcd. for C$_{16}$H$_{30}$N$_6$ ([M−2Cl]$^{2+}$/2) 153.1261. Found 153.1265.

2.16.13. 1,4-Bis[3-(1H-imidazol-1-yl)propoxy]benzene dihydrochloride (QT-122). Under a N$_2$ atmosphere, a mixture of hydroquinone (2.75 g, 25 mmol, 1 equiv), 1,3-dibromopropane (20.2 g, 100 mmol, 2 equiv), and anhydrous K$_2$CO$_3$ (10.35 g, 75 mmol, 6 equiv) in acetone (75 mL) was stirred at reflux temperature for 24 h. The solid was removed by filtration and discarded, and the filtrate was concentrated. The semi-solid residue was diluted with hexanes (125 mL), and the resulting solid was removed by filtration and discarded. The filtrate was set aside overnight, and the crystals that formed were collected by filtration (2.05 g). The filtrate was concentrated to a yellow oil that was diluted with 2-propanol (10 mL) and refrigerated overnight to afford a second crop (1.28 g) of crystals. The combined crystalline material was recrystallized from ethanol (10 mL). High-vacuum drying left 1,4-bis(3-bromopropyloxy)benzene (2.88 g, 65%) as a yellowish solid: mp 72-73° C.; $^1$H NMR (400 MHz, CDCl$_3$): δ 2.25-2.34 (m, 4H), 3.60 (t, J=6.6 Hz, 4H), 4.06 (t, J=5.8 Hz, 4H), 6.84 (s, 4H); $^{13}$C NMR (100 MHz, CDCl$_3$): δ 30.2, 32.6, 66.2, 115.7, 153.2; HRMS (EI): Calcd. for C$_{12}$H$_{16}$Br$_2$O$_2$ (M$^+$) 349.9512. Found 349.9521.

Under a N$_2$ atmosphere, a mixture of imidazole (1224 mg, 18 mmol, 6 equiv) and NaOH (720 mg, 18 mmol, 6 equiv) in DMSO (8 mL) was stirred at 70-80° C. for 1 h, then 1,4-bis (3-bromopropyloxy)benzene (1056 mg, 3 mmol, 1 equiv) was added, and the mixture stirred at 70-80° C. overnight. The mixture was partitioned between water (120 mL) and ethyl acetate (30 mL), the organic phase separated, and the aqueous phase was further extracted with ethyl acetate (2×20 mL). The combined organic extracts were washed with water (50 mL) and then with brine (20 mL), dried over anhydrous Na$_2$SO$_4$, and concentrated to a brown solid (784 mg, 80%). A portion of this solid free base (228 mg, 0.70 mmol, 1 equiv) was dissolved in methanol (3 mL) and to this was added 37% aqueous HCl (300 mg, 3.05 mmol, 2.2 equiv). The mixture was concentrated and the residue recrystallized from 2-propanol. High-vacuum drying left QT-122 (146 mg, 0.37 mmol, 53% from free base, 42% overall) as a hygroscopic tan solid: mp 203-204° C.; $^1$H NMR (400 MHz, DMSO-d$_6$): δ 2.20-2.31 (m, 4H), 3.92 (t, J=6.0 Hz, 4H), 4.38 (t, J=6.8 Hz, 4H), 6.81 (s, 4H), 7.69 (t, J=1.0 Hz, 2H), 7.84 (t, J=1.0 Hz, 2H), 9.26 (s, 2H); $^{13}$C NMR (100 MHz, DMSO-d$_6$): δ 29.1, 46.1, 65.1, 115.3, 119.7, 122.1, 135.3, 152.4; HRMS (ESI): Calcd. for C$_{18}$H$_{24}$N$_4$O$_2$ ([M−2Cl]$^{2+}$/2) 164.0944. Found 164.0953.

2.16.14. 1,4-Bis[3-(3-methylimidazolium-1-yl)propoxy] benzene diiodide (QT-123). Under a N$_2$ atmosphere, the free base form of QT-122 (458 mg, 1.40 mmol, 1 equiv) was dissolved in 1-propanol (4 mL) at rt and to this was added iodomethane (1.99 g, 14.00 mmol, 10 equiv). The mixture was stirred at reflux temperature overnight, and then cooled to rt. The dark brown solution was diluted with diethyl ether (25 mL), and stirred for 2 h resulting in an insoluble oil. The supernatant was removed using a pipette, and the oil washed with diethyl ether (2×25 mL). The brown oil was dissolved in hot ethanol (10 mL), diluted with ethyl acetate (10 mL), and stirred vigorously overnight. The solid that formed was collected by filtration. High-vacuum drying left QT-123 (510 mg, 60%) as a brown solid: mp 127-128° C.; $^1$H NMR (400 MHz, DMSO-d$_6$): δ 2.14-2.29 (m, 4H), 3.85 (s, 6H), 3.95 (t, J=6.0 Hz, 4H), 4.34 (t, J=6.8 Hz, 4H), 6.84 (s, 4H), 7.72 (t, J=1.6 Hz, 2H), 7.81 (t, J=1.6 Hz, 2H), 9.17 (s, 2H); $^{13}$C NMR (100 MHz, DMSO-d$_6$): δ 29.1, 35.8, 46.4, 64.9, 115.4, 122.4, 123.5, 136.7, 152.4; HRMS (ESI): Calcd. for C$_{20}$H$_{28}$N$_4$O$_2$ ([M−2I]$^{2+}$/2) 178.1100. Found 178.1100.

2.16.15. 1,12-Bis(4-methyl-1H-1,2,4-triazolium-1-yl) dodecane diiodide (QT-124). The dihydrochloride salt QT-121 (530 mg, 1.40 mmol) was suspended in water (30 mL) and the mixture basified with 2M NaOH. The mixture was extracted with ethyl acetate (30 mL). The organic phase was separated, washed successively with water (30 mL) and brine (10 mL), dried (Na$_2$SO$_4$), and concentrated. High-vacuum drying left the free base 1,12-bis(1H-1,2,4-triazol-1-yl)dodecane (417 mg, 1.37 mmol, 98%) as a white solid.

Under a N$_2$ atmosphere, the free base 1,12-bis(1H-1,2,4-triazol-1-yl)dodecane (417 mg, 1.37 mmol, 1 equiv) was dissolved in warm 1-propanol (7 mL) and treated with iodomethane (1.95 g, 13.72 mmol, 10 equiv). The mixture was stirred at reflux temperature overnight, and then it was cooled to rt and diluted with diethyl ether (20 mL). The solid that formed was collected by filtration, washed with diethyl ether, and then recrystallized from methanol. High-vacuum drying left QT-124 (492 mg, 61%) as an off-white solid: mp 203-204° C.; $^1$H NMR (400 MHz, DMSO-d$_6$): δ 1.18-1.34 (m, 16H), 1.77-1.89 (m, 4H), 3.89 (s, 6H), 4.35 (t, J=7.0 Hz, 4H), 9.13 (s, 2H), 10.05 (s, 2H); $^{13}$C NMR (100 MHz, DMSO-d$_6$): δ 25.4, 28.1, 28.3, 28.8, 28.9, 34.1, 51.4, 142.9, 145.4; HRMS (ESI): Calcd. for C$_{18}$H$_{34}$N$_6$ ([M−2I]$^{2+}$/2) 167.1417. Found 167.1419.

3. Determination of Anti-Plasmodium Activity

*P. falciparum* cultures were grown in O+ blood obtained by venipuncture of volunteers. Cultures of the laboratory line ItG were maintained by the method of Trager and Jensen (Trager, W.; Jensen, J. *Science* 1976, 193, 673) using RPM, 1640 supplemented with 10% human serum (a kind gift obtained under ethical consent from the Chemo Day Care department of the Princess Margaret Hospital, Toronto, Canada) and 50 µM hypoxanthine (RPMI-A). The effects of the test compounds on the viability of *P. falciparum* cultures were determined using a Lactate Dehydrogenase (LDH) enzyme assay specific to the enzyme found in *Plasmodium falciparum* (pLDH) (Prudhomme, J. G.; Sherman, I. W. *J Immunol Methods* 1999, 229(1-2), 169; Makler, M. T.; Ries, J. M.; Williams, J. A.; Bancroft, J. E.; Piper, R. C.; Gibbins, B. L.; Hinrichs, D. J. *Am J Trop Med Hyg* 1993, 48(6), 739). Briefly, compounds to be tested were dissolved in DMSO afford a solution having a concentration of 10 mg/mL. Two-fold serial dilutions were then produced in 50 µL of RPMI-A in a 96 well plate and then 50 µL of parasite culture (2% hematocrit, 2% parasitemia) were added to each well and the plates were then incubated at 37° C. in 95% $N_2$, 3% $CO_2$, and 2% $O_2$ for 72 hr. The contents of the wells were then re-suspended using a multi-channel pipettor and a 15 µL sample was removed from each well and was added to 100 µL of pLDH enzyme assay mixture (Prudhomme, J. G.; Sherman, I. W. *J Immunol Methods* 1999, 229(1-2), 169). After 1 hr the absorbance of the wells at 650 nm was determined using a ThermoMax microplate reader (Molecular Devices, Sunnyvale, Calif.). The $IC_{50}$ values of individual compounds were determined using a non-linear regression analysis of the data[19] using the computer program SigmaPlot (Jandel Scientific) and are reported in Table 1. The $IC_{50}$ values represent the mean±standard error calculated from four independent determinations. To verify if the poor viability of the cultures was related to inhibited merozoite invasion, samples were taken from treated wells and the presence of extracellular merozoites was confirmed by microscopy.

Assays comparing the activity of the compounds in human and rodent malaria cultures were preformed in a similar fashion, however parasite viability was assayed using the SYBR-Green method (Smilkstein, M.; Sriwilaijaroen, N.; Kelly, J. X.; Wilairat, P.; Riscoe, M. *Antimicrob Agents Chemother* 2004, 48(5), 1803). Rodent malaria samples were obtained by cardiac puncture of infected mice and the erythrocytes were then cultured for two days in compound diluted in RPMI 1640. Trypsin and neuraminidase treatment of human erythrocytes was as described by Lobo et al. (Lobo, C. A.; de Frazao, K.; Rodriguez, M.; Reid, M.; Zalis, M.; Lustigman, S. *Infect Immun* 2004, 72(10), 5886). and the presence of a specific invasion phenotype was confirmed by attempting to culture parasites in erythrocytes that had been subjected to the opposite treatment.

4: Mammalian Strains and Culture

CHO cells (ATCC, Manassas, Va.) were grown in RPMI-1640 supplemented with 10% fetal calf serum (Sigma, St. Louis, Mo.), 25 mM HEPES and gentimicin (RPMI-10). Cells were seeded in 96 well plates and grown to 50% confluency in 100 µL of RPMI-10 per well prior to the addition of either DMSO alone, or a 10 mg/mL solution of a test compound of the disclosure in DMSO. Compound gradients were prepared by adding 90 µL of RPMI-10 mixed with 10 µL of compound solution to the first well in the series, mixing, transferring 100 µL to the next well, and repeating until the next-to-last well was reached. After 48 hrs, the viability of the cells was determined by discarding the media in the wells and adding 100 µL of 10 mg/mL of 3-[4,5-dimethylthiazol-2-yl]-2,5-diphenyltetrazolium bromide (MTT, Sigma, St. Louis, Mo.) in RPMI-10, incubating the plates for a further hour, and then removing the media and adding 100 µL of DMSO and reading the absorbance at 650 nm (Campling, B. G.; Pym, J.; Galbraith, P. R.; Cole, S. P. *Leuk Res* 1988, 12(10), 823). The $IC_{50}$ values of individual compounds were determined using a non-linear regression analysis of the dose-response curve using the computer program SigmaPlot (Jandel Scientific) and are reported in Table 1.

5. In Vivo Evaluation of QT Compounds

Groups of 5 female Balb/C mice were infected with $10^6$ *P. berghei* parasites i.p. and the parasitemia was estimated daily by examining a Giemsa-stained blood film. Once parasites were observed mice were infused once daily with saline alone (control groups) or with 18 ug/day of QT72, 18 ug/day of QT69, 0.24 ug/day of QT98, 60 ug/day of QT109, 9 ug/day of QT119, 7.5 ug/day of QT124 or 450 ug/day of chloroquine (CQ) for three days, as indicated by the arrows in FIG. 1. Average parasitemias are shown in FIG. 1 with standard error of the mean for each experimental group indicated by bars. The separate graphs in FIG. 1 indicate the results of two separate experiments. The parasitemia of the QT98 mice was significantly lower on day 7 ($P<0.05$), and the parasitemias of the QT69 group were significantly lower on day 6 ($P<0.10$), day 7 ($P<0.01$) and day 8 ($P<0.01$). In the second experiment the parasitemias of the chloroquine treated group were significantly lower on all days following day 6 ($P<0.02$), the QT119 group had significantly lower parasitemias on day 14 ($P<0.10$) and day 15 ($P<0.03$), while the QT124 group had significantly lower parasitemias on day 7 ($P<0.03$), day 8 ($P<0.04$), day 9 ($P<0.05$) and day 10 ($P<0.02$). Parallel groups of mice that were not infected with parasites were infused with the same amounts of compounds QT109, QT119 or QT124 on the same days as the shown experimental groups and no adverse effects on the health of the mice were observed in these groups.

6. Effect of QT 69 on *P. falciparum* Cultures

Figure 2:
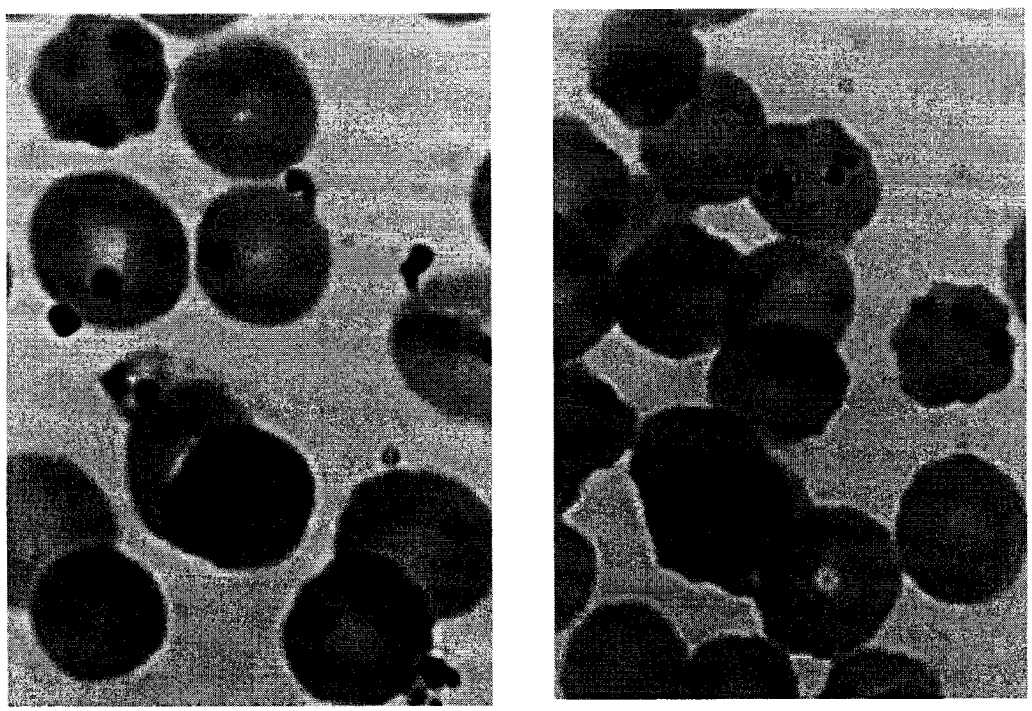
FIG. 2 shows Giemsa stained blood films of ItG cultures treated with 20 uM QT 69 (left panel) or no added compound (right panel).

As shown in FIG. 2, ItG cultures were synchronized at their mature stage of development prior to the addition of 20 uM QT 69 (left panel) or no added compound (right panel). The culture was allowed to incubate for 24 hrs before samples were withdrawn and used to produce Giemsa stained blood films. In the presence of QT 69 parasite forms were seen associated with the outside of the red cells, while in the untreated culture ring forms characteristic of normal parasite growth were observed in the red cells.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1[a]

Activities of compounds of the disclosure in CHO and *P. falciparum* cultures.[a]

| Compound | Structure | IC$_{50}$ (µM) *P. falciparum* | IC$_{50}$ (µM) CHO cells | IC$_{50}$ CHO/IC$_{50}$ *P. falciparum* |
|---|---|---|---|---|
| QT55 | 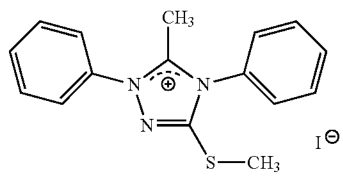 [SMILES: CSC1=NN(c2ccccc2)C(C)N1c1ccccc1 ; [I-]] | 3.1 ± 0.8 | 307 ± 37 | 99 |
| QT57 | 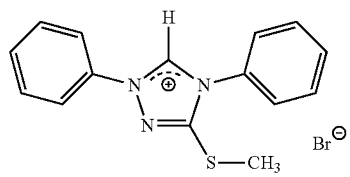 [SMILES: CSC1=NN(c2ccccc2)CN1c1ccccc1 ; [Br-]] | 69 ± 8 | 224 ± 21 | 3.3 |
| QT58 | 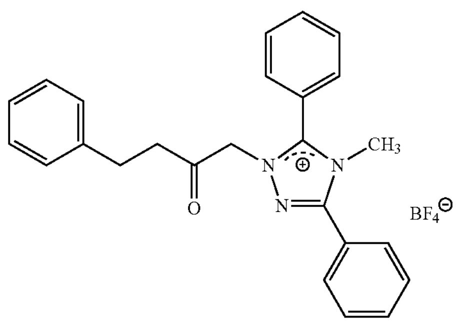 | 0.10 ± 0.08 | 143 ± 14 | 1430.0 |
| QT59 | 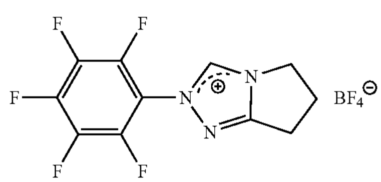 | 89 ± 5 | 303 ± 15 | 3.4 |
| QT60 | 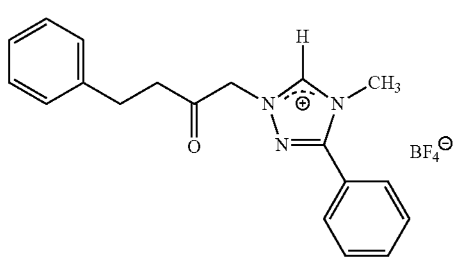 | 3.4 ± 0.2 | 237 ± 17 | 69.7 |
| QT68 | 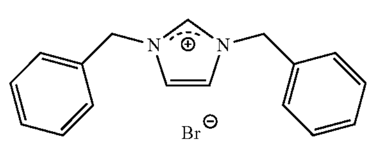 [SMILES: C1=CN(Cc2ccccc2)CN1Cc1ccccc1 ; [Br-]] | 16 ± 1 | 191 ± 3 | 11.9 |
| QT69 | 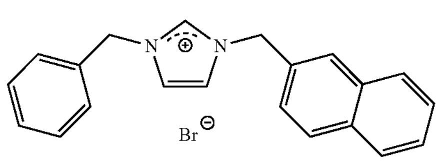 [SMILES: C1=CN(Cc2ccc3ccccc3c2)CN1Cc1ccccc1 ; [Br-]] | 0.9 ± 0.2 | 108 ± 6 | 120.0 |

TABLE 1a-continued

Activities of compounds of the disclosure in CHO and *P. falciparum* cultures.[a]

| Compound | Structure | $IC_{50}$ (μM) *P. falciparum* | $IC_{50}$ (μM) CHO cells | $IC_{50}$ CHO/$IC_{50}$ *P. falciparum* |
|---|---|---|---|---|
| QT70 | 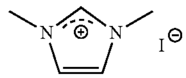 | 543 ± 66 | 894 ± 19 | 1.6 |
| QT71 | 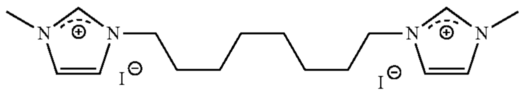 | 4.7 ± 0.9 | 452 ± 49 | 96.2 |
| QT72 | 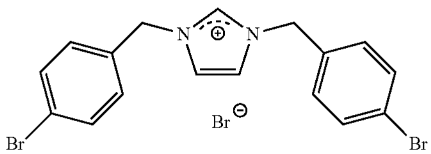 [SMILES: Brc1ccc(CN2C=CN(Cc3ccc(Br)cc3)C2)cc1 ; [Br-]] | 0.7 ± 0.1 | 171.9 ± 0.1 | 245.6 |
| QT73 | 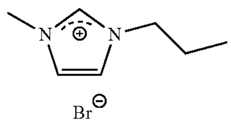 | 230 ± 83 | 998 ± 83 | 4.3 |
| QT74 | 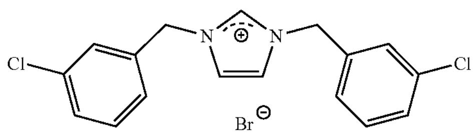 [SMILES: Clc1cccc(CN2C=CN(Cc3cccc(Cl)c3)C2)c1 ; [Br-]] | 3.3 ± 0.4 | 334.2 ± 0.4 | 101.3 |
| QT75 | 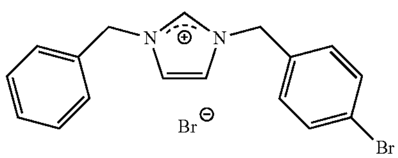 [SMILES: Brc1ccc(CN2C=CN(Cc3ccccc3)C2)cc1 ; [Br-]] | 2.9 ± 0.9 | 484.5 ± 0.9 | 167.1 |
| QT76 | 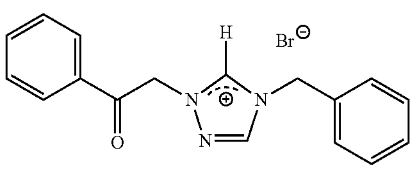 [SMILES: O=C(CN1CN(Cc2ccccc2)C=N1)c1ccccc1 ; [Br-]] | 73 ± 3 | 261 ± 3 | 3.6 |
| QT77 | 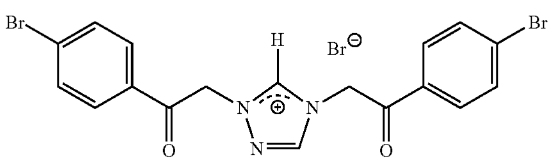 [SMILES: O=C(CN1C=NN(CC(=O)c2ccc(Br)cc2)C1)c1ccc(Br)cc1 ; [Br-]] | 10.9 ± 0.7 | 20.9 ± 0.5 | 1.9 |
| QT78 | 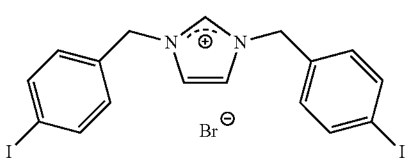 [SMILES: Ic1ccc(CN2C=CN(Cc3ccc(I)cc3)C2)cc1 ; [Br-]] | 0.35 ± 0.06 | 33 ± 1 | 94.3 |
| QT79 | 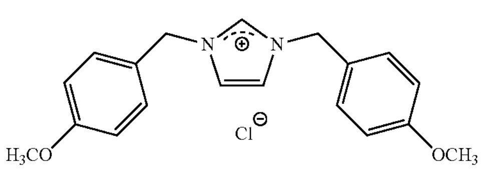 [SMILES: COc1ccc(CN2C=CN(Cc3ccc(OC)cc3)C2)cc1 ; [Cl-]] | 5 ± 1 | 30.6 ± 0.7 | 6.1 |

TABLE 1*-continued*

Activities of compounds of the disclosure in CHO and *P. falciparum* cultures.[a]

| Compound | Structure | IC$_{50}$ (µM) *P. falciparum* | IC$_{50}$ (µM) CHO cells | IC$_{50}$ CHO/IC$_{50}$ *P. falciparum* |
|---|---|---|---|---|
| QT80 | 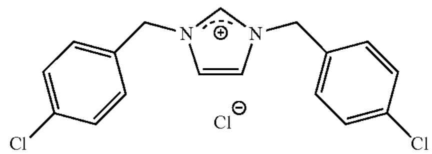 [SMILES: Clc1ccc(CN2C=CN(Cc3ccc(Cl)cc3)C2)cc1 ; [Cl-]] | 9 ± 2 | 105 ± 1 | 11.7 |
| QT81 | 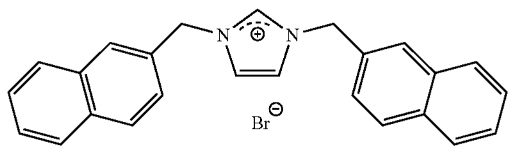 [SMILES: C1=CN(Cc2ccc3ccccc3c2)CN1Cc1ccc2ccccc2c1 ; [Br-]] | 0.9 ± 0.4 | 27 ± 1 | 30.0 |
| QT82 | 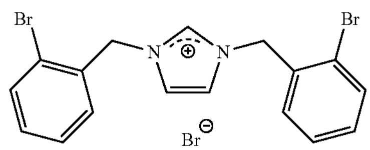 [SMILES: Brc1ccccc1CN1C=CN(Cc2ccccc2Br)C1 ; [Br-]] | 1.4 ± 0.6 | 125 ± 10 | 89.3 |
| QT83 | 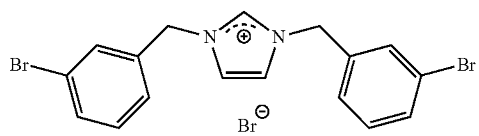 [SMILES: Brc1cccc(CN2C=CN(Cc3cccc(Br)c3)C2)c1 ; [Br-]] | 1.05 ± 0.06 | 132 ± 22 | 125.7 |
| QT84 | 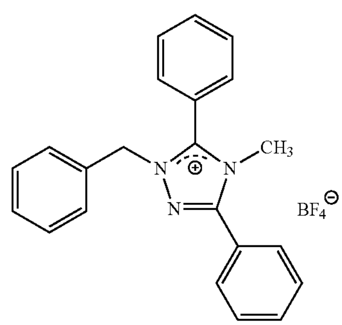 | 7.8 ± 0.2 | 87 ± 8 | 11.2 |
| QT85 | 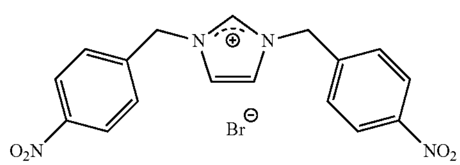 [SMILES: O=[N+]([O-])c1ccc(CN2C=CN(Cc3ccc([N+](=O)[O-])cc3)C2)cc1 ; [Br-]] | 9 ± 2 | 227 ± 7 | 25.2 |
| QT86 | 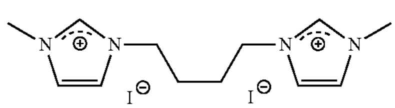 | 67 ± 22 | 122 ± 3 | 1.8 |
| QT87 | 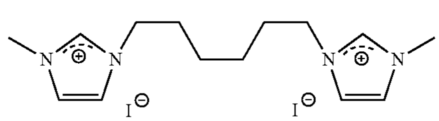 | 2.6 ± 0.8 | 146 ± 14 | 56.2 |
| QT88 | 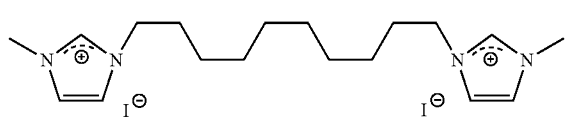 | 0.082 ± 0.009 | 57 ± 5 | 695 |

TABLE 1ᵃ-continued

Activities of compounds of the disclosure in CHO and *P. falciparum* cultures.ᵃ

| Compound | Structure | IC$_{50}$ (μM) P. falciparum | IC$_{50}$ (μM) CHO cells | IC$_{50}$ CHO/IC$_{50}$ P. falciparum |
|---|---|---|---|---|
| QT89 | 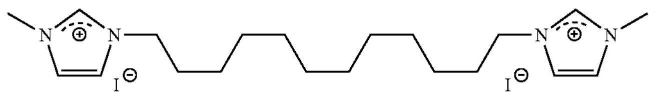 | 0.009 ± 0.001 | 26 ± 5 | 2888.9 |
| QT90 | 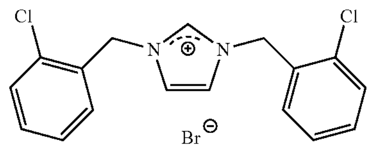 [SMILES: Clc1ccccc1CN1C=CN(Cc2ccccc2Cl)C1 ; [Br-]] | 2.0 ± 0.2 | 110 ± 23 | 55.0 |
| QT91 | 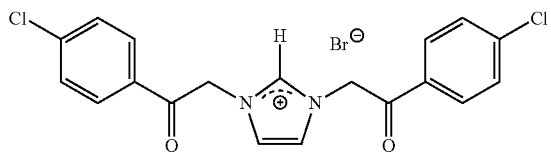 [SMILES: O=C(CN1C=CN(CC(=O)c2ccc(Cl)cc2)C1)c1ccc(Cl)cc1 ; [Br-]] | 2.6 ± 0.1 | 53 ± 2 | 20.4 |
| QT92 | 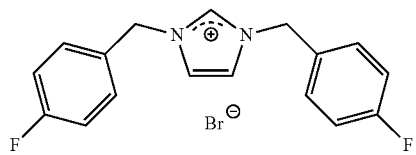 [SMILES: Fc1ccc(CN2C=CN(Cc3ccc(F)cc3)C2)cc1 ; [Br-]] | 17 ± 3 | 56 ± 4 | 3.3 |
| QT93 | 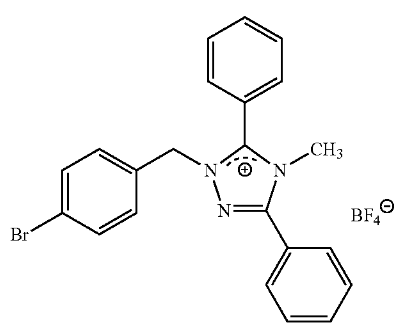 | 1.68 ± 0.05 | 33 ± 2 | 19.6 |
| QT94 | 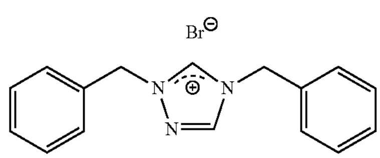 [SMILES: [Br-] ; C1=NN(Cc2ccccc2)CN1Cc1ccccc1] | 100 ± 8 | 74 ± 4 | 0.7 |
| QT95 | 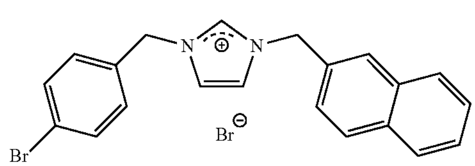 [SMILES: Brc1ccc(CN2C=CN(Cc3ccc4ccccc4c3)C2)cc1 ; [Br-]] | 0.73 ± 0.03 | 27 ± 5 | 37.0 |
| QT97 | 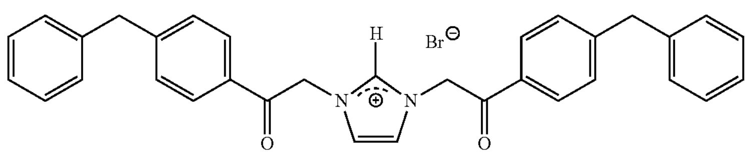 [SMILES: O=C(CN1C=CN(CC(=O)c2ccc(Cc3ccccc3)cc2)C1)c1ccc(Cc2ccccc2)cc1 ; [Br-]] | 0.5 ± 0.1 | 4.3 ± 0.3 | 9 |

TABLE 1^a-continued

Activities of compounds of the disclosure in CHO and *P. falciparum* cultures.^a

| Compound | Structure | IC$_{50}$ (μM) *P. falciparum* | IC$_{50}$ (μM) CHO cells | IC$_{50}$ CHO/IC$_{50}$ *P. falciparum* |
|---|---|---|---|---|
| QT98 | 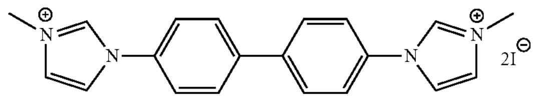 | 0.009 ± 0.001 | 9 ± 2 | 1000 |
| QT99 | 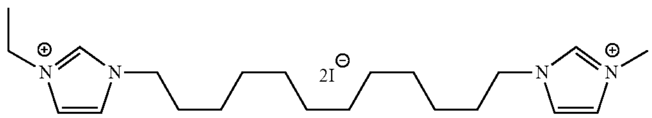 [SMILES: CC[n+]1ccn(CCCCCCCCCCCCn2cc[n+](C)c2)c1] | 0.33 ± 0.02 | 34 ± 7 | 103 |
| QT101 | 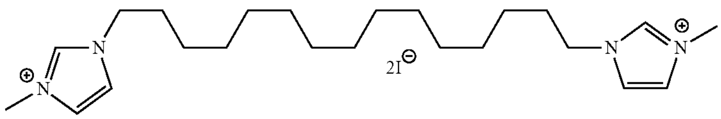 | 0.002 ± 0.001 | 1.2 ± 0.2 | 600 |
| QT102 | 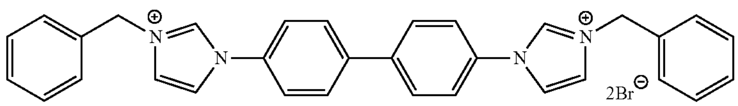 [SMILES: [c-]1ccccc1C[n+]1ccn(-c2ccc(-c3ccc(-n4cc[n+](Cc5ccccc5)c4)cc3)cc2)c1] | 0.022 ± 0.003 | 12.1 ± 0.6 | 550 |
| QT103 | 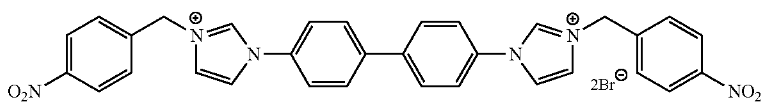 [SMILES: O=[N+]([O-])c1c[c-]c(C[n+]2ccn(-c3ccc(-c4ccc(-n5cc[n+](Cc6ccc([N+](=O)[O-])cc6)c5)cc4)cc3)c2)cc1] | 0.026 ± 0.003 | 14 ± 2 | 538 |
| QT104 | 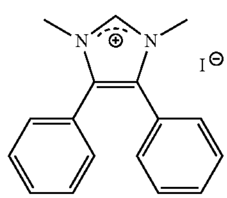 [SMILES: CN1CN(C)C(c2ccccc2)=C1c1ccccc1 ; [I-]] | 3.1 ± 0.4 | 385 ± 42 | 124 |
| QT105 | 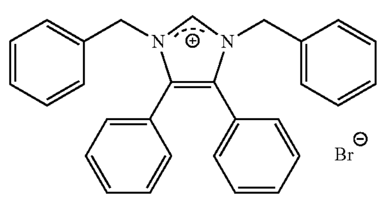 [SMILES: c1ccc(CN2CN(Cc3ccccc3)C(c3ccccc3)=C2c2ccccc2)cc1 ; [Br-]] | 1.4 ± 0.1 | 21 ± 2 | 15 |
| QT107 | 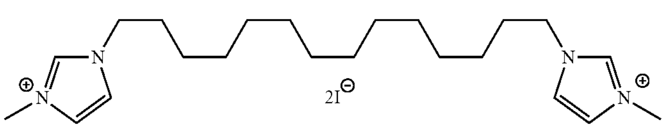 | 0.0032 ± 0.0002 | 11 ± 2 | 3438 |
| QT109 | 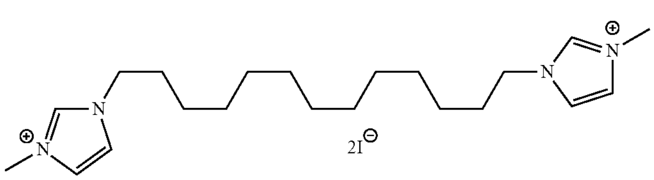 | 0.007 ± 0.003 | 51 ± 11 | 7286 |
| QT110 | 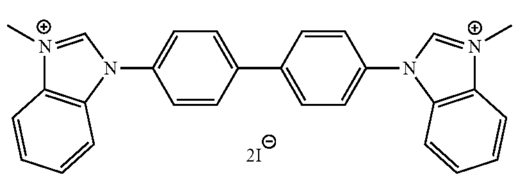 | 0.07 ± 0.01 | 98 ± 24 | 1400 |

TABLE 1ᵃ-continued

Activities of compounds of the disclosure in CHO and *P. falciparum* cultures.ᵃ

| Compound | Structure | IC$_{50}$ (µM) *P. falciparum* | IC$_{50}$ (µM) CHO cells | IC$_{50}$ CHO/IC$_{50}$ *P. falciparum* |
|---|---|---|---|---|
| QT113 | 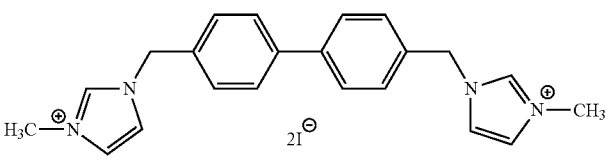 | 0.12 ± 0.04 | 125 ± 13 | 1042 |
| QT114 | 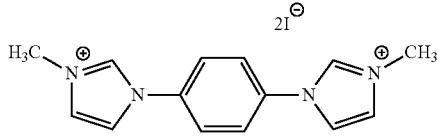 | 11.2 ± 0.5 | 317 ± 64 | 28.3 |
| QT116 | 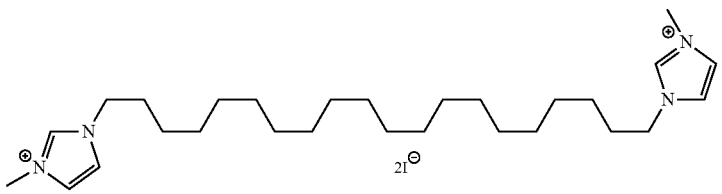 [SMILES: C[n+]1ccn(CCCCCCCCCCCCCCCCCCCCn2cc[n+](C)c2)c1] | 0.0021 ± 0.0005 | 1.4 ± 0.2 | 667 |
| QT118 | 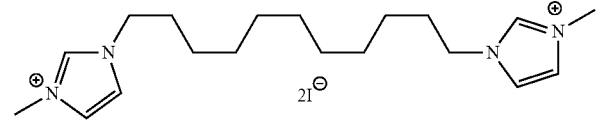 | 0.0061 ± 0.0006 | 42 ± 3 | 6885 |
| QT119 | 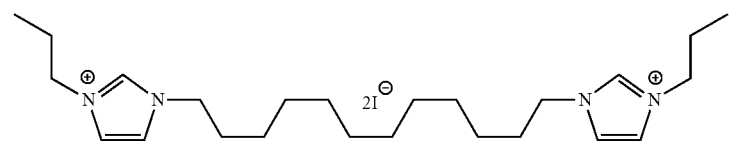 [SMILES: CCC[n+]1ccn(CCCCCCCCCCCCn2cc[n+](CCC)c2)c1] | 0.0008 ± 0.0001 | 78 ± 14 | 97500 |
| QT120 | 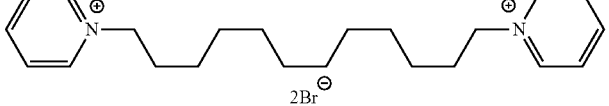 | 0.010 ± 0.003 | 330 ± 11 | 33000 |
| QT123 | 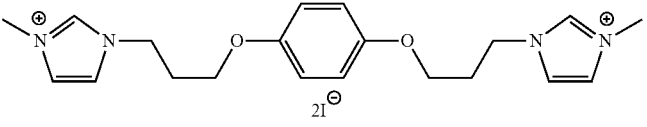 | 0.045 ± 0.004 | 113 ± 12 | 2511 |
| QT124 | 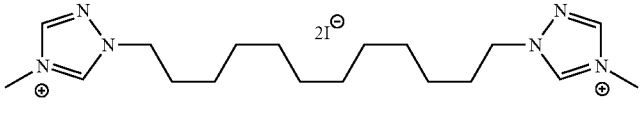 | 0.00016 ± 0.00005 | 52 ± 9 | 325000 |

ᵃEach IC$_{50}$ value represents the mean of four determinations with standard error indicated. The "ratio of activities" given in the fifth column represents the IC$_{50}$ value determined for CHO cells divided by the IC$_{50}$ value determined for *P. falciparum* cultures. Values greater than unity indicate that the compound has greater potency in *P. falciparum* cultures. The strain line used was ItG.

ᵇOxidizes erythrocytes.

ᶜNot determined.

We claim:

1. A compound selected from a compound of Formula Ic, and pharmaceutically acceptable salts thereof:

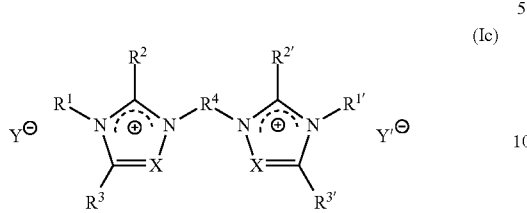

(Ic)

$R^1$ and $R^{1'}$ are independently selected from $C_{1-20}$alkyl, $C_{3-20}$cycloalkyl, $C_{6-14}$aryl and $C_{1-20}$alkylene-$C_{6-14}$aryl, where each $C_{1-20}$alkyl, $C_{3-20}$cycloalkyl and $C_{1-20}$alkylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, =O, =S, $C_{6-10}$aryl, $C_{1-4}$alkylene$C_{6-10}$aryl and $C(O)R^5$, and/or one or more carbon atoms are optionally replaced with a heteroatom independently selected from O, S and $NR^6$, and each $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$;

$R^2$ and $R^{2'}$ are independently selected from H, $C_{1-6}$alkyl, $C_{3-10}$cycloalkyl and $C_{6-14}$aryl, where $C_{1-6}$alkyl, $C_{3-10}$cycloalkyl and $C_{6-14}$aryl are unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$ and $C(O)R^5$;

$R^3$ and $R^{3'}$ are independently selected from H, $C_{1-6}$alkyl, $OC_{1-6}$alkyl, $SC_{1-6}$alkyl, $NHC_{1-6}$alkyl, $N(C_{1-6}alkyl)(C_{1-6}$ alkyl), $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$, or $R^1$ and $R^3$ and/or $R^{1'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$;

$R^4$ is selected from biphenylene, $CH_2$-biphenylene, biphenylene-$CH_2$, $CH_2$-biphenylene-$CH_2$, wherein each biphenylene is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$ and $C(O)R^5$;

$R^5$ is selected from H, OH, SH, $C_{1-6}$alkyl, $C_{3-10}$cycloalkyl, $C_{6-14}$aryl, $OC_{1-6}$alkyl, $SC_{1-6}$alkyl, $OC_{3-10}$cycloalkyl, $SC_{3-10}$cycloalkyl, $OC_{6-14}$aryl, $SC_{6-14}$aryl, $C_{1-4}$alkylene$C_{6-14}$aryl, $NH_2$, $NH(C_{1-6}alkyl)$ and $N(C_{1-6}alkyl)(C_{1-6}$ alkyl);

$R^6$ is selected from H and $C_{1-4}$alkyl;

p is 1 or 2;

X is C—$R^7$;

X' is C—$R^{7'}$;

$R^7$ and $R^{7'}$ are independently selected from H, $C_{1-6}$alkyl, $OC_{1-6}$alkyl, $SC_{1-6}$alkyl, $NHC_{1-6}$alkyl, $N(C_{1-6}alkyl)(C_{1-6}$ alkyl), $C_{3-10}$cycloalkyl, $OC_{3-10}$cycloalkyl, $SC_{3-10}$cycloalkyl, $C_{6-14}$aryl, $C_{1-6}$alkylene$C_{6-14}$aryl, $OC_{6-14}$aryl and $SC_{6-14}$aryl, where each $C_{1-6}$alkyl, $C_{1-6}$alkylene, $C_{3-10}$cycloalkyl and $C_{6-14}$aryl is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$ alkyl, fluoro-substituted $SC_{1-6}$alkyl, OH, SH, CN, $NH_2$, $NHC_{1-6}$alkyl, $N(C_{1-6}alkyl)(C_{-1-6}alkyl)$, $NO_2$, $C_{6-10}$aryl, $C_{1-4}$alkylene$C_{6-10}$aryl and $C(O)R^5$, or $R^7$ and $R^3$ and/or $R^{7'}$ and $R^{3'}$ are joined to form, together with the atoms to which they are attached, a monocyclic or bicyclic ring, where the ring is saturated, unsaturated or aromatic and is unsubstituted or substituted with one or more substituents independently selected from halo, $C_{1-6}$alkyl, $OC_{1-6}$alkyl, $SC_{1-6}$alkyl, fluoro-substituted $C_{1-6}$alkyl, fluoro-substituted $OC_{1-6}$alkyl, fluoro-substituted $SC_{1-6}$alkyl, OH, SH, CN, $NH_2$, $NHC_{1-6}$alkyl, $N(C_{1-6}alkyl)(C_{1-6}alkyl)$, $NO_2$, $C_{6-10}$aryl, $C_{1-4}$alkylene$C_{6-10}$aryl and $C(O)R^5$; and $Y^-$ and $Y^{'-}$ are, independently, a counter anion, with the proviso that, when $R^4$ is $CH_2$-biphenylene-$CH_2$, $R^1$ is not $CH_2Ph$.

2. The compound of claim 1, wherein $R^1$ and $R^{1'}$ are independently selected from $C_{1-4}$alkyl, phenyl and $C_{1-4}$alkylenephenyl, where $C_{1-4}$alkyl and $C_{1-4}$alkylene are unsubstituted or fluoro-substituted and/or substituted with one or two groups independently selected from chloro, bromo, iodo, $CH_3$, $OCH_3$, $CF_3$, $OCF_3$, OH, CN, $NH_2$, $NHCH_3$, $N(CH_3)_2$, $NO_2$ and =O and/or one or two carbon atoms are optionally replaced with O, and each phenyl is unsubstituted or fluoro-substituted and/or substituted with one to two substituents independently selected from chloro, bromo, iodo, $CH_3$, $OCH_3$, $CF_3$, $OCF_3$, OH, CN, $NH_2$, $NHCH_3$, $N(CH_3)_2$, $NO_2$ and =O.

3. The compound of claim 1, wherein $R^2$ and $R^{2'}$ are independently selected from H, $CH_3$, cyclopentyl, cyclohexyl and phenyl, where cyclopentyl, cyclohexyl and phenyl are unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$.

4. The compound of claim 1, wherein $R^3$ and $R^{3'}$ are independently selected from H, $CH_3$, $OCH_3$, $SCH_3$, $NHCH_3$, $N(CH_3)_2$, cyclopentyl, cyclohexyl, O-cyclopentyl, O-cyclohexyl, phenyl, benzyl, O-phenyl and S-phenyl, where, each phenyl, cyclopentyl and cyclohexyl is unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$.

5. The compound of claim 1, wherein $R^1$ and $R^3$ and/or $R^{1'}$ and $R^3$ are joined to form, together with the atoms to which they are attached, a monocyclic 5-membered ring, where the ring is unsaturated and is unsubstituted or substituted with one substituent selected from chloro, bromo, iodo, $CH_3$, $OCH_3$, $CF_3$, $OCF_3$, OH, SH, CN, $NH_2$, $NHCH_3$, $N(CH_3)_2$ and $NO_2$.

6. The compound of claim 1, wherein $R^4$ is selected from biphenylene, $CH_2$-biphenylene, biphenylene-$CH_2$, $CH_2$-biphenylene-$CH_2$, wherein each biphenylene is unsubstituted or fluoro-substituted and/or substituted with one to two substituents independently selected from chloro, bromo, iodo, $CH_3$, $OCH_3$, $CF_3$, $OCF_3$, OH, SH, CN, $NH_2$, $NHCH_3$, $N(CH_3)_2$ and $NO_2$.

7. The compound of claim 1, wherein $R^7$ and $R^{7'}$ are independently selected from H, $CH_3$, cyclopentyl, cyclohexyl and phenyl, where cyclopentyl, cyclohexyl and phenyl are unsubstituted or fluoro-substituted and/or substituted with one to two substituents independently selected from $CH_3$, $OCH_3$, $CF_3$, $OCF_3$, OH, CN, $NH_2$, $NHCH_3$, $N(CH_3)_2$ and $NO_2$.

8. The compound of claim 1, wherein $R^7$ and $R^3$ and/or $R^{7'}$ and $R^{3'}$ are joined to form, together with the atoms to which they are attached, a monocyclic 6-membered ring, where the ring is unsaturated or aromatic and is unsubstituted or substituted with one substituent selected from chloro, bromo, iodo, $CH_3$, $OCH_3$, $CF_3$, $OCF_3$, OH, SH, CN, $NH_2$, $NHCH_3$, $N(CH_3)_2$ and $NO_2$.

9. The compound of claim 1, wherein the compound of Formula Ic is selected from (QT98)

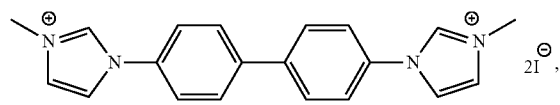

(QT102)

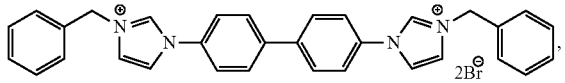

(QT103)

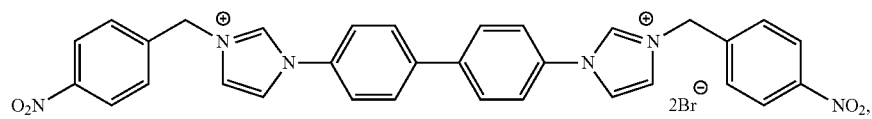

(QT110)

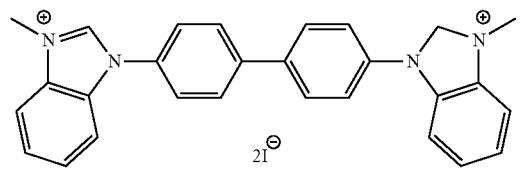

and (QT113)

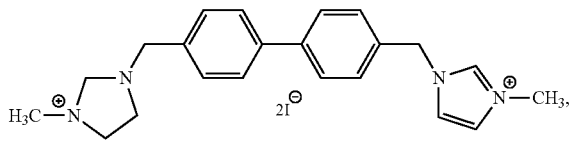

and pharmaceutically acceptable salts

\* \* \* \* \*

UNITED STATES PATENT AND TRADEMARK OFFICE
CERTIFICATE OF CORRECTION

PATENT NO. : 8,632,914 B2
APPLICATION NO. : 13/062359
DATED : January 21, 2014
INVENTOR(S) : Ian E. Crandall, Walter A. Szarek and Jason Z. Vlahakis It is certified that error appears in the above-identified patent and that said Letters Patent is hereby corrected as shown below:

In the Claims:

Column 78, line 25, replace "(C-$_{1-6}$alkyl)," with "(C$_{1-6}$alkyl)".

Column 80, last compound QT113 replace " [structure] " with " [structure] ".

Column 80, last line replace "and pharmaceutically acceptable salts" with "and pharmaceutically acceptable salts thereof.".

Signed and Sealed this
Second Day of September, 2014

Michelle K. Lee
*Deputy Director of the United States Patent and Trademark Office*